(12) United States Patent
Hanagata et al.

(10) Patent No.: US 7,655,452 B1
(45) Date of Patent: Feb. 2, 2010

(54) BREVIBACILLUS CHOSHINENSIS AND PROCESS FOR PRODCUING PROTEIN WTIH USE OF THE MICROBE AS HOST

(75) Inventors: Hiroshi Hanagata, Choshi (JP); Takayuki Nishijyo, Choshi (JP)

(73) Assignee: Higeta Shoyu Co., Ltd., Tokyo (JP)

( * ) Notice: Subject to any disclaimer, the term of this patent is extended or adjusted under 35 U.S.C. 154(b) by 220 days.

(21) Appl. No.: 10/578,781

(22) PCT Filed: Nov. 8, 2004

(86) PCT No.: PCT/JP2004/016912

§ 371 (c)(1), (2), (4) Date: May 9, 2006

(87) PCT Pub. No.: WO2005/045005

PCT Pub. Date: May 19, 2005

(30) Foreign Application Priority Data

Nov. 11, 2003 (JP) ............................... 2003-381606

(51) Int. Cl.
*C12N 1/20* (2006.01)

(52) U.S. Cl. ................ 435/252.1; 435/252.5; 424/93.1; 424/93.46

(58) Field of Classification Search ........................ None
See application file for complete search history.

(56) References Cited

U.S. PATENT DOCUMENTS

| | | | |
|---|---|---|---|
| 4,946,789 A | 8/1990 | Udaka et al. | |
| 6,284,490 B1 * | 9/2001 | Frascotti et al. ............ | 435/69.4 |

FOREIGN PATENT DOCUMENTS

| | | |
|---|---|---|
| JP | 60-58074 | 4/1985 |
| JP | 63-56277 | 3/1988 |
| JP | 4-287686 | 10/1992 |
| JP | 6-133782 | 5/1994 |
| JP | 6-296485 | 10/1994 |
| JP | 09-224677 | 9/1997 |
| JP | 10-295378 | 11/1998 |
| JP | 11-509096 | 8/1999 |
| JP | 11-514236 | 12/1999 |
| JP | 2000-279179 | 10/2000 |
| JP | 2002-142776 | 5/2002 |
| JP | 2002-371063 | 12/2002 |
| JP | 2003-180355 | 7/2003 |
| WO | 2003/006649 | 1/2003 |
| WO | WO 03/087148 A2 | 10/2003 |

OTHER PUBLICATIONS

Matsuzaki et al., J. of Bacteriology, Jun. 1985, vol. 162, pp. 1336-1338.*
Shida, Osamu et al., "Proposal for Two New Genera, *Brevibacillus* gen. nov. and *Anerurinibacillus* gen. nov.", International Journal of Systemtic Bacteriology, vol. 46, No. 4, pp. 939-946, 1996.
Ebisu, Shogo et al., "The Efficient Production of Human Epidermal Growth Factor by *Bacillus brevis*", Annals New York Academy of Sciences, vol. 782, pp. 115-122, 1996.
Hartley, James L. et al., "Nucleotide sequence of the yeast plasmid", vol. 286, pp. 860-865, 1980.
Hoang, Tung T. et al., "A broad-host-rang Flp FRT recombination system for site-specific excision of chromosomally-located DNA sequences: application for isolation of unmarked *Pseudomonas aeruginosa* mutants", Gene, vol. 212, pp. 77-86, 1998.
Shiga, Yasuhiro et al., "Characterization of an Extracellular Protease Inhibitor of *Bacillus brevis* HPD31 and Nucleotide Sequence of the Corresponding Gene", Applied Environmental Microbiology, vol. 58, No. 2, pp. 525-531, 1992.
Bernd Modest, et. al, "Peptide Antibiotics and Sporulation: Induction of Sporulation in Asporogenous and Peptide-negative Mutants of *Bacillus brevis*", Journal of General Microbiology, XP001245683, vol. 130, No. 4, Apr. 1984, pp. 747-755.
Saul Slapikoff, et al., "Sporulation in *Bacillus brevis*: Studies on Protease and Protein Turnover", Journal of Bacteriology, XP002433833, vol. 106, No. 3, Jun. 1971, pp. 739-744.
Alastair B. Fleming,et al "Extracellular Enzyme Synthesis in a Sporulation-Deficient Strain of *Bacillus licheniformis*", Applied and Environmental Microbiology, XP01070535, vol. 61, No. 11, Nov. 1995, pp. 3775-3780.
M. D. Yudkin, Structure and Function in a *Bacillus subtilis* Sporulation-specific Sigma Factor: Molecular Nature of Mutations in *spol1AC*:, Journal of General Microbiology, XP009083834, vol. 133, No. 3, Mar. 1987, pp. 475- 481.
A. Lövgren, et al. "Molecular characterization of immune inhibitor A, a secreted virulence protease from *Bacillus thuringiensis*", Molecular Microbiology, XP009083842, vol. 4, No. 12. Dec. 1990, pp. 2137-2146.

* cited by examiner

*Primary Examiner*—Irene Marx
(74) *Attorney, Agent, or Firm*—Oblon, Spivak, McClelland, Maier & Neustadt, L.L.P.

(57) ABSTRACT

*Brevibacillus choshinensis* is characterized in that its extracellular proteolytic activity is extremely low and its protein secretion productivity is excellent, but it is desired that not only the extracellular proteolytic activity of the strain is further reduced but also the intracellular proteolytic activity thereof is further reduced. When *Brevibacillus choshinensis* is used as a host for the production of protein pharmaceuticals and the like, it is also desired that it does not form spores and is readily sterilized. The above problems have been solved by inactivating the sporulation-associated gene thereof and by cloning and inactivating the extracellular and intracellular protease genes thereof.

2 Claims, 20 Drawing Sheets

Fig. 7 hos

| | | |
|---|---|---|
| 1 | ATGGGTGCCGATATCAAAAATGCGAGTCAACCATTTCTGACCAATGACCAAGTGAAAGAT | 60 |
| | MetGlyAlaAspIleLysAsnAlaSerGlnProPheLeuThrAsnAspGlnValLysAsp | |
| 61 | TTGATAGCCAAGAGCCAAGCTGGCGATACGGATGCACGTGAGCTTCTCGTGAATAGCAAT | 120 |
| | LeuIleAlaLysSerGlnAlaGlyAspThrAspAlaArgGluLeuLeuValAsnSerAsn | |
| 121 | ATCAGACTGGTCTGGTCCGTCGTCCAGCGCTTTATCAACCGCGGGTATGAAGCGGATGAT | 180 |
| | IleArgLeuValTrpSerValValGlnArgPheIleAsnArgGlyTyrGluAlaAspAsp | |
| 181 | TTGTTTCAGATCGGTTGCATTGGCTTGCTCAAGGCCGTTGACAAGTTCGATCTTTCGTAC | 240 |
| | LeuPheGlnIleGlyCysIleGlyLeuLeuLysAlaValAspLysPheAspLeuSerTyr | |
| 241 | GATGTGAGATTTTCGACCTATGCGGTGCCAATGATCATCGGAGAAATTCAACGCTTTTTG | 300 |
| | AspValArgPheSerThrTyrAlaValProMetIleIleGlyGluIleGlnArgPheLeu | |
| 301 | CGCGATGACGGTACGGTTAAGGTCAGTCGATCGTTAAAAGAAACAGCGAATAAGGTGCGG | 360 |
| | ArgAspAspGlyThrValLysValSerArgSerLeuLysGluThrAlaAsnLysValArg | |
| 361 | CGATCAAAGGATGAATTGTACAAGCAATTCGGCCGTGCCCCCACGATCGCAGAAGTGGCA | 420 |
| | ArgSerLysAspGluLeuTyrLysGlnPheGlyArgAlaProThrIleAlaGluValAla | |
| 421 | GAAGCAGTGGGAATCACGCCGGAGGAAGTAGTCTTTGCGCAAGAGGCAAGCAGAGCGCCT | 480 |
| | GluAlaValGlyIleThrProGluGluValValPheAlaGlnGluAlaSerArgAlaPro | |
| 481 | TCCTCCATCCATGAGACCGTTTTTGAAAATGACGGCGATCCCATCACACTGATCGATCAG | 540 |
| | SerSerIleHisGluThrValPheGluAsnAspGlyAspProIleThrLeuIleAspGln | |
| 541 | ATAGCGGATGAAGGTGTGAACAAGTGGTTTGAGAAAATTGCCTTGAAGGACGCCATCAGC | 600 |
| | IleAlaAspGluGlyValAsnLysTrpPheGluLysIleAlaLeuLysAspAlaIleSer | |
| 601 | AGGCTGAGCGAGCGTGAGCAGCTCATCGTCTACCTGCGCTATTACAAGGATCAGACACAG | 660 |
| | ArgLeuSerGluArgGluGlnLeuIleValTyrLeuArgTyrTyrLysAspGlnThrGln | |
| 661 | TCTGAGGTAGCAGAGCGTCTAGGGATTTCGCAGGTCCAGGTCTCGCGTCTGGAAAAGCGT | 720 |
| | SerGluValAlaGluArgLeuGlyIleSerGlnValGlnValSerArgLeuGluLysArg | |

Fig. 8

721  ATCCTGCTAACGATCAAGGAGCAAATTGAACATTAG  756
     IleLeuLeuThrIleLysGluGlnIleGluHis***

Fig. 9 emp

| | | |
|---|---|---|
| 1 | GTGAACGCAGTGAAGAAAGGCAAGAAGCTATTATCCATCCTATTTTCTTCCTCACTGGTC<br>ValAsnAlaValLysLysGlyLysLysLeuLeuSerIleLeuPheSerSerSerLeuVal | 60 |
| 61 | CTGAGCGGCATTGCGGCGGTTCCAGCGACAGGGATGGCCAAGTCAAAGGACAAGCCGCCG<br>LeuSerGlyIleAlaAlaValProAlaThrGlyMetAlaLysSerLysAspLysProPro | 120 |
| 121 | CTTGAAGTGGATTTGTCCACAGTGAACATGGATCGTTTGGTTAAAGCCTTGATCGACCAA<br>LeuGluValAspLeuSerThrValAsnMetAspArgLeuValLysAlaLeuIleAspGln | 180 |
| 181 | GGTGAAATCGACGAGGACGCCGACCAGGAAGAGATCAACAAAGCTGTGGAGAAGTTTTTG<br>GlyGluIleAspGluAspAlaAspGlnGluGluIleAsnLysAlaValGluLysPheLeu | 240 |
| 241 | AGAGACAAGAAAGTTCCCCACGGCATTGATGACTCCAGCTCCTTCGGGAAAAAAGCAAGC<br>ArgAspLysLysValProHisGlyIleAspAspSerSerSerPheGlyLysLysAlaSer | 300 |
| 301 | AAAACCCAGCTTTCGGCAGTATCAAAGGCAGCAAGCAAAGTATCCAAGCTCAAAGATGAC<br>LysThrGlnLeuSerAlaValSerLysAlaAlaSerLysValSerLysLeuLysAspAsp | 360 |
| 361 | AAGCAAGTGCGCGCTTCCAAGCGGGTACATACGGATAATCTGGTGATTGCCCTGGTCGAG<br>LysGlnValArgAlaSerLysArgValHisThrAspAsnLeuValIleAlaLeuValGlu | 420 |
| 421 | TTCAATGATCTGGAGCACAACCAGGTGCCAAAACAAAGCGATTCCTTGTGGACGGCAGAC<br>PheAsnAspLeuGluHisAsnGlnValProLysGlnSerAspSerLeuTrpThrAlaAsp | 480 |
| 481 | TTCGACCAAAAGCACTACGAGGAAATGCTGTTCGATCGTAAAGGCTATACGACTCCTGAA<br>PheAspGlnLysHisTyrGluGluMetLeuPheAspArgLysGlyTyrThrThrProGlu | 540 |
| 541 | GGGATAAGCATGACCACGATGGCCAAGTACTACTACGAGCAATCGGGTGAGACATGGACC<br>GlyIleSerMetThrThrMetAlaLysTyrTyrTyrGluGlnSerGlyGluThrTrpThr | 600 |
| 601 | GTGGATGGGGTTGTCACTCCGTGGTTGACTGCCGAAAAAGATAAGAAATTCTACGGTGGA<br>ValAspGlyValValThrProTrpLeuThrAlaGluLysAspLysLysPheTyrGlyGly | 660 |
| 661 | AACGATGAAAACGGCAACGATGCCAACCCACGCGATCTGGTCGTCGAGACACTGGAATCT<br>AsnAspGluAsnGlyAsnAspAlaAsnProArgAspLeuValValGluThrLeuGluSer | 720 |
| 721 | GTAGGGGATGCCATCAAGGGTCATGAAGAAGAATACGACCAACGCGACCCGTATGACTTG<br>ValGlyAspAlaIleLysGlyHisGluGluGluTyrAspGlnArgAspProTyrAspLeu | 780 |
| 781 | GATGGAGACAGCGATCTGATGGAGCCGGATGGCATGCTGGACAACCTGATGCTGGTTCAC<br>AspGlyAspSerAspLeuMetGluProAspGlyMetLeuAspAsnLeuMetLeuValHis | 840 |

Fig. 10

```
 841  TCCGGTATTGGTGAAGAGACTGGGGAAGATGCGGATGCGATCTGGTCTCACCGCTGGACT   900
      SerGlyIleGlyGluGluThrGlyGluAspAlaAspAlaIleTrpSerHisArgTrpThr

901  CTGAAAAAGCCGACAGAAATTCCAGGCACCAGCCTGAAAGCTTACGACTACATGATTCAG   960
      LeuLysLysProThrGluIleProGlyThrSerLeuLysAlaTyrAspTyrMetIleGln

961  CCTGAAGATGGCGCACCCGGCGTATTCGCACATGAATACGGACACAACCTGGGACTGCCA  1020
      ProGluAspGlyAlaProGlyValPheAlaHisGluTyrGlyHisAsnLeuGlyLeuPro

1021  GATCTGTATGACACGACAAGACTGGGACATGATTCGCCGGTTGGCGCATGGTCGCTGATG  1080
      AspLeuTyrAspThrThrArgLeuGlyHisAspSerProValGlyAlaTrpSerLeuMet

1081  TCTTCCGGAAGCCATACAGGTAAGATCTTCCAAACCCAACCAACCGGATTTGATCCTTGG  1140
      SerSerGlySerHisThrGlyLysIlePheGlnThrGlnProThrGlyPheAspProTrp

1141  TCCAAAATGATGCTGCAGGAAATGTATGGGGGCAAGTGGATTGAGCCGCAAGTCATCAAT  1200
      SerLysMetMetLeuGlnGluMetTyrGlyGlyLysTrpIleGluProGlnValIleAsn

1201  TACGAAGACCTGAAAAAACGGAAAAAGCAGGCTTCGCTCTACGATGGCAGCAGCCTCGAT  1260
      TyrGluAspLeuLysLysArgLysLysGlnAlaSerLeuTyrAspGlySerSerLeuAsp

1261  GAAGATGGCAAAGTCATCAAGCTGAATATGCCGCAAGTAGAGAAGACACCGCCGGTTCAA  1320
      GluAspGlyLysValIleLysLeuAsnMetProGlnValGluLysThrProProValGln

1321  CCGAAAGACGGCGATTATTCTTAGTTCTCCGATGAGGGCGACAATCTGAACACGAAGATG  1380
      ProLysAspGlyAspTyrSerTyrPheSerAspGluGlyAspAsnLeuAsnThrLysMet

1381  ACTTCGGAAGTGATCGACCTGACAGGCGCCAGCTCCGCATCGATGAGCTTCGACTCCTGG  1440
      ThrSerGluValIleAspLeuThrGlyAlaSerSerAlaSerMetSerPheAspSerTrp

1441  AGAGCGATCGAGACCGGGTACGACTACCTGTACGTGAACGTGATTGATGTCGACTCAGGT  1500
      ArgAlaIleGluThrGlyTyrAspTyrLeuTyrValAsnValIleAspValAspSerGly

1501  GAGAGCACAACAGTAAAAGAGTACGATGACGAAACCAAAGGCTGGGATAAGGAAGAAATC  1560
      GluSerThrThrValLysGluTyrAspAspGluThrLysGlyTrpAspLysGluGluIle

1561  AGCCTGAACGATTTCGCTGGCAAAAAGATTCAAGTCGAGTTCAACTACGTGACGGATGGC  1620
      SerLeuAsnAspPheAlaGlyLysLysIleGlnValGluPheAsnTyrValThrAspGly

1621  GGCTTGGCGATGTCCGGCTTCTATCTGGATAATTTTGCAGTCACAGCAGACGGCGAAGTA  1680
      GlyLeuAlaMetSerGlyPheTyrLeuAspAsnPheAlaValThrAlaAspGlyGluVal

1681  GTCTTCTCGGATGATGCAGAAGGCGACCAGAAGTTTGATCTGGATGGATTCATCCATTTC  1740
      ValPheSerAspAspAlaGluGlyAspGlnLysPheAspLeuAspGlyPheIleHisPhe
```

Fig. 11

```
1741 GACGGCGAAGGCAAAATGTACGACGCGTACTACCTGGTAGAGCTGCGCTCCCATGAAGGC  1800
     AspGlyGluGlyLysMetTyrAspAlaTyrTyrLeuValGluLeuArgSerHisGluGly

1801 GTGGACGAGGGTCTGAAATACTTCCGCCGCAATGACACATTCTTCACGTATGATCCAGGT  1860
     ValAspGluGlyLeuLysTyrPheArgArgAsnAspThrPhePheThrTyrAspProGly

1861 CTGGTGATCTGGTACTACGATGGACGCTTTGGCAAAACGCAAGACAACAACACCAGCAAC  1920
     LeuValIleTrpTyrTyrAspGlyArgPheGlyLysThrGlnAspAsnAsnThrSerAsn

1921 CATCCAGGCTACGGCATGCTGGGCGTAGTCGATGCGCATCAGGAAGTTCGTTACTGGAAT  1980
     HisProGlyTyrGlyMetLeuGlyValValAspAlaHisGlnGluValArgTyrTrpAsn

1981 AACGATGAGGGCAACGAGGAGGCCATTGCCGACTCCCGTTACCAAGTGAACGATGCGGCA  2040
     AsnAspGluGlyAsnGluGluAlaIleAlaAspSerArgTyrGlnValAsnAspAlaAla

2041 TTCAGCCCGAACAAAACCTCCGGCATGGATCTCGACTACATTCTCGGCACGATGGATTAC  2100
     PheSerProAsnLysThrSerGlyMetAspLeuAspTyrIleLeuGlyThrMetAspTyr

2101 GAGCCGCTGAAAGGCATTACCGTATTCAAAGACAGTGATGATTACACGATGCCGGAAGTT  2160
     GluProLeuLysGlyIleThrValPheLysAspSerAspAspTyrThrMetProGluVal

2161 CCGGAAATCGGAAAAATCCTGCCGAAGATCGGTCTGCAAATCAAATTAATTCGTGTGTCC  2220
     ProGluIleGlyLysIleLeuProLysIleGlyLeuGlnIleLysLeuIleArgValSer

2221 AAGAAATTCACGAACGCACAGGTCGAGTTCTCCATCAAAAAATAA  2265
     LysLysPheThrAsnAlaGlnValGluPheSerIleLysLys***
```

Fig. 12 imp

| | | |
|---|---|---|
| 1 | ATGAACCATCCTGATTTTCGCGATCTACCCGCCTGCATGGAAGACGTAACCCTCGCTGCC | 60 |
| | MetAsnHisProAspPheArgAspLeuProAlaCysMetGluAspValThrLeuAlaAla | |
| 61 | CTGGACGAGTACACTGGTCCACCAGATCCGACCGAATACCAATCATTGTATGGACGCTTG | 120 |
| | LeuAspGluTyrThrGlyProProAspProThrGluTyrGlnSerLeuTyrGlyArgLeu | |
| 121 | CAAGAGGTTGCCGAAACTCTCCCTCCGCTCTATCGGGAGCATGTGTATCACCCTTTTCTT | 180 |
| | GlnGluValAlaGluThrLeuProProLeuTyrArgGluHisValTyrHisProPheLeu | |
| 181 | CAAGCGATGGACAAGTTGTCTGAGTCAGGATTTGCGCAGATGCTCCGTCGAGATCCTCAA | 240 |
| | GlnAlaMetAspLysLeuSerGluSerGlyPheAlaGlnMetLeuArgArgAspProGln | |
| 241 | AAAGAGCGAGAAGCCGGTCTGTTTTGCGATATCGCACAGGCCATTCTGCAAAACGGCGAA | 300 |
| | LysGluArgGluAlaGlyLeuPheCysAspIleAlaGlnAlaIleLeuGlnAsnGlyGlu | |
| 301 | GCGTATGAACGCGATGCCACGGATGCCTTTCAGGAAGTAGTCAGCGATTTGTACGACGGT | 360 |
| | AlaTyrGluArgAspAlaThrAspAlaPheGlnGluValValSerAspLeuTyrAspGly | |
| 361 | TTTTTAAGCGAGGAAGACAGGAGTGGCATCAAACCGCCTGATGAAAGCTTGATTGCTCCT | 420 |
| | PheLeuSerGluGluAspArgSerGlyIleLysProProAspGluSerLeuIleAlaPro | |
| 421 | CTGGTCAAATGGGGACGCCCGCAATTCGGACCTTATACGTGGACAGCTGAAGCCGCTGCC | 480 |
| | LeuValLysTrpGlyArgProGlnPheGlyProTyrThrTrpThrAlaGluAlaAlaAla | |
| 481 | CATTTTGGCATCAAGACGGGCATTGTCAATTTGCCCCCGGCAAACGCCCGCCTGGGTCTG | 540 |
| | HisPheGlyIleLysThrGlyIleValAsnLeuProProAlaAsnAlaArgLeuGlyLeu | |
| 541 | CTCGCGTGGTCTGCATTAGGTCACGAAACGGCTGGACACGACATTCTCCACGCCGACACC | 600 |
| | LeuAlaTrpSerAlaLeuGlyHisGluThrAlaGlyHisAspIleLeuHisAlaAspThr | |
| 601 | GGTTTGCTTGGAGAACTGCAGCAAACCGTCTATGACGCTTTGTTTGATGAGCTTCACAAT | 660 |
| | GlyLeuLeuGlyGluLeuGlnGlnThrValTyrAspAlaLeuPheAspGluLeuHisAsn | |
| 661 | CGGACGCTGGCGGACTACTGGTCGCTCCGAATCGACGAGACTGCCTCCGACGTTTTGGGA | 720 |
| | ArgThrLeuAlaAspTyrTrpSerLeuArgIleAspGluThrAlaSerAspValLeuGly | |
| 721 | ATCCTGAACACCGGCCCCGCTGCAGGGATTGGACTGATTGGATATTTCCGCGGCCTTAAT | 780 |
| | IleLeuAsnThrGlyProAlaAlaGlyIleGlyLeuIleGlyTyrPheArgGlyLeuAsn | |
| 781 | AAGGCGTACACCGGACAAGCAACACTGCGGAATACAGGGCCACAGAATGACCCACATCCA | 840 |
| | LysAlaTyrThrGlyGlnAlaThrLeuArgAsnThrGlyProGlnAsnAspProHisPro | |

Fig. 13

```
841  GCAGACATCTTGCGCGGTTATCTTGCTGCTGAGACTGCTCGTCTGCTGCATTTTGACAAC  900
     AlaAspIleLeuArgGlyTyrLeuAlaAlaGluThrAlaArgLeuLeuHisPheAspAsn

901  GCATCCGACTGGGCACAGGCACTTCTCGAGGAAACCAGGCGTGATCTTAAAGGCATCACA  960
     AlaSerAspTrpAlaGlnAlaLeuLeuGluGluThrArgArgAspLeuLysGlyIleThr

961  ATAGGCAGAGCCTCTTTGGATGCAGAAACCGCTCAAAAATCTGCTGCCATTGTCGCTCGC  1020
     IleGlyArgAlaSerLeuAspAlaGluThrAlaGlnLysSerAlaAlaIleValAlaArg

1021 ACAATTATGGAAGCACGCCTGCTCAGTCTGGAAGGTCATGCCCTCGGGCAAATTCAAAAC  1080
     ThrIleMetGluAlaArgLeuLeuSerLeuGluGlyHisAlaLeuGlyGlnIleGlnAsn

1081 TGGCACAACGAGGATGAACGAATCGTTCAGGAAATTCGCTCCCATTTTACAGGTTCCCTG  1140
     TrpHisAsnGluAspGluArgIleValGlnGluIleArgSerHisPheThrGlySerLeu

1141 ACCGTGCAAGACGGCATTGTTTCGGGTATGTATGCTGCGCATGTCGTGGCAGCAGCCGTC  1200
     ThrValGlnAspGlyIleValSerGlyMetTyrAlaAlaHisValValAlaAlaAlaVal

1201 CAAGCAGCCGTTTCAGGAGAGATGGATACCTCCGCTGCCTTCACAGGGATGAAAACCTTG  1260
     GlnAlaAlaValSerGlyGluMetAspThrSerAlaAlaPheThrGlyMetLysThrLeu

1261 CTGAAGAGCATGCACGACGCCAATCCTTCCTGGGGACCTCTCTATGTACGATATCGCGGT  1320
     LeuLysSerMetHisAspAlaAsnProSerTrpGlyProLeuTyrValArgTyrArgGly

1321 GATCTCACTCCGCATCGCATTTACTCCCGTTCTGCGAGCTAG  1362
     AspLeuThrProHisArgIleTyrSerArgSerAlaSer***
```

Fig.14

| PRIMER NAME | OLIGONUCLEOTIDE SEQUENCE |
|---|---|
| Hos P1 | gggggtacctcactctgtcagcatgctg |
| Hos P2 | gggggatcccggcgtgattcccactgc |
| Hos P3 | gggctgcagatagcggatgaaggtgtg |
| Hos P4 | gggtctagacctgcttatacatctgtttcg |

Fig.15

| PRIMER NAME | OLIGONUCLEOTIDE SEQUENCE |
|---|---|
| imp P1 | gagagaccATGGACCATCCTGATTTTCGCGATCTACCCG |
| imp P2 | agaattcagtggtggtggtggtggtGCTCGCAGAACGGGAGTAAATGCGATGC |

Fig. 16 flp P1:   aaaagaattctttctgcagaacaggatgcgggggagccgccgct

Fig. 17 flp P2:   aaaaaggatccttatagcatctaatcttcaacaaact

Fig. 18 flp P3:   aaaaaaagatcttgaacgatgacctctaataattgttaa

Fig. 19 flp P4:   aaaagaattcaaatctagaaagtgtgtgctctgcgaggctgtc

Fig. 20 flp P5:   tccatggcacaatttggtatattatgtaaa

Fig. 21 flp P6:   actcgagttatatgcgtctatttatgtaggat

Fig. 22 flp P7.   tttttctagactttatgaatataaagtatagtgtgt

Fig. 23 flp P8:   gggggctgcagttatatgcgtctatttatgtaggatg

Fig.24

| PRIMER NAME | AMINO ACID SEQUENCE DATA | PRIMER OLIGONUCLEOTIDE SEQUENCE |
|---|---|---|
| emp P1 | LysArgValHisThrAspAsnLeu | aaRcgIgtNcaYacNgaYaaYct |
| emp P2 | PheGlnThrGlnProThrGlyPhe | aaNccIgtNggYtgNgtYtggaa |

I : INOSINE, R : A or G, Y : C or T, N : A or G or T or C

Fig. 25

| PRIMER NAME | OLIGONUCLEOTIDE SEQUENCE |
|---|---|
| emp P3 | cctcgtagtgctttggtcgaag |
| emp P4 | accaataccggagtgaaccagca |
| ADAPTOR PRIMER | actatagggcacgcgtggt |

Fig. 26 ctcccatggctttcgctaccccgtgcagtccgtggactgc

Fig. 27 atataagcttttagggagagaggacttccatggt

Fig. 28 tttctgcaggtaaaatcgaagaaggtaaactggta

Fig. 29 aaaaagcttttacttggtgatacgagtctgcgcg

Fig. 30 ttttggatccgaggaggtgtcggagaactgtagccac

Fig. 31 aaaaagcttctacactggcagctcctcctgtctg

Fig. 32 aaggatccccgtcatatccggca

Fig. 33 aaaagctttaggcgttatccgctttagc

Fig. 34 tatatccatggcttcttactgccaggcgccctttttaa

Fig. 35 atataagcttttattttgatgctctctggccttggaa

Fig. 36 atattcatgagcaacgacttgcttcgatccca

Fig. 37 atataagctttcagttctggagataatctgtaagta

BREVIBACILLUS CHOSHINENSIS AND PROCESS FOR PRODCUING PROTEIN WTIH USE OF THE MICROBE AS HOST

TECHNICAL FIELD

The present invention relates to novel *Brevibacillus choshinensis*. More concretely, the invention relates to *Brevibacillus choshinensis* of which the extracellular and intracellular proteolytic activity has been extremely reduced and which does not form spores. The invention also relates to a method for producing protein through genetic recombination using the *Brevibacillus choshinensis* as a host.

BACKGROUND ART

Genetic recombination has enabled mass-production of a protein which has heretofore been extremely difficult to utilize as existing only in a minor amount in living bodies and therefore difficult to isolate, and a polypeptide having any desired amino acid sequence, using bacteria or animal cells as a host. Various bacteria are used as a host for protein production through genetic recombination, and those that are most widely used are *Escherichia coli*. However, in the recombinant protein production system using *Escherichia coli* as a host, since the produced protein is accumulated in the cells, the cell volume is the uppermost limit of the produced protein and therefore mass production of protein is difficult. Further, there are other problems in that the *Escherichia coli* cells must be disrupted for the purpose of collecting the protein accumulated in the cells, and the operation for isolating and recovering the intended protein from the cell-derived component, nucleic acid, other proteins than the intended one, and the cell wall-derived endotoxin that are contained in the disrupted *Escherichia coli* cells is troublesome.

To solve the problems with *Escherichia coli* systems, a recombinant protein production system has been developed in which *Bacillus subtilis*, typical bacteria having the ability to secrete and produce protein, is used as a host. In the production system where *Bacillus subtilis* is used as a host, the produced recombinant protein is secreted and produced in the medium. Therefore, the *Bacillus subtilis* system has some excellent properties that the *Escherichia coli* system does not have, in that the former does not require cell disruption for protein recovery and the former gives little endotoxin.

On the other hand, however, *Bacillus subtilis* has the property that it extracellularly secretes a large amount of protease, and therefore, there exists a serious problem with it in that the secreted and produced recombinant protein is degraded by the protease and the yield of the recombinant protein is extremely low. Accordingly, various efforts have heretofore been made for reducing the production of the protease in *Bacillus subtilis*. Nevertheless, however, there have been to date known few examples of using a recombinant protein production system with *Bacillus subtilis* as a host for industrial production of heterogeneous proteins.

On the other hand, to solve the problem with the *Bacillus subtilis* system, a new recombinant protein production system has been developed in which are used bacteria capable of extracellularly secreting and producing a recombinant protein but not extracellularly secreting a protease, as a host. As a result, a recombinant protein production system has been successfully developed in which is used *Bacillus brevis* such as *Bacillus brevis* 47 (Patent Reference 1) that exhibits better protein secretion productivity than *Bacillus subtilis*, as a host.

At present, as a result of systematic analysis thereof based on the base sequence of 16SrRNA gene, *Bacillus brevis* is re-classified as bacteria of the genus *Brevibacillus* that includes *Brevibacillus choshinensis, Brevibacillus brevis* (Non-Patent Reference 1).

However, it has been found that *Bacillus brevis* 47 has a weak extracellular proteolytic activity. It is said that recombinant protein production using *Brevibacillus brevis* as a host takes a relatively long period of time (generally 3 days or so). Accordingly, even though the extracellular proteolytic activity of *Bacillus brevis* cells is weak, there may be a case where the produced recombinant protein may be degraded by the extracellular proteolytic activity and the yield of the recombinant protein may reduce. To solve this problem, there have heretofore been made various efforts for further reducing the extracellular proteolytic activity of *Bacillus brevis*.

For example, *Bacillus brevis* strains have been screened in a broad range, and, as those having an extremely low extracellular proteolytic activity and having an excellent protein secretion productivity, there have been isolated *Brevibacillus choshinensis* HPD31 (FERM BP-1087) (the same strain as that of FERM BP-6863: *Bacillus brevis* H102) (Patent Reference 2), and its mutant strain, *Brevibacillus choshinensis* HPD31-S5 (FERM BP-6623—this strain has been deposited as a designation of *Bacillus brevis* HPD31-S5) These strains have been utilized as a host in production of various recombinant proteins such as human epidermal growth factor (hEGF). For example, production of hEGF with *Brevibacillus choshinensis* HPD31 is shown in Non-Patent Reference 2 (in this, *Brevibacillus choshinensis* HPD31 is described as *Bacillus brevis* HPD31), etc.

However, even these *Brevibacillus choshinensis* HPD31 and HPD31-S5 showed extracellular proteolytic activity when analyzed in a high-sensitivity proteolytic activity detection method. For example, analysis of the culture supernatant of *Brevibacillus choshinensis* HPD-31 through gelatin-PAGE (zymograph) for detection of proteolytic activity thereof gave a gelatin decomposition band as in FIG. 2.

On the other hand, *Bacillus brevis* 31-OK not substantially showing a protease activity (proteolytic activity), referred to as a *Bacillus brevis* mutant strain, is disclosed (Patent Reference 3). However, even the *Bacillus brevis* 31-OK gave a band showing its proteolytic activity in its test for evaluation of the proteolytic activity thereof according to the gelatin PAGE method, and it did not completely lose the extracellular proteolytic activity. Moreover, the gene level analysis of the extracellular proteolytic activity of the strain has not been attained at all. Specifically, the protease was not isolated, and, needless-to-say, not only the sequencing of the gene thereof but also even the cloning thereof was not carried out.

Accordingly, even in the case of using strains of which the extracellular proteolytic activity has been said to be reduced, there may be a possibility that the secreted and produced protein may be degraded by the extracellular proteolytic activity that the strain still have, and therefore the yield of the protein may reduce.

These strains of *Brevibacillus choshinensis* (or *Bacillus brevis*) were obtained through screening or mutation by treatment with a mutagen, or other means, but were not through identification of the protease gene on the genome further followed by inactivation of the gene. Accordingly, to date no one knows *Brevibacillus choshinensis* of which the proteolytic activity has been reduced through identification of the protease gene on the genome further followed by inactivation of the gene.

The previously-described reduction in the proteolytic activity of *Brevibacillus choshinensis* is entirely for the reduction in the extracellular proteolytic activity thereof, and no attention has been paid to the reduction in the intracellular proteolytic activity of the strains. However, in recombinant protein production using *Brevibacillus choshinensis* as a host, there is a case where secretion production is impossible but intracellular accumulation production is possible depending on the type of the intended protein. In such a case, the produced protein may be decomposed by the action of the intracellular protease and, as a result, a recombinant protein is not almost obtained.

It is known that cells of *Brevibacillus choshinensis* may partly undergo bacetriolysis during culture, and, as a result, the intracellular protein that contains the intracellular protease may dissolve out into the medium. Accordingly, there is a possibility that even the recombinant protein extracellularly secreted and produced may be degraded by the dissolved intracellular protease.

Therefore, reducing the intracellular proteolytic activity is also another problem that is to be solved for the purpose of further increasing the usefulness of *Brevibacillus choshinensis* as a host in genetic recombination.

Heretofore, there has been known no example of reducing the intracellular proteolytic activity of *Brevibacillus choshinensis*.

In addition, gene-level analysis of *Brevibacillus choshinensis* for the intracellular proteolytic activity thereof has not been carried out at all. Specifically, there has been known no example of isolating the intracellular protease of *Brevibacillus choshinensis*. In addition, there have also been known no example of cloning the intracellular protease gene and no example of determining the sequence thereof.

Moreover, for the purpose further broadening the industrial utilization of *Brevibacillus choshinensis* as a host in genetic recombination, there is still another problem to be solved, apart from the reduction in the proteolytic activity of the strain.

*Brevibacillus choshinensis* may form spores, like bacteria of the genus *Bacillus* such as *Bacillus subtilis*. As compared with living cells (non-spore cells), spores have high heat resistance and therefore require extremely severe conditions for sterilization. Accordingly, in production of recombinant protein pharmaceuticals that require a guarantee of complete sterilization and removal of cells including spores in production lines after completion of culture, an extremely difficult technique is necessary for producing them by the use of *Brevibacillus choshinensis* as a host.

Accordingly, for the purpose of making it possible to utilize *Brevibacillus choshinensis* as a recombination host in broad-range industrial applications such as production of recombinant protein pharmaceuticals, desired are *Brevibacillus choshinensis* strains that do not form spores and can be completely killed even under mild sterilization conditions (from 60° C. to 100° C.)

The condition necessary for sterilizing the spores of *Brevibacillus choshinensis* is much milder than the condition necessary for sterilizing the spores of *Bacillus subtilis*. For example, it is said that the D value of the spores of *Bacillus subtilis* at 100° C. (the time taken for reducing the number of all cells including living cells (non-spore cells) and spores to $1/10$ in a different temperature range) will be 11 minutes or so, though varying depending on the type of the strain. On the other hand, the D value of the spores of *Brevibacillus choshinensis* is at most 1 minute. However, the sterilization of the spores of *Brevibacillus choshinensis* requires extremely severer conditions as compared with the sterilization of the living cells (non-spore cells) thereof. For example, as demonstrated in Examples given hereinunder, the D value of the living cells (no-spore cells) of *Brevibacillus choshinensis* at 80° C. is shorter than 1 minute, but the D value of the spores thereof is 67 minutes or so.

*Bacillus subtilis* SMS275 (Patent Reference 4: JP-A 4-287686 (1992)) is disclosed as anon-spore strain of *Bacillus subtilis*. However, there has heretofore been unknown any strain of *Brevibacillus choshinensis* not having the ability to form spores, or that is, capable of being completely killed under mild sterilization conditions.

Patent Reference 1:
  JP-A 60-58074 (1985)

Non-Patent Reference 1:
  Int. J. Syst. Bacteriol., 46, 939-946 (1996)

Patent Reference 2:
  JP-A 63-56277 (1988)

Non-Patent Reference 2:
  Ann. NY Acad. Sci., 782, 115-122 (1996)

Patent Reference 3:
  JP-A 6-296485 (1994)

Patent Reference 4:
  JP-A 4-287686 (1992)

PROBLEMS THAT THE INVENTION IS TO SOLVE

As so mentioned hereinabove, *Brevibacillus choshinensis* has extremely excellent properties as a host for genetic recombination, but there are some problems to be solved for further increasing the industrial usefulness of the strain as a host for genetic recombination.

One is to obtain *Brevibacillus choshinensis* of which the extracellular proteolytic activity has been remarkably reduced as compared with that of known strains. Another is to obtain *Brevibacillus choshinensis* of which the intracellular proteolytic activity has been remarkably reduced as compared with that of known strains. Still another is to obtain *Brevibacillus choshinensis* which does not form spores and which can be completely killed under mild sterilization conditions.

Accordingly, the invention is to provide *Brevibacillus choshinensis* of which the extracellular proteolytic activity has been remarkably reduced as compared with that of known strains and of which the recombinant protein secretion production efficiency has been thereby improved; *Brevibacillus choshinensis* of which the intracellular proteolytic activity has been remarkably reduced as compared with that of known strains and of which the recombinant protein intracellular accumulation production efficiency has been thereby improved; *Brevibacillus choshinensis* which does not have the ability to form spores and is therefore completely killed under mild sterilization conditions; and *Brevibacillus choshinensis* of which the extracellular and intracellular proteolytic activity has been remarkably reduced as compared with that of known strains and of which the recombinant protein production efficiency has been thereby improved, and which does not have the ability to form spores and is therefore completely killed under mild sterilization conditions. The wording "the extracellular and intracellular proteolytic activity is remarkably reduced as compared with known strains" as referred to herein is meant to include a case of complete loss of the activity.

Further, another object of the invention is to provide a method for producing a protein through genetic recombination using the Brevibacillus choshinensis as a host.

MEANS FOR SOLVING THE PROBLEMS

We, the present inventors have tried obtaining a mutant through treatment of a parent strain, Brevibacillus choshinensis HPD31 that has heretofore produced some results as a host in recombinant protein production, with a mutagen for the purpose of obtaining Brevibacillus choshinensis not having the ability to form spores.

First, on the basis of the colony morphology change as an index thereof, mutated strains are selected, and concretely those having formed colonies with no wrinkles that differ from ordinary Brevibacillus choshinensis in point of the colony morphology thereof are selected. Further, from those strains, selected are those with no spore formation through microscopic observation, as the strains having the possibility of not having the ability to form spores. Still further, the strains with the possibility of not having the ability to form spores are tested for the sporulation thereof, and those not having the ability to form spores are selected. Next, the strains are further tested for the productivity of recombinant protein with using them as a host, and those having a recombinant protein productivity on the same level as that of Brevibacillus choshinensis HPD31, a known strain utilized as a host in genetic recombination, are selected. According to the process, we, the present inventors have obtained Brevibacillus choshinensis not having the ability to form spores.

For the purpose of obtaining a strain Brevibacillus choshinensis of which the extracellular and intracellular protease activity has been much more reduced than that of known strains, we, the present inventors have used the above-mentioned Brevibacillus choshinensis not having the ability to form spores as a parent strain, and have inactivated the extracellular and intracellular major protease genes. First, concretely, we have tried cloning the protease gene for the purpose of identifying the protease gene to be inactivated. As a result, we have succeeded in cloning genes of two novel proteases, or that is, genes of an intracellular major protease IMP and an extracellular major protease EMP, and further constructed Brevibacillus choshinensis in which the genes are inactivated.

We, the present inventors have carried out the inactivation of a specific protease gene on the genome of Brevibacillus choshinensis according to a method similar to known homologous recombination, but in the process, a marker gene such as a drug-resistant gene is kept remaining on the genome in every gene inactivation, as will be mentioned hereinunder. Accordingly, for multiple gene inactivations, the marker gene such as a drug-resistant gene must be deleted from the genome in every gene inactivation. We have utilized a system comprising an FRT sequence and a yeast-derived Flp recombinase gene, for the marker gene deletion. Further in the process, we have newly constructed a plasmid DNA having an Flp recombinase gene and capable of being readily removed from the cells of Brevibacillus choshinensis cultivated in a medium not containing neomycin, and have used it, as demonstrated in Examples given hereinunder. The plasmid may be readily removed from the cells by deleting the marker gene having been introduced into the cells and left on the genome, followed by cultivating the cells in a neomycin-free medium. Using the plasmid has enabled multiple gene inactivations.

Further, we, the present inventors have tested the thus-obtained Brevibacillus choshinensis strain of which the extracellular and intracellular major protease genes have been inactivated, for its ability to form spores and for its proteolytic activity. As a result, we have confirmed that the strain has not have the ability to form spores and the extracellular and intracellular proteolytic activity of the strain has been remarkably reduced as compared with that of the known strain Brevibacillus choshinensis HPD31.

Further, we have used the Brevibacillus choshinensis strain as a host in protein production through genetic recombination, and have produced a protein of which the degradation has been confirmed after its secretion and production in a case where any other known Brevibacillus choshinensis strain is used as a host. As a result, we have confirmed that the accumulated amount of the protein has increased as compared with that in the case where the known strain Brevibacillus choshinensis HPD31 is used as a host, and have completed the present invention.

As in the above, the invention provides Brevibacillus choshinensis of which the extracellular proteolytic activity has been remarkably reduced as compared with that of known strains and of which the recombinant protein secretion production efficiency has been thereby improved; Brevibacillus choshinensis of which the intracellular proteolytic activity has been remarkably reduced as compared with that of known strains and of which the recombinant protein intracellular accumulation production efficiency has been thereby improved; and Brevibacillus choshinensis which does not have the ability to form spores and is therefore completely killed under mild sterilization conditions. The invention further provides Brevibacillus choshinensis of which the extracellular and intracellular proteolytic activity has been remarkably reduced as compared with that of known strains and of which the recombinant protein production efficiency has been thereby improved, and which does not have the ability to form spores and is therefore completely killed under mild sterilization conditions.

Still further, the invention provides a method for producing a protein through genetic recombination using the Brevibacillus choshinensis as a host.

BRIEF DESCRIPTION OF THE DRAWINGS

FIG. 7:
It shows a DNA base sequence (SEQ ID NO: 1) (upper line) of a sporulation-associated gene hos, and an amino acid sequence (SEQ ID NO: 2) (lower line) corresponding to it.

FIG. 8:
It is a continuation of FIG. 7 (continuation of both SEQ ID NO: 1 and SEQ ID NO: 2).

FIG. 9:
It shows an amino acid sequence (SEQ ID NO: 4) (lower line) of an extracellular protease EMP, and a DNA sequence (SEQ ID NO: 3 (upper line) of a gene emp encoding it.

FIG. 10:
It is a continuation of FIG. 9 (continuation of both SEQ ID NO: 3 and SEQ ID NO: 4).

FIG. 11:
It is a continuation of FIG. 10 (continuation of both SEQ ID NO: 3 and SEQ ID NO: 4).

FIG. 12:
It shows an amino acid sequence (SEQ ID NO: 6) (lower line) of an intracellular protease IMP, and a DNA sequence (SEQ ID NO: 5) (upper line) of a gene imp encoding it.

FIG. 13:
It is a continuation of FIG. 12 (continuation of both SEQ ID NO: 5 and SEQ ID NO: 6).

FIG. 14:
It shows primers Hos P1 (SEQ ID NO: 7), Hos P2 (SEQ ID NO: 8), Hos P3 (SEQ ID NO: 9), and Hos P4 (SEQ ID NO: 10).

FIG. 15:
It shows primers imp P1 (SEQ ID NO: 11) and imp P2 (SEQ ID NO: 12).

FIG. 16:
It shows a primer flp P1 (SEQ ID NO: 13).

FIG. 17:
It shows a primer flp P2 (SEQ ID NO: 14).

FIG. 18:
It shows a primer flp P3 (SEQ ID NO: 15).

FIG. 19:
It shows a primer flp P4 (SEQ ID NO: 16).

FIG. 20:
It shows a primer flp P5 (SEQ ID NO: 17).

FIG. 21:
It shows a primer flp P6 (SEQ ID NO: 18).

FIG. 22:
It shows a primer flp P7 (SEQ ID NO: 19).

FIG. 23:
It shows a primer flp P8 (SEQ ID NO: 20).

FIG. 24:
It shows an oligonucleotide base sequence (SEQ ID NO: 21) and an amino acid sequence (SEQ ID NO: 38) of an emp P1 primer, as well as an oligonucleotide base sequence (SEQ ID NO: 22) and an amino acid sequence (SEQ ID NO: 39) of an emp P2 primer.

FIG. 25:
It shows primers emp P3 (SEQ ID NO: 23) and emp P4 (SEQ ID NO: 24), and an adaptor primer (SEQ ID NO: 25).

FIG. 26:
It shows a sense primer in Example 19 (SEQ ID NO: 26).

FIG. 27:
It shows an antisense primer in Example 19 (SEQ ID NO: 27).

FIG. 28:
It shows a sense primer in Example 20 (SEQ ID NO: 28).

FIG. 29:
It shows an antisense primer in Example 20 (SEQ ID NO: 29).

FIG. 30:
It shows a sense primer in Example 21 (SEQ ID NO: 30).

FIG. 31:
It shows an antisense primer in Example 21 (SEQ ID NO: 31).

FIG. 32:
It shows a sense primer in Example 23 (SEQ ID NO: 32).

FIG. 33:
It shows an antisense primer in Example 23 (SEQ ID NO: 33).

FIG. 34:
It shows a sense primer in Example 24 (SEQ ID NO: 34).

FIG. 35:
It shows an antisense primer in Example 24 (SEQ ID NO: 35).

FIG. 36:
It shows a sense primer in Example 25 (SEQ ID NO: 36).

FIG. 37:
It shows an antisense primer in Example 25 (SEQ ID NO: 37).

Figure 1:
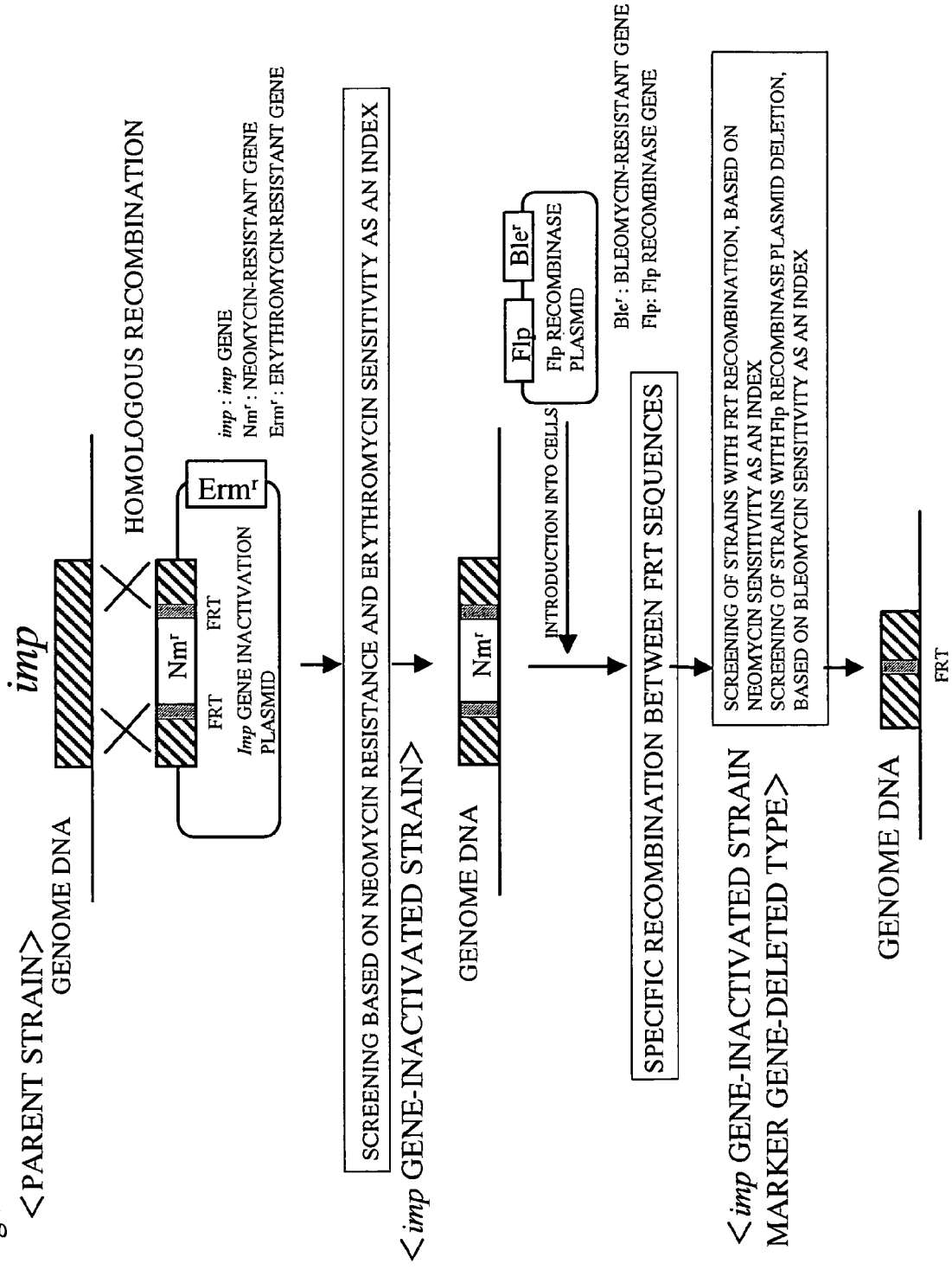
FIG. 1:
It is a drawing showing the outline of gene inactivation through homologous recombination used for construction of Brevibacillus choshinensis of the invention.

The invention is described in detail hereinunder.
The invention includes the following (1) to (16) as its embodiments.

(1) *Brevibacillus choshinensis* not forming spores.
(2) *Brevibacillus choshinensis* having the following mycological properties and not forming spores:

(a) Morphology:
size of cell:
liquid medium: 0.4 to 0.6×1.5 to 4 µm,
form of cell: *bacillus*,
presence or absence of spore: absence, (b) Physiological Properties:
reduction of nitrate: −,
VP test: −,
utilization of citric acid: +,
urease: −,
oxidase: +,
catalase: +, (c) Other Properties:
   temperature resistance: die at 60° C.

(3) *Brevibacillus choshinensis* not forming spores, characterized in that its sporulation-associated gene hos is inactivated.

(4) *Brevibacillus choshinensis* of (3), wherein the sporulation-associated gene hos has a base sequence of SEQ ID NO: 1.

(5) *Brevibacillus choshinensis* not forming spores, of which the extracellular and/or intracellular protease activity has been reduced or lost.

(6) *Brevibacillus choshinensis* having the following mycological properties and not forming spores:

(a) Morphology:
   size of cell:
   liquid medium: 0.4 to 0.6×1.5 to 4 µm,
   form of cell: *bacillus,*
   presence or absence of spore: absence, (b) Physiologica properties:
   reduction of nitrate: −,
   VP text: −,
   utilization of citric acid: +,
   urease: −,
   oxidase: +,
   catalase: +, (c) Other Properties:
   temperature resistance: die at 60° C.,
   extracellular protease activity: low or absent,
   intracellular protease activity: low or absent.

(7) *Brevibacillus choshinensis* characterized in that its extracellular major protease gene emp is inactivated.

(8) *Brevibacillus choshinensis* of (7), wherein the extracellular major protease gene emp has a base sequence of SEQ ID NO:3.

(9) *Brevibacillus choshinensis* characterized in that its intracellular major protease gene imp is inactivated.

(10) *Brevibacillus choshinensis* of above (9), wherein the intracellular major protease gene imp has a base sequence of SEQ ID NO:5.

(11) *Brevibacillus choshinensis* characterized in that its extracellular major protease gene emp and its intracellular major protease gene imp are inactivated.

(12) *Brevibacillus choshinensis* of above (11), which does not form spores.

(13) *Brevibacillus choshinensis* HPD31-SP3 (FERM BP-08479).

(14) *Brevibacillus choshinensis* constructed by transforming the *Brevibacillus choshinensis* of any one of above (1) to (13) with an expression vector having a protein-encoding gene inserted thereinto.

(15) A method for producing a protein, characterized by including a step of cultivating the *Brevibacillus choshinensis* transformant of above (14).

(16) A method for producing a recombinant protein, characterized by using the *Brevibacillus choshinensis* of any one of above (1) to (13) as a host in recombinant protein production.

The *Brevibacillus choshinensis* not having the ability to form spores of the invention has been obtained by mutating a parent strain, *Brevibacillus choshinensis* with a mutagen, followed by selecting a strain not having the ability to form spores from the mutants obtained as a result of the mutation. In Examples given below, nitrosoguanidine was used as the mutagen, but nitrous acid or ethyl methanesulfonate is also usable as the mutagen. In addition, UV rays and γ rays are also usable. The parent strain for obtaining the mutant not having the ability to form spores of the invention is not specifically limited, so far as it is a strain belonging to the genus *Brevibacillus choshinensis*, but is especially preferably *Brevibacillus choshinensis* HPD31 (FERM BP-1087) or its mutant *Brevibacillus choshinensis* HPD31-S5 (FERM BP-6623) that has produced some results as a host in protein production through genetic recombination. The presence or absence of the sporulation ability of the mutants obtained through the mutation may be confirmed by a heat resistance test or by measurement of the D value of the mutants. The D value means the time taken for reducing the number of all cells including living cells (non-spore cells) and spores to 1/10 in each temperature range, and this is used as an index of the death ratio of cells.

The *Brevibacillus choshinensis* strain with no sporulation ability that the invention provides has been analyzed by the use of a genome library, and it has been confirmed that the gene in the strain that is presumed to be associated with sporulation is inactivated. The inactivated gene is named hos. As an example of the DNA sequence of the sporulation-associated gene hos, the DNA base sequence of hos of *Brevibacillus choshinensis* HPD31 is shown as SEQ ID NO: 1 (upper line in FIG. 7 and FIG. 8), and the amino acid sequence corresponding to the DNA base sequence is shown as SEQ ID NO: 2 (lower line in FIG. 7 and FIG. 8).

The *Brevibacillus choshinensis* of the invention, of which the extracellular and intracellular proteolytic activity has been remarkably reduced, may be obtained by inactivating the extracellular and intracellular major protease genes on the genome of *Brevibacillus choshinensis*. For obtaining the *Brevibacillus choshinensis* of the invention of which the proteolytic activity has been remarkably reduced, the protease gene on the genome of *Brevibacillus choshinensis* is not specifically defined, but is preferably any of an intracellular major protease gene imp and an extracellular major protease gene emp.

As an example of the DNA sequence of the extracellular major protease gene emp, the DNA base sequence of the emp gene of *Brevibacillus choshinensis* HPD31 is shown as SEQ ID NO:3 (upper line in FIGS. 9 to 11); and the amino acid sequence of the extracellular major protease EMP of *Brevibacillus choshinensis* HPD31 corresponding to the DNA sequence is shown as SEQ ID NO: 4 (lower line in FIGS. 9 to 11).

As an example of the DNA sequence of the intracellular major protease gene imp, the DNA base sequence of the imp gene of *Brevibacillus choshinensis* HPD31 is shown as SEQ ID NO:5 (upper line in FIGS. 12 to 13); and the amino acid sequence of the intracellular major protease IMP of *Brevibacillus choshinensis* HPD31 corresponding to the DNA sequence is shown as SEQ ID NO: 6 (lower line in FIGS. 12 to 13). EMP and IMP are both novel proteins lacking at least 40% homology to the amino acid sequence of any known protein.

Any and every protein of which the amino acid sequence is modified from the amino acid sequence of SEQ ID NO:4 through partial substitution, deletion, insertion or addition of some amino acids is all within the scope of the protease EMP so far as it has a proteolytic s activity. The "amino acid sequence modified through partial substitution, deletion, insertion or addition of some amino acids" as referred to herein is meant to indicate a modified amino acid sequence having at least 60%, preferably at least 70%, more preferably at least 80% homology to the full length amino acid sequence of SEQ ID NO:4, though varying depending on the type of the amino acid residues and the position of the amino acid residues in the protein stereostructure.

Similarly, any and every protein of which the amino acid sequence is modified from the amino acid sequence of SEQ ID NO:6 through partial substitution, deletion, insertion or addition of some amino acids is all within the scope of the protease IMP so far as it has a proteolytic activity. The "amino acid sequence modified through partial substitution, deletion, insertion or addition of some amino acids" as referred to herein is meant to indicate a modified amino acid sequence having at least 50%, preferably at least 60%, more preferably at least 70% homology to the full length amino acid sequence of SEQ ID NO: 6, though varying depending on the type of the amino acid residues and the position of the amino acid residues in the protein stereostructure.

Also similarly, any and every gene that codes for the protein of which the amino acid sequence is modified from the amino acid sequence of SEQ ID NO: 4 through partial substitution, deletion, insertion or addition of some amino acids is all within the scope of the protease gene emp (SEQ ID NO:3) so far as the protein encoded by it has a proteolytic activity. The "amino acid sequence modified through partial substitution, deletion, insertion or addition of some amino acids" as referred to herein has the same meaning as that mentioned hereinabove for EMP.

Still similarly, any and every gene that codes for the protein of which the amino acid sequence is modified from the amino acid sequence of SEQ ID NO: 6 through partial substitution, deletion, insertion or addition of some amino acids is all within the scope of the protease gene imp (SEQ ID NO:5) so far as the protein encoded by it has a proteolytic activity. The "amino acid sequence modified through partial substitution, deletion, insertion or addition of some amino acids" as referred to herein has the same meaning as that mentioned hereinabove for IMP. Both emp gene and imp gene have not been heretofore isolated and their DNA sequences have not been determined, and the two genes are novel genes heretofore unknown in the art.

Cloning of the intracellular major protease gene imp and the extracellular major protease gene emp on the genome of *Brevibacillus choshinensis* may be carried out by suitably selecting and combining standard genetic recombination techniques known to those skilled in the art and described in, for example, Molecular Cloning, 2nd Ed., A Laboratory Manual, Cold Spring Harbor Laboratory Press, New York (1989). For example, a genome DNA library of *Brevibacillus choshinensis* is prepared, and with the genome DNA library, a DNA fragment having a part of the DNA sequence that encodes the gene to be inactivated is subjected to hybridization as a probe, or the DNA fragment is subjected to PCR as a primer.

Inactivation of the imp gene or the emp gene on the genome of *Brevibacillus choshinensis* may be carried out according to a method similar to known homologous recombination. For example, the imp gene inactivation may be effected according to the process mentioned below.

First, an imp gene-containing DNA fragment is cloned with a vector not replicable in *Brevibacillus choshinensis*, for example, with a vector replicable in *Escherichia coli*, whereby a partial region of the imp gene is substituted with a DNA fragment that comprises a drug-resistant gene (for example, neomycin-resistant gene) having an FRT sequence (Gene, 212, 77-86 (1998)) on both sides thereof and the imp gene is thereby cleaved. As a result, an inactivated imp gene-containing vector is obtained, in which the imp gene is partly substituted with the neomycin-resistant gene and is therefore inactivated. Further, a second drug-resistant gene (for example, erythromycin-resistant gene) is inserted into the vector for the purpose of selecting the *Brevibacillus choshinensis* strain with the above-mentioned inactivated imp gene inserted into the genome DNA thereof to thereby construct a vector for imp gene inactivation.

Next, the imp gene inactivation vector is introduced into *Brevibacillus choshinensis*, and a strain that shows neomycin resistance is selected. The imp gene inactivation vector introduction induces homologous recombination between the imp gene on the genome and the inactivated imp gene on the imp gene inactivation vector in some cells of *Brevibacillus choshinensis*. As a result, the neomycin-resistant strains include a strain with homologous recombination having occurred only in the imp part upstream the neomycin-resistant gene-FRT cassette; a strain with homologous recombination having occurred only in the imp part downstream it; and a strain (double crossover strain) with homologous recombination having occurred in the two parts upstream and downstream it.

The intended strain in which the imp gene on the genome has been inactivated is the double crossover strain, and the double crossover strain is sensitive to erythromycin. Accordingly, these neomycin-resistant strains are further cultivated on an erythromycin-containing TM-agar medium, and the strain sensitive to erythromycin is selected. The process gives the intended *Brevibacillus choshinensis* strain in which the imp gene on the genome has been inactivated.

The inactivation of the imp gene in the *Brevibacillus choshinensis* strain obtained in the above can be confirmed through PCR and genomic Southern analysis.

Further, the neomycin-resistant gene is deleted from the genome of the imp gene-inactivated strain obtained in the above. The neomycin-resistant gene introduced into the imp gene-inactivated strain has an FRT sequence in both the upstream region and the downstream region thereof, and therefore, it is possible to delete the neomycin-resistant gene from the imp gene-inactivated strain obtained in the above, through FRT sequence recombination using an Flp recombinase capable of specifically recognizing the FRT sequence.

Concretely, in the case of cultivation in a neomycin-free medium, a plasmid vector capable of readily leaving from a *Brevibacillus choshinensis* strain is first prepared. Further, a neomycin-resistant gene-deleting vector is constructed by inserting an yeast-derived Flp recombinase gene (Nature, 286, 860-864 (1980)) and a bleomycin-resistant gene into the plasmid vector.

Next, the neomycin-resistant gene-deleting vector is introduced into the imp gene-inactivated strain obtained in the above, and then this is cultivated on a bleomycin-containing TM-agar medium and a strain transformed with the vector is thereby selected. Next, the resulting transformant strain is cultivated with shaking in a bleomycin-free liquid TM medium and then further cultivated in a TM-agar medium.

The intended, imp gene-inactivated strain where the neomycin-resistant gene has been deleted is a strain in which the neomycin-resistant gene on the genome has been deleted through the FRT sequence recombination on both sides of the neomycin-resistant gene and which has lost the neomycin-resistant gene-deleting vector. This strain is sensitive to both neomycin and bleomycin. Accordingly, the strain sensitive to both neomycin and bleomycin is selected from the strains having formed colonies on the TM-agar medium, whereby the intended, neomycin-resistant gene-deleted, imp gene-inactivated strain is obtained.

The process gives the intended, imp gene-inactivated strain of *Brevibacillus choshinensis*. Its outline is shown in FIG. 1.

The *Brevibacillus choshinensis* strain in which both the protease genes imp and emp have been inactivated can be obtained by using the above-constructed imp gene-inactivated strain as a parent strain and by inactivating the emp gene on the genome of the strain. The emp gene inactivation can be carried out by repeating the same process as that for the imp gene inactivation.

The drug-resistant genes such as neomycin-resistant gene, erythromycin-resistant gene and bleomycin-resistant gene used as a marker gene in the above-mentioned method are examples, and the type of the marker gene for use in the method is not specifically defined. Using any desired plural marker genes, genes may be inactivated through homologous recombination according to the process as above.

The above-mentioned inactivation of the extracellular and intracellular major protease genes on the genome of *Brevibacillus choshinensis* gives the *Brevibacillus choshinensis* strain of the invention of which the extracellular and intracellular proteolytic activities have been much more reduced than that of known strains.

The proteolytic activity of the *Brevibacillus choshinensis* strain may be determined according to a gelatin-PAGE (zymogram) method or a method using an azo-protein such as azocasein or azocol as a substrate.

An example of the *Brevibacillus choshinensis* with no sporulation ability of the invention, which is obtained according to the method as above, is *Brevibacillus choshinensis* HPD31-SP1 shown in Examples. An example of the *Brevibacillus choshinensis* of which the intracellular proteolytic activity has been much more reduced than that of known strains and which does not have the ability to form spores is *Brevibacillus choshinensis* HPD31-SP2 also shown in Examples. An example of the *Brevibacillus choshinensis* of which the extracellular and intracellular proteolytic activities have been much more reduced than that of known strains and which does not have the ability to form spores is *Brevibacillus choshinensis* HPD31-SP3 also shown in Examples.

*Brevibacillus choshinensis* HPD31-SP3 was internationally deposited under the Budapest treaty in the International Patent Organism Depositary (1-1, Higashi 1-chome, Tsukuba-shi, Ibaraki-ken) on Sep. 11, 2003, and it is assigned Receipt No. FERM BP-08479.

The *Brevibacillus choshinensis* of the invention is characterized in that it satisfies at least one of three requirements that (a) it does not form spores, (b) its extracellular major protease activity is low or absent, (c) its intracellular major protease activity is low or absent; and it does not so much differ from ordinary *Brevibacillus choshinensis* in point of the other properties thereof. Its mycological properties are as follows:

(a) Morphology:
  size of cell:
    liquid medium: 0.4 to 0.6×1.5 to 4 μm,
  form of cell: *bacillus*,
  presence or absence of spore: absence,
  presence or absence of polymorphism of cell: absence,
  presence or absence of mobility: presence (peripheric flagellum), (b) Physiological properties:
  reduction of nitrate: −,
  VP test (acetoin formation): −,
  indole formation: −,
  hydrogen sulfide formation (TSI agar medium): +
  utilization of citric acid: +,
  utilization of inorganic nitrogen source: +
  nitrate: −,
  ammonium salt: +,
  dye formation (King medium): −
  urease: −,
  oxidase: +,
  catalase: +,
  O-F test: not decomposed,
  gelatin decomposition: −,
  formation of acid from glucose: −,
  formation of acid from xylose: −,
  formation of acid from lactose: −,
  formation of acid from maltose: −,
  PH for growth: 6 to 8.5, (c) Other properties:
  temperature resistance: die at 60° C.,
  extracellular protease activity: low or absent (note 1),
  intracellular protease activity: low or absent (note 2).

(Note 1)
Proteolysis activity is not detected in the culture supernatant in any of the following methods:

(1) Method of measurement of gelatin decomposition activity by gelatin-PAGE.

(2) Method of measurement of azocasein decomposition activity by reacting the culture supernatant with azocasein followed by measuring the change in the absorbance of the reaction liquid.

(3) Method of measurement of azocoll decomposition activity by reacting the culture supernatant with azocoll followed by measuring the change in the absorbance of the reaction liquid.

(Note 2)
Even in the measurement of gelatin decomposition activity by gelatin-PAGE, no gelatin decomposition activity is detected in the intracellular fraction.

The wording "the extracellular protease activity has been much more reduced than that of known strains" as referred to herein means that the enzyme activity in the culture supernatant, when measured according to the azocasein method or the azocoll method, is reduced to at most $1/10$, preferably at most $1/30$, more preferably at most $1/100$ of the enzyme activity of known *Brevibacillus choshinensis* strains. In Examples given hereinunder, shown are data of at most $1/120$ and at most $1/330$.

Similarly, the wording "the intracellular protease activity has been much more reduced than that of known strains" means that the enzyme activity in the intracellular fraction, when measured according to the azocasein method, is reduced to at most $1/2$, preferably at most $1/5$, more preferably at most from $1/8$ to $1/10$ of the enzyme activity of known *Brevibacillus choshinensis* strains.

These reduced values are obtained in measurement according to the azocasein method or the azocoll method, and, needless-to-say, when the data are measured in any other methods, then the reduced values in each method shall be defined on the basis of these reduced values.

Further, the invention provides a method for producing a protein through genetic recombination using the above-mentioned *Brevibacillus choshinensis* as a host strain.

The expression vector for use in the protein production using the *Brevibacillus choshinensis* of the invention as a host strain may be any and every one replicable in *Brevibacillus choshinensis*, not specifically defined, but is preferably an expression vector that has a promoter region of a major extracellular protein gene (MWP gene) of *Bacillus brevis* 47 or a promoter region of a major extracellular protein gene (HWP gene) of *Brevibacillus choshinensis* HPD31. In general, the protein produced in a recombinant protein production system using *Brevibacillus choshinensis* as a host is not accumulated inside the host cells but is secreted outside the cells, and therefore, it is desirable that the expression vector has a DNA sequence encoding a secretion signal peptide at the 3'-terminus side of the DNA sequence encoding a promoter region. A preferable example of the DNA sequence encoding a secretion signal peptide includes a DNA sequence encoding the secretion signal peptide of a major extracellular protein of *Brevibacillus choshinensis* HPD31.

Concretely, a preferable example of the expression vector for use in the recombinant protein production using the *Brevibacillus choshinensis* of the invention as a host includes pHT110 (JP-A 6-133782 (1994) and pNY301 (JP-A 10-295378 (1998)).

A DNA that encodes a protein to be inserted into the expression vector in the invention may be any and every one, not specifically limited, that enables its expression in the recombinant protein production using the *Brevibacillus choshinensis* of the invention as a host. For example, it may be any DNA fragment that encodes any gene of cytokine, chemokine, enzyme or hormone, or any other peptide. The use of the protein produced through the genetic recombination is not also specifically limited. The use may be for any of pharmaceuticals, biochemical reagents, industrial enzymes, etc.

The protein-encoding DNA may be inserted into an expression vector in any ordinary method known to those skilled in the art. For example, a DNA fragment obtained through treatment of a purified DNA that encodes the intended protein with a suitable restriction endonuclease is inserted into a suitable restriction endonuclease cleavage site or multi-cloning site of an expression vector, and ligated therein.

Further, the expression vector with the protein-encoding DNA inserted thereinto is introduced into the *Brevibacillus choshinensis* of the invention to thereby transform the *Brevibacillus choshinensis*. The method of introducing the expression vector into the *Brevibacillus choshinensis* of the invention is not also specifically limited, for which any method known to those skilled in the art may be suitably selected. One preferred method is an electroporation method generally used for introduction of an expression vector into *Brevibacillus choshinensis*.

Protein production using the resulting transformant may be attained by inoculating the transformant into a suitable medium, cultivating it therein, and after the cultivation, recovering and purifying the produced protein.

The culture condition for the *Brevibacillus choshinensis* transformant of the invention may be any and every one, not specifically limited, that enables cultivation of the transformant and expression of the recombinant protein gene. As an especially preferred example, the transformant is cultivated in a TM medium (peptone 1%, meat extract 0.5%, yeast extract 0.2%, glucose 1%, pH 7.0) or a 2SL medium (peptone 4%, yeast extract 0.5%, glucose 2%, pH 7.2) as used in Examples given in this description, at 30° C. for 2 to 4 days.

If desired, inorganic salt(s) such as iron sulfate, manganese sulfate and zinc sulfate may be suitably added to the culture medium.

When the recombinant protein is secreted and produced, then the produced recombinant protein may be recovered by separating the culture supernatant that contains the secreted and produced protein from the cultivated *Brevibacillus choshinensis* cells in any ordinary method of centrifugation, filtration or the like after the cultivation.

When the produced protein is not secreted but is accumulated in the *Brevibacillus choshinensis* cells, then the protein accumulated and produced in the cells may be recovered in any method known to those skilled in the art. For example, the cells are collected from the culture liquid according to a method of centrifugation, filtration or the like, then the cells are disrupted according to an ultrasonication method or a French press method, and if desired, the disrupted cells are solubilized with a surfactant added thereto, and the protein accumulated and produced in the cells is thereby recovered.

For purifying the produced protein, any method known to those skilled in the art may be employed. For example, solvent extraction, ultrafiltration, ammonium sulfate precipitation, gel filtration chromatography, ion-exchange chromatography, affinity chromatography, hydrophobic chromatography, electrophoresis, isotonic point precipitation and the like may be suitably employed either singly or as combined.

EFFECTS OF THE INVENTION

The *Brevibacillus choshinensis* of the invention can be utilized as a host in protein production through genetic recombination.

The invention provides *Brevibacillus choshinensis* of which the extracellular proteolytic activity has been much more reduced than that of known strains. When the *Brevibacillus choshinensis* is used as a host in production of a recombinant protein that is secreted and produced, then it significantly inhibits the decomposition of the recombinant protein due to extracellular proteolytic activity. Accordingly, the *Brevibacillus choshinensis* enables more efficient secretion production of recombinant protein than known *Brevibacillus choshinensis*.

The invention also provides *Brevibacillus choshinensis* of which the intracellular proteolytic activity has been much more reduced than that of known strains. When the *Brevibacillus choshinensis* is used as a host in production of a recombinant protein that is accumulated and produced inside the cells, then it significantly inhibits the degradation of the recombinant protein due to intracellular proteolytic activity. Accordingly, the *Brevibacillus choshinensis* enables more efficient intracellular accumulation and production of recombinant protein than known *Brevibacillus choshinensis*.

In addition, the invention provides *Brevibacillus choshinensis* not forming spores. Since the *Brevibacillus choshinensis* is completely killed under mild sterilization conditions, it is usable as a host in recombinant protein production for broad-range industrial applications such as production of recombinant protein pharmaceuticals.

Accordingly, the *Brevibacillus choshinensis* of the invention is extremely useful as a host in protein production through genetic recombination. One of the strains of the invention, HPD31-SP3 was internationally deposited (FERM BP-08479), and this strain is a novel triple-defective strain that satisfies all the above-mentioned three requirements.

The invention is described more concretely with reference to the following Examples, which, however, are not intended to restrict the scope of the invention.

EXAMPLES

Example 1

Preparation of *Brevibacillus choshinensis* Mutant not Having Sporulation Ability

*Brevibacillus choshinensis* HPD31 (FERM BP-1087) (FERM BP-6863) was mutated with a mutagen, nitrosoguanidine so as to obtain a *Brevibacillus choshinensis* mutant not having the ability to form spores.

First, *Brevibacillus choshinensis* HPD31 was cultivated overnight in a TM liquid medium (peptone 1%, meat extract 0.5%, yeast extract 0.2%, glucose 1%, pH 7.0) at 30° C. After the cultivation, the cell were recovered through centrifugation, and the recovered cells were washed and diluted with sterilized water so as to have OD of 0.1. Next, N-methyl-N'-nitro-N-nitrosoguanidine was added to the cells to be in an amount of 100 mg/liter, and the cells were thereby mutated with shaking to have a survival ratio of from 1 to 10%.

Next, the mutated cells were suitably diluted with sterilized water, and then spread on a TM plate medium and cultivated thereon at 30° C. for 3 days to thereby form their colonies on the TM plate medium. The strains having formed colonies with no surface wrinkles, different from the colonies of ordinary *Brevibacillus choshinensis*, were selected, and from the thus-selected strains, those having no spores in microscopic observation were selected as the strains not having the ability to form spores. The process of mutation treatment and colony formation was repeated, in which five mutants having the possibility of not forming spores were obtained.

Example 2

Evaluation of Sporulation Ability in Heat-Resistance Test of Mutants

Five mutants obtained in Example 1 were evaluated for their sporulation ability in a heat-resistance test. As a control in the test, used was *Brevibacillus choshinensis* HPD31.

*Brevibacillus choshinensis* HPD31 and five mutants (No. 1 to No. 5) were separately applied to a TM-agar medium and cultivated in a mode of stationary cultivation at 30° C. for 7 days. The cultivation term is 7 days and is longer than an ordinary one for sporulation. After the cultivation, the cells were suspended in 0.8% NaCl-containing sterilized distilled water so as to have an absorbance at 660 nm of 1.0, and 100 μl of the cell suspension was kept warmed at 80° C. for 10 minutes, and then applied to a TM-agar medium. Further, this was cultivated at a constant temperature of 30° C. for 24 hours, and the number of the living cells was counted from the number of the growing colonies.

Before the heat treatment at 80° C., the cell suspension was stepwise diluted with sterilized distilled water, and applied to a TM-agar medium and cultivated at a constant temperature of 30° C. for 24 hours. After the cultivation, the number of the living cells was counted from the number of the growing colonies. The results are shown in Table 1.

TABLE 1

| | Number of Living Cells | |
|---|---|---|
| Strain | before heated at 80° C. | after heated at 80° C. |
| *Brevibacillus choshinensis* HPD31 | $3.3 \times 10^7$ | $1.9 \times 10^7$ |
| *Brevibacillus choshinensis* mutant No. 1 | $4.3 \times 10^6$ | 0 |
| *Brevibacillus choshinensis* mutant No. 2 | $1.7 \times 10^7$ | 0 |
| *Brevibacillus choshinensis* mutant No. 3 | $2.6 \times 10^6$ | 0 |
| *Brevibacillus choshinensis* mutant No. 4 | $6.5 \times 10^6$ | 0 |
| *Brevibacillus choshinensis* mutant No. 5 | $8.1 \times 10^6$ | 0 |

Table 1 shows that only about ½ of all the living cells of *Brevibacillus choshinensis* HPD31 died when heated at 80° C. for 10 minutes, while those of *Brevibacillus choshinensis* mutants No. 1 to No. 5 completely died under the same condition. In other words, this significantly suggests that the mutants do not form heat-resistant spores.

Example 3

Determination of D Value of Mutants

Next, the cells of *Brevibacillus choshinensis* mutants No. 1 to No. 5 were tested to determine their D value. As a control in the test, used was *Brevibacillus choshinensis* HPD31.

*Brevibacillus choshinensis* HPD31 and *Brevibacillus choshinensis* mutants No. 1 to No. 5 were separately applied to a TM-agar medium and cultivated in a mode of stationary cultivation at 30° C. for 7 days. After the cultivation, the cells were suspended in a 0.8% sterilized saline solution so as to have an absorbance at 660 nm of 1.0. Kept warmed at different temperatures of 60° C., 70° C. and 80° C., the suspension was sampled out at different times of 1 minute, 2 minutes, 3 minutes, 5 minutes, 10 minutes, 20 minutes, 30 minutes and 60 minutes after the start of the warming. The samples from each suspension were cooled, and then separately applied to a TM-agar medium and cultivated at 30° C. for 24 hours. After the cultivation, the number of the cells was counted from the number of the growing colonies. Further, the D value of the cells was obtained from the number of the cells thus determined, and this indicates the time taken for reducing the number of the spores to ⅒.

In general, the living cells (non-spore cells) of *Brevibacillus choshinensis* immediately die within a temperature range of 60° C. and higher, and the cells having still remained in 1 minutes after the start of the test are presumed to be all spores, and on the basis of this presumption, the data computed herein. The results are shown in Table 2.

TABLE 2

| | D Value (minute) | | |
|---|---|---|---|
| Strain | 60° C. | 70° C. | 80° C. |
| *Brevibacillus choshinensis* HPD31 | 330 | 94 | 67 |
| *Brevibacillus choshinensis* mutant No. 1 | ND | ND | ND |
| *Brevibacillus choshinensis* mutant No. 2 | ND | ND | ND |
| *Brevibacillus choshinensis* mutant No. 3 | ND | ND | ND |
| *Brevibacillus choshinensis* mutant No. 4 | ND | ND | ND |
| *Brevibacillus choshinensis* mutant No. 5 | ND | ND | ND |

ND: not detected (shorter than 1 minute)

As in Table 2, *Brevibacillus choshinensis* HPD31 had the D value of their cells at different temperatures. However, since all the cells of *Brevibacillus choshinensis* mutants No. 1 to No. 5 died at the temperatures within 1 minute after the start of the test, and their D value could not be determined at the temperatures. It is understood that the results were brought about owing no sporulation of any of all *Brevibacillus choshinensis* mutants No. 1 to No. 5.

The test at a constant temperature of 80° C. for 10 minutes and the test for measurement of D value mentioned above confirm that *Brevibacillus choshinensis* mutants No. 1 to No.

5 all do not have the ability to form spores and completely die when kept at 60° C. for 1 minute.

Example 4

Production of Recombinant Protein (hEGF) Using Mutants No. 1 to No. 5 as Host

*Brevibacillus choshinensis* mutants No. 1 to No. 5 were tested for their recombinant protein producibility in production of recombinant hEGF. The process and the results are shown below. As a control, used was *Brevibacillus choshinensis* HPD31.

*Brevibacillus choshinensis* HPD31 and its mutants No. 1 to No. 5 were transformed by introducing thereinto a human epidermal growth factor (hEGF) expression plasmid vector pHT110-EGF (JP-A 6-133782 (1994)) according to an electroporation method. Next, the resulting transformants were separately cultivated in 3 ml of a 2SL liquid medium (peptone 4%, yeast extract 0.5%, glucose 2%, pH 7.2) with shaking at 30° C. for 60 hours. The mutants No. 4 and No. 5 did not form transformant.

After the cultivation, the culture liquid was centrifuged, and the supernatant fraction was diluted 10-fold with distilled water and then subjected to HPLC analysis. From the peak area thus obtained, the amount of the recombinant hEGF secreted and produced in the culture liquid was computed. The results are shown in Table 3. In Table 3, the amount of hEGF produced by *Brevibacillus choshinensis* HPD31 is 100%, and the data of the other hosts are relative values to it.

TABLE 3

| Host Strain | Relative Production of hEGP (%) |
| --- | --- |
| *Brevibacillus choshinensis* HPD31 | 100 |
| *Brevibacillus choshinensis* Mutant No. 1 | 119 |
| *Brevibacillus choshinensis* Mutant No. 2 | 40 |
| *Brevibacillus choshinensis* Mutant No. 3 | 20 |

As in Table 3, the production of hEGF in the case where *Brevibacillus choshinensis* mutant No. 1 was used as a host was higher in some degree than in the case where *Brevibacillus choshinensis* HPD31 was used. The growth and the transformation efficiency of the mutant were on the same level as that of HPD31.

The mutant No. 1 was named *Brevibacillus choshinensis* HPD31-SP1.

Example 5

Identification of Mutation Gene of *Brevibacillus choshinensis* HPD31-SP1

The gene mutated on the genome of *Brevibacillus choshinensis* HPD31-SP1 was identified. The identification of the mutated gene was carried out as follows: A genome library of *Brevibacillus choshinensis* HPD31 was prepared, and each fragment of the genome library was introduced into *Brevibacillus choshinensis* HPD31-SP1 and the strains whose sporulation ability was restored were selected.

A genome library of *Brevibacillus choshinensis* HPD31 was prepared according to the following process. First, a genome DNA was prepared from *Brevibacillus choshinensis* HPD31 cultivated for 15 hours in a TM medium, and then the genome DNA was partially processed with a restriction endonuclease Sau3AI to obtain genome DNA fragments. The resulting genome DNA fragments were ligated to plasmid vector pNY301 that had been processed with a restriction endonuclease BamHI, to thereby form genome library plasmid DNAs. Further, the genome library plasmid DNAs were introduced into *Brevibacillus choshinensis* HPD31-SP1 according to an electroporation method.

Next, the transformants of *Brevibacillus choshinensis* HPD31-SP1 with the genome library plasmid DNAs introduced thereinto were cultivated in a TM liquid medium (not containing antibiotic) at 30° C. for 1 hour, and further in a neomycin-containing TM liquid medium at 30° C. for 3 days. After the cultivation, these were heated at 80° C. for 10 minutes and then applied to a TM-agar medium and cultivated thereon at 30° C. for 3 days. Through the cultivation, the strains having formed colonies were selected as those whose sporulation ability was restored.

As a result, 8 strains whose sporulation ability was restored were obtained. Next, the plasmid DNAs previously introduced thereinto were extracted from these 8 strains, and their DNA sequences were determined. As a result, it was confirmed that three of those 8 strains have a common translation frame that codes for a novel gene. From the result, it is presumed that the gene in the mutant *Brevibacillus choshinensis* HPD31-SP1 would have been inactivated by the treatment with the mutagen and the mutant would have lost its ability to form spores. The novel gene encoded by the common translation frame was named hos. Its DNA sequence is shown in SEQ ID NO: 1 (upper line in FIG. 7 and FIG. 8).

Next, using *Brevibacillus choshinensis* HPD31 as a parent strain, hos gene-inactivated strains were constructed, and it was confirmed that *Brevibacillus choshinensis* loses its sporulation ability through inactivation of the hos gene.

The hos gene-inactivated strains were constructed according to a method similar to known homologous recombination. Its concrete process is shown below.

First, a vector for hos gene inactivation was constructed. According to PCR using primers Hos P1 and Hos P2, a DNA fragment in the upstream part of a hos gene (1.5 kbp, with a recognition sequence KpnI introduced into the upstream side and a recognition sequence BamHI into the downstream side) was amplified, and then the DNA fragment of 1.5 kbp that had been amplified through the PCR was processed with restriction endonucleases KpnI and BamHI, and the resulting DNA fragment was recovered. On the other hand, according to PCR using primers Hos P3 and Hos P4, a DNA fragment of about 1.5 kpb in the downstream part of the hos gene (having a recognition sequence PstI introduced into the upstream side and a recognition sequence XbaI introduced into the downstream side) was amplified, and then the DNA fragment of about 1.5 kbp was processed with restriction endonucleases PstI and XbaI, and the resulting DNA fragment was recovered. A DNA fragment having a neomycin-resistant gene and having an FRT sequence (Gene, 212, 77-86 (1998)) on both sides (1.4 kbp) was processed with restriction endonucleases BamHI and PstI, and the resulting DNA fragment was recovered.

An erythromycin-resistant gene-containing DNA fragment that had been cut out with a restriction endonuclease SacI was inserted into a vector pBluescript®II SK+ (Toyobo Co., Ltd.) not replicable in *Brevibacillus choshinensis*, at its SacI recognition sequence. Next, the above-mentioned three DNA fragments were introduced into the KpnI/XbaI restriction endonuclease cleavage site of the plasmid DNA, all at a time thereinto, and a vector for hos gene inactivation was thus constructed. The thus-constructed, hos gene inactivation vector is referred to as pBlue-hos::Nm$^r$. The base sequences of the primers Hos P1, Hos P2, Hos P3 and Hos P4 used in the above are shown as SEQ ID NO:7, NO:8, NO:9 and NO:10, and these are all shown in FIG. 14.

Next, the hos gene inactivation vector pBlue-hos::Nm$^r$ was introduced into *Brevibacillus choshinensis* HPD31 according to an electroporation method, the resulting transformants were selected based on their neomycin resistance as an index. Further, the neomycin-resistant strains were applied to an erythromycin-containing TM-agar medium and cultivated thereon at 30° C. for 2 days, and a strain was selected based on its sensitivity to erythromycin as an index. The hos gene inactivation in the thus-selected strain was confirmed through PCR and genomic Southern analysis. Further, according to the process described in Example 7 below, the neomycin-resistant gene was deleted from the hos gene-inactivated strain, and a hos gene-inactivated strain of *Brevibacillus choshinensis* was thus obtained.

Next, the hos gene-inactivated strain was tested for its sporulation ability, according to the process of Examples 2 and 3, and it was confirmed that the strain do not have the ability to form spores.

Further, the hos gene-inactivated strain was tested for its producibility of recombinant protein according to the process of Example 4, and it was confirmed that its producibility of hEGF is on the same level as that of *Brevibacillus choshinensis* HPD31-SP1.

From the test results, the conclusion is that, in the *Brevibacillus choshinensis* HPD31-SP1, the hos gene was mutated through the treatment with the mutagen and was therefore inactivated, and as a result, the mutant lost its sporulation ability.

Construction of *Brevibacillus choshinensis* of which the Intracellular Major Protease Gene was Inactivated:

Example 6

Cloning of Intracellular Major Protease Gene Imp (6-1) Cloning of Imp:

For identifying the protease to be inactivated, the intracellular major protease gene of *Brevibacillus choshinensis* HPD31 (FERM BP-1087) was cloned.

With the genome library plasmid DNAs of *Brevibacillus choshinensis* HPD31s that had been constructed according to the process of Example 5, *Brevibacillus choshinensis* HPD31s were transformed, and the resulting transformants were applied to a TM-agar medium containing 1% skim milk and 50 µg/ml (as final concentration) of neomycin, and cultivated thereon at 30° C. for 4 days. After the cultivation, the strains having formed halos that indicate the decomposition of skim milk were selected.

Further, the plasmid DNA was extracted out from the strains obtained in the above, and the DNA sequence was determined. As a result, a translation frame (ORF) of about 1.4 kbp existed in the *Brevibacillus choshinensis* HPD31 genome-derived 3.6 kbp DNA fragment, and ORF of about 0.7 kbp existed in the complementary sequence of the DNA fragment. The plasmid that contains the DNA fragment of about 3.6 kbp is named pNY-imp.

Of the two ORF's contained in the 3.6 kbp DNA fragment, a plasmid containing only the ORF of about 1.4 kbp and a plasmid containing only the ORF of about 0.7 kbp were constructed, and using each of these plasmids, *Brevibacillus choshinensis* HPD31 was transformed.

Further, the resulting transformants were separately cultivated on a 1% skim milk-containing TM-agar medium, whereupon the transformant that contains the plasmid having the ORF of about 1.4 kbp alone formed halo on the TM-agar medium. From this, it is obvious that the ORF of about 1.4 kbp encodes a protease. The protease encoded by the ORF of about 1.4 kbp is named intracellular major protease, abbreviated to IMP. Amino acid sequence homology search was carried out between IMP and other known proteins, but no protein with significant homology to IMP was found.

The DNA base sequence of the *Brevibacillus choshinensis* HPD31 strain-derived intracellular major protease gene imp is shown as SEQ ID NO:5 (upper line in FIG. 12 and FIG. 13); and the amino acid sequence of the intracellular major protease IMP corresponding to the DNA sequence is shown as SEQ ID NO: 6 (lower line in FIG. 12 and FIG. 13).

(6-2) Expression of Imp Gene and Purification of Imp Protein:

Next, for clarifying the details of the properties of IMP, expression of the imp gene and purification of the IMP protein were carried out.

First, for the purpose of facilitating the purification of the produced IMP protein, constructed was a plasmid vector pNY-imp-His which expresses a polypeptide with a peptide tag of 8 histidines (histidine tag) added to the C-terminus of IMP. The plasmid vector pNY-imp-His was constructed according to the following process.

First, using a sense primer imp P1 and an antisense primer imp P2, PCR was carried out with a pNY-imp plasmid DNA as a template. The sense primer imp P1 is a primer homologous to the DNA sequence that codes for the amino acid sequence presumed to be the N-terminus of IMP. The antisense primer imp P2 is a primer constructed by adding a DNA sequence of 8-fold repetition of gtg for encoding the histidine tag and further introducing a stop codon and a restriction endonuclease EcoRI recognition sequence thereinto. The base sequence of the sense primer imp P1 is shown as SEQ ID NO: 11; and the base sequence of the antisense primer imp P2 is shown as SEQ ID NO: 12; and these are all shown in FIG. 15.

The DNA fragment that contains the PCR-amplified, histidine tag-encoding sequence and the imp gene was purified, and then processed with restriction endonucleases XhoI and EcoRI to obtain a DNA fragment of about 500 bp. Next, this DNA fragment was inserted into the XhoI/EcoRI restriction endonuclease cleavage site of the plasmid pNY-imp to obtain a plasmid vector pNY-imp-His.

Next, *Brevibacillus choshinensis* HPD31 was transformed with the above-obtained plasmid vector pNY-imp-His, and the resulting transformant was cultivated with shaking in 600 ml of a TM liquid medium at 30° C. for 48 hours. After the cultivation, the cells were recovered through centrifugation at 6000×g, and suspended in 30 ml of a washing buffer solution (20 mM phosphate, pH 7.4, 2 M KCl), and then again recovered through centrifugation at 6000×g. This washing operation was repeated two times, and then the cells were suspended in a 30 mM lysis buffer solution (20 mM phosphate, pH 7.4) that contains 0.2 mg/ml of lysozyme and 10 units of DNase, and kept at a constant temperature of 37° C. for 20 minutes. Next, the cells were disrupted by ultrasonication and centrifuged at 34000×g for 30 minutes, and the supernatant was recovered as an intracellular fraction. 30 ml of the intracellular fraction was filtered through a 0.22-µm filter, to which were added 0.5 M, as final concentration, NaCl and 10 mM imidazole. Then, this was applied to a 1-ml nickel-chelate column (Amersham Pharmacia Co.). At a linear concentration gradient of from 10 to 50 mM imidazole, the IMP protein having adsorbed to the nickel-chelate column was eluted and collected. The protease activity of the eluate fractionated with a protease assay kit, QuantiCleave® (Pierce Biotechnology, Inc.) was determined, and the IMP active fraction was thereby identified. Further, 5 μl of the active fraction was subjected to SDS-PAGE, which confirmed that the IMP protein was purified to a level of a single substance in electrophoresis.

(6-3) Properties of IMP:

A pure enzyme preparation of IMP that contains 10 μg of IMP was subjected to SDS-PAGE using an acrylamide concentration of 10%, and the separated protein was transferred onto a PVDF film in a semi-dry protein transfer device, in which the IMP protein band was detected with a staining solution comprising 0.01% CBB (Coomassie brilliant blue) and 40% methanol. Next, the PVDF film was discolored with a CBB-free 40% methanol solution, and then the film was dried. Next, the IMP protein band was cut out of the film, and analyzed the N-terminal amino acid sequence thereof. This confirmed that the N-terminal sequence of the protein is MetAsnH is ProAsp. From the above, it was found that IMP is an intracellular protease comprising 453 amino acid residues and having an estimated molecular weight of 49,811 Da.

Next, using the protease assay kit, QuantiCleave® (Pierce Biotechnology, Inc.), the pure IMP was analyzed in detail for its enzymochemical properties. 2 mg of a substrate, succinylated casein was dissolved in 65 μl of 100 mM borate buffer solution (pH 8.0) to prepare an enzyme substrate solution, to which was added 10 μl of a pure enzyme preparation containing 1.5 μg of IMP, and this was kept at a constant temperature of 37° C. for 20 minutes. Next, 25 μl of a color developer solution was added to it and kept at room temperature for 20 minutes. After color development, the absorbance of the liquid at 450 nm was measured, by which the IMP proteolytic activity was determined. In the determination of the IMP proteolytic activity, the enzyme amount that increases the absorbance at 450 nm by 0.1 through the reaction at 30° C. for 60 minutes is 1 unit. The amount of the enzyme protein used for the reaction was determined according to the Bradford method using BSA as a standard substance.

From the results, it has become clear that the optimum temperature of IMP is 30° C., the optimum pH thereof is 8.0, the relative activity thereof is 44.7 units/mg protein, and at least 1 mM of EDTA inhibits the activity of IMP.

Example 7

Construction of Brevibacillus choshinensis in which the Intracellular Major Protease Gene Imp was Inactivated Next, using Brevibacillus choshinensis HPD31-SP1 as a parent strain, constructed was Brevibacillus choshinensis in which the imp gene was inactivated. For constructing the Brevibacillus choshinensis in which the imp gene was inactivated, employed was a method similar to the method of gene inactivation through homologous recombination. Concretely, the process is as follows:

First, a vector for imp gene inactivation was constructed. With a restriction endonuclease EcoRV, a DNA fragment of 1 kbp was cut out from an imp gene, which is the inner region of the imp gene, and this was inserted into the SmaI/EcoRV restriction endonuclease cleavage site of a plasmid vector pBluescript®II SK+ (Toyobo Co., Ltd.). Next, this was processed with a restriction endonuclease PstI to remove a region of 120 bp inside the imp gene. Then, a DNA fragment containing a neomycin-resistant gene and having an FRT sequence on both ends was inserted into the PstI restriction endonuclease cleavage site, and the imp gene was thereby cleaved. Further, an erythromycin-resistant gene-containing DNA fragment that had been cut out with a restriction endonuclease BamHI was inserted into the BamHI restriction endonuclease cleavage site of the plasmid to thereby construct a vector for imp gene inactivation. The thus-constructed imp gene inactivation vector is referred to as pBlue-imp::Nm$^r$.

Next, 1 μg of the imp gene inactivation vector pBlue-imp::Nm$^r$ was inserted into Brevibacillus choshinensis HPD31-SP1 according to an electroporation method, and the transformant was selected based on the neomycin resistance as an index. The resulting neomycin-resistant strain was applied to a TM-agar medium (peptone 1%, meat extract 0.5%, yeast extract 0.2%, glucose 1%, agar 1.5%, pH 7.0) containing 1 μg/ml (as final concentration) of erythromycin, and cultivated thereon at 30° C. for 2 days, and a strain having underwent homologous recombination at two gene loci in the upstream and downstream regions of the imp gene (double crossover strain) was selected based on the sensitivity to erythromycin as an index. Further, the thus-selected strain was subjected to PCR and genomic Southern analysis, which confirmed that the imp gene in the strain was inactivated.

Next, the neomycin-resistant gene was deleted from the genome of the imp gene-inactivated strain constructed in the above. For deleting the neomycin-resistant gene from the imp gene-inactivated strain, first constructed was a plasmid vector for neomycin-resistant gene deletion that has an yeast-derived Flp recombinase gene and a bleomycin-resistant gene, according to the process mentioned below.

First, prior to cultivating the strain in a neomycin-free medium, a plasmid vector pNY301 (JP-A 10-295378 (1998)) was processed with a chemical, hydroxylamine to give a mutant of the strain, for the purpose of obtaining a plasmid vector that could be readily removed from the cells of the Brevibacillus choshinensis strain. Concretely, the process is as follows:

1.5 μg of a plasmid vector DNA of pNY301 was dissolved in a solution (100 μl) prepared by dissolving 350 mg of hydroxylamine and 90 mg of NaOH in 5 ml of ice-cooled, sterilized distilled water, and kept at a constant temperature of 70° C. for 120 minutes, and then the plasmid DNA was concentrated through ethanol precipitation and dried. Next, the plasmid DNA was dissolved in sterilized distilled water, with which Brevibacillus choshinensis HPD31 was transformed. The amount of the plasmid DNA used for the transformation was 100 ng. Based on the neomycin resistance thereof, the intended transformant was selected. In the case of the plasmid DNA obtained from the transformant that had grown slowly and formed small colonies, the number of copies/cell thereof was reduced to one a few tenths as compared with that of the transformant obtained by using the original pNY301 plasmid vector DNA; and when the transformant was cultivated in a neomycin-free medium, then the plasmid DNA was readily removed from the transformant cells.

Using the plasmid DNA as a template, and using a sense primer flp P1 with an EcoRI recognition sequence and a PstI recognition sequence added thereto (SEQ ID NO: 13, FIG. 16) and an antisense primer flp P2 with a BamHI recognition sequence added thereto (SEQ ID NO: 14, FIG. 17), PCR was carried out to thereby amplify a DNA fragment of about 1.6 kbp that contains a rep gene. Next, the DNA fragment of about 1.6 kbp was processed with restriction endoucleases EcoRI and BamHI.

Using a bleomycin-resistant gene-having plasmid pNH300 (Yasuhiro Shiga, et al., Applied and Environmental Microbiology, 58, 525-531 (1992)) as a template, and using a sense primer flp P3 with a BglII recognition sequence added thereto (SEQ ID NO: 15, FIG. 18) and an antisense primer flp P4 with an EcoRI recognition sequence and a XbaI recognition sequence added thereto (SEQ ID NO: 16, FIG. 19), PCR was carried out to thereby amplify a DNA fragment of about 1.1 kbp that contain both a bleomycin-resistant gene and a plasmid Ori. Next, the DNA fragment of about 1.1 kbp was processed with restriction endonucleases EcoRI and BallI, and the two DNA fragments of about 1.6 kbp and about 1.1 kbp obtained in the above were bound to construct a new plasmid. This plasmid is referred to as pNY-Mut-Ble.

On the other hand, using an yeast-derived plasmid 2-μm as a template, and using a sense primer flp P5 with an NcoI recognition sequence added thereto (SEQ ID NO: 17, FIG. 20) and using an antisense primer flp P6 with an XhoI recognition sequence added thereto (SEQ ID NO:18, FIG. 21), PCR was carried out to thereby amplify a region containing an Flp recombinase gene. Next, the Flp recombinase gene-containing DNA fragment obtained in this PCR was processed with NcoI and XhoI, and then inserted into the NcoI/XhoI restriction endonuclease cleavage site of the vector pNY301 to obtain an Flp recombinase gene-containing vector. This vector is referred to as pNY301-Flp.

Next, using this pNY301-Flp as a template and using a sense primer flp P7 with an XbaI recognition sequence added thereto (SEQ ID NO:19, FIG. 22) and an antisense primer flp P8 with a PstI recognition sequence added thereto (SEQ ID NO: 20, FIG. 23), PCR was carried out to thereby amplify a DNA fragment of about 1.6 kbp that contains an Flp recombinase gene and a pNY301-derived promoter region. Next, this DNA fragment of about 1.6 kbp was processed with restriction endonucleases XbaI and PstI, and then inserted into the XbaI/PstI restriction endonuclease cleavage site of the plasmid pNY-Mut-Ble obtained in the above to thereby construct a vector for neomycin-resistant gene deletion. The neomycin-resistant gene deletion vector is referred to as pNY-Mut-Ble-Flp. This pNY-Mut-Ble-Flp is a plasmid vector that expresses an Flp recombinase gene, and when cultivated in a neomycin-free medium, it is readily removed from the cells of the *Brevibacillus choshinensis* strain.

Next, the neomycin-resistant gene deletion vector pNY-Mut-Ble-Flp was introduced into an imp gene-inactivated strain according to an electroporation method, and the resulting transformant was selected on the basis of bleomycin resistance as an index. Next, the transformant was cultivated by shaking in a bleomycin-free TM liquid medium, and then in a TM-agar medium. From the strains having formed colonies on the TM-agar medium, selected were those sensitive to both neomycin and bleomycin.

According to the process as above, the intended imp gene-inactivated strain of *Brevibacillus choshinensis* was obtained, in which the neomycin-resistant gene was deleted and the neomycin-resistant gene deletion vector pNY-Mut-Ble-Flp was removed. The *Brevibacillus choshinensis* strain in which the intracellular major protease gene imp on the genome was inactivated was named *Brevibacillus choshinensis* HPD31-SP2.

Construction of *Brevibacillus choshinensis* in which the intracellular and extracellular major protease genes were inactivated:

Next, the imp gene-inactivated *Brevibacillus choshinensis* HPD31-SP2 obtained in the above was processed for inactivating the extracellular major protease gene therein. First for this, the extracellular major protease was isolated and its gene was cloned.

Example 8

Cloning of Extracellular Major Protease (Abbreviated to Emp) Gene (8-1) Purification of Extracellular Major Protease (EMP):

*Brevibacillus choshinensis* HPD31 (FERM BP-1087) was cultivated in 5 liters of a TM liquid medium for 24 hours. After the cultivation, the culture supernatant was fractionated through centrifugation, and 50 mM (as final concentration) of Tris-HCl (pH 7.5) was added to it, and this was then subjected to DEAE anion-exchange column chromatography to eluate EMP with a linear concentration gradient of 0 to 0.6 M NaCl.

The EMP-containing fraction was dialyzed against a buffer of 50 mM Tris-HCl (pH 7.5), then applied to a heparin column and eluted with a linear concentration gradient of 0 to 0.5 M NaCl to obtain a pure EMP preparation. The enzymatic activity of each eluate fraction was determined through gelatin-PAGE according to the method in Analytical Biochemistry, 102, 196-202 (1980).

(8-2) EMP Amino Acid Sequence Analysis:

8-2-1: N-Terminal Amino Acid Sequence Analysis:

10 μg of the pure EMP preparation was subjected to SDS-PAGE using an acrylamide concentration of 10%, and the separated protein was transferred onto a PVDF film in a semi-dry protein transfer device, in which the EMP protein band was detected with a staining solution comprising 0.01% CBB and 40% methanol. Next, the PVDF film was discolored with a CBB-free 40% methanol solution, and then the film was dried. Next, the protein band-containing part was cut out of the film, and analyzed for the N-terminal amino acid sequence thereof by the use of an ABI protein sequencer Model 492. This amino acid sequence analysis confirmed the N-terminal amino acid sequence of the protein, comprising 24 amino acid residues of AlaSerLysArgValHisThrAspAsn-LeuValIleAlaLeuValGluPheAsnAspLeuGluGlyAsn Gln (SEQ ID NO: 40).

8-2-2: Internal Partial Amino Acid Sequence Analysis:

50 μg of the pure EMP preparation was subjected to SDS-PAGE using an acrylamide concentration of 10%, and an EMP protein band-containing gel fraction was cut out. Next, according to the method in Current Protocols in Protein Science, 11.3 Digestion of Proteins in Gel for Sequence Analysis, John Wiley & Sons, 1995, the EMP was subjected to in-gel enzyme treatment with 1 μg of trypsin for limited digestion thereof in gel. Next, the peptide fragment of the trypsin-processed EMP was recovered in an acetonitrile solution, and then subjected to reversed-phase column chromatography with Mightysil Aqua PR18 (Kanto Kagaku Co.), in which the peptide fragment of EMP was eluted and separated with a linear concentration gradient of 0 to 60% acetonitrile containing 0.05% TFA. Then, the thus eluted and separated EMP peptide fragment was dried to solidness, and one peptide fragment was subjected to amino acid sequence analysis with an ABI protein sequencer Model 492. The amino acid sequence analysis confirmed the internal partial amino acid sequence comprising 10 amino acid residues of IlePheGlnThrGlnProThrGlyPheAsp (SEQ ID NO:41).

(8-3) Cloning and Identification of Emp Gene:

Next, based on the internal partial amino acid sequence data of EMP obtained in the above, two oligonucleotide primers emp P1 and emp P2 were designed and synthesized. The base sequence of emp P1 is shown as SEQ ID NO: 21; and the base sequence of emp P2 is as SEQ ID NO:22. The base sequences of emp P1 and emp P2 and the amino acid sequences corresponding to the base sequences of emp P1 and emp P2 are all shown in FIG. 24. The 6th "n" from the left in the sequence of SEQ ID NO: 21 and the 6th "n" from the left in the sequence of SEQ ID NO: 22 are inosine.

Using these primers emp P1 and emp P2, PCR was carried out with the genome DNA of *Brevibacillus choshinensis* HPD31 as a template, and a DNA fragment of about 700 bp was thereby amplified. Next, the DNA fragment of about 700 bp was subcloned in the HincII recognition sequence of a vector pUC118 (Toyobo Co., Ltd.) for DNA sequence analysis thereof, which confirmed that the DNA fragment of about 700 bp contains a part of the emp gene.

Next, for the purpose of cloning a DNA fragment in the upstream region and a DNA fragment in the downstream region of the DNA fragment of about 700 bp, two specific primers mentioned below, an antisense primer emp P3 for amplification of the upstream region and a sense primer emp P4 for amplification of the downstream region, were designed and synthesized based on the DNA sequence data of the DNA fragment of about 700 bp obtained in the above.

The genome DNA of *Brevibacillus choshinensis* HPD31 was fragmented with a restriction endonuclease such as EcoRV, and an adaptor DNA was added to the terminal of the DNA fragments to prepare an adaptor genome DNA library of *Brevibacillus choshinensis* HPD31.

The base sequence of the antisense primer emp P3, that of the sense primer emp P4 and that of the adaptor DNA are shown as SEQ ID NO:23, NO:24 and NO:25, respectively. These are all shown in FIG. 25.

Next, PCR was carried out using the adaptor DNA library of the *Brevibacillus choshinensis* HPD31 genome as a template, thereby to amplify the DNA fragment containing the full length of the emp gene. Further, the DNA sequence of the emp gene was determined through direct sequencing of the resulting PCR-amplified product.

The DNA sequence of the *Brevibacillus choshinensis* HPD31 strain-derived extracellular major protease gene emp is shown as SEQ ID NO: 3 (upper line in FIGS. 9 to 11). The amino acid sequence of the extracellular major protease EMP corresponding to the DNA sequence is shown as SEQ ID NO: 4 (lower line in FIGS. 9 to 11).

(8-4) Properties of EMP:

The extracellular major protease EMP is an acidic protein comprising 754 amino acid residues as a prepro structure and having a molecular weight of about 84 kDa, and it is presumed that, when extracellularly secreted, its N-terminal of 124 amino acid residues may be cut off and it is matured into a structure comprising 630 amino acid residues and having a molecular weight of about 71 kDa. On the 207th position from the N-terminal of the matured protein, there exists an HEXXH sequence that may participate in the coordination of the zinc ion of a Zinc metalloprotease. Accordingly, it is presumed that EMP would be a Zinc metalloprotease.

EMP has 37% homology to the metalloprotease of *Clostridium acetobutylicum* on the amino acid level.

Example 9

Construction of *Brevibacillus choshinensis* Strain in which the Imp Gene and the Emp Gene were Inactivated Next, the emp gene was inactivated in the *Brevibacillus choshinensis* HPD31-SP2 obtained in Example 7, as a parent strain, to thereby produce a *Brevibacillus choshinensis* strain in which two protease genes imp and emp were inactivated. For producing the *Brevibacillus choshinensis* strain in which the emp gene was inactivated, employed was a method similar to the gene inactivation method through homologous recombination.

First, a vector for emp gene inactivation was constructed. Using the emp P4 primer (SEQ ID NO:24) and the adaptor primer (SEQ ID NO:25) described in Example 8-3, and using the adaptor genome DNA library of *Brevibacillus choshinensis* HPD31 as a template, PCR was carried out to thereby amplify a DNA fragment of about 2.2 kbp containing a part of the emp gene.

Next, the DNA fragment of about 2.2 kbp amplified by PCR was inserted into the HindIII restriction endonuclease cleavage site of pUC118. Next, an erythromycin-resistant gene-containing DNA fragment that had been cut out with a restriction endonuclease BamHI was inserted into the BamHI recognition sequence near the inserted DNA fragment. Next, a part of 220 bp inside the emp gene was removed with restriction endonucleases HindIII and PstI, and then a DNA fragment containing a neomycin-resistant gene and having an FRT sequence on both sides was inserted into the HindIII/PstI restriction endonuclease cleavage site of the plasmid, thereby constructing a vector for emp gene inactivation. The emp gene inactivation vector is referred to as pBlue-emp::Nm$^r$.

Next, using the emp gene inactivation vector pBlue-emp::Nm$^r$, the emp gene of *Brevibacillus choshinensis* HPD31-SP2 was inactivated. The inactivation of the emp gene with the pBlue-emp::Nm$^r$, and the removal of the neomycin-resistant gene from the emp gene-inactivated strain genome were effected according to the same process as that for construction of the imp gene-inactivated strain in Example 7.

The *Brevibacillus choshinensis* strain obtained in the above, in which the imp gene and the emp gene were inactivated, was named *Brevibacillus choshinensis* HPD31-SP3, and this was internationally deposited as FERM BP-08479.

Confirmation of the Absence of Sporogenous Capability of *Brevibacillus choshinensis* HPD31-SP3:

Example 10

Heat-Resistance Test

To confirm the fact that the *Brevibacillus choshinensis* HPD31-SP3 obtained in the above does not have the ability to form spores, the strain was tested for its heat resistance in the same manner as in Example 2. As a control in the test used was *Brevibacillus choshinensis* HPD31. The results are shown in Table 4.

TABLE 4

| | Number of Living Cells | |
|---|---|---|
| Strain | before heated at 80° C. | after heated at 80° C. |
| *Brevibacillus choshinensis* HPD31 | 7.6 × 10$^7$ | 1.9 × 10$^7$ |
| *Brevibacillus choshinensis* HPD31-SP3 | 2.1 × 10$^7$ | 0 |

About ¾ of all the living cells of *Brevibacillus choshinensis* HPD31 died when heated at 80° C. for 10 minutes, while all the living cells of *Brevibacillus choshinensis* completely died under the same condition. In other words, this shows that the latter does not form heat-resistant spores.

Example 11

Determination of D Value

Next, for analyzing *Brevibacillus choshinensis* HPD31-SP3 for its sporulation capability, the D value of the strain was determined in the same manner as in Example 3. As a control in the test, used was *Brevibacillus choshinensis* HPD31. The results are shown in Table 5.

TABLE 5

| Strain | D Value (minute) | | |
| --- | --- | --- | --- |
|  | 60° C. | 70° C. | 80° C. |
| *Brevibacillus choshinensis* HPD31 | 330 | 94 | 67 |
| *Brevibacillus choshinensis* HPD31-SP3 | ND | ND | ND |

ND: not detected (shorter than 1 minute)

As in Table 5, *Brevibacillus choshinensis* HPD31 had the D value of their cells at different temperatures. However, since all the cells of *Brevibacillus choshinensis* HPD31-SP3 died at the temperatures within 1 minute after the start of the test, and their D value could not be determined at the temperatures. It is understood that the results were brought about owing to no sporulation of *Brevibacillus choshinensis* HPD31-SP3.

The test at a constant temperature of 80° C. for 10 minutes and the test for measurement of D value mentioned above confirm that *Brevibacillus choshinensis* HPD31-SP3 does not have the ability to form spores.

Evaluation of Extracellular Protease Activity of *Brevibacillus choshinensis* HPD31-SP3:

The extracellular protease activity of *Brevibacillus choshinensis* HPD31-SP3 was evaluated.

First confirmed was the fact that *Brevibacillus choshinensis* HPD31-SP3 does not decompose milk casein and BSA which are not also decomposed by *Brevibacillus choshinensis* HPD31 (FERM BP-1087) (*Bacillus brevis* H102) (JP-A 63-56277 (1988)).

Example 12

Evaluation of Extracellular Protease Activity of *Brevibacillus choshinensis* HPD31-SP3 in Milk Casein Decomposition Test Cells of *Brevibacillus choshinensis* HPD31-SP3 were inoculated on a TM-agar plate medium containing 5%, 2% or 1% skim milk, and then cultivated thereon at 37° C. for 3 days to observe the presence or absence of halo formation around the colonies owing to milk casein decomposition. As a result, no halo formed at all in any TM-agar medium containing 5%, 2% or 1% skim milk.

The results confirm that *Brevibacillus choshinensis* HPD31-SP3 do not have the ability to decompose milk casein.

Example 13

Evaluation of Extracellular Protease Activity of *Brevibacillus choshinensis* HPD31-SP3 in BSA Decomposition Test Cells of *Brevibacillus choshinensis* HPD31-SP3 were inoculated into 10 ml of a TM liquid medium, to which 3.2 mg/ml (as final concentration) of a BSA (Sigma A4503) solution obtained by filtration for sterilization had been added, and cultivated therein with shaking at 37° C. at 200 rpm.

24 hours, 48 hours and 72 hours after the start of the cultivation, the culture filter was sampled, and each culture sample was centrifuged at 10000 rpm for 5 minutes. Next, 125 µl of 0.5 M Tris-HCl (pH 6.8), 200 µl of 10% SDS and 50 µl of β-mercaptoethanol were added to 625 µl of the culture supernatant fraction obtained through the centrifugation, then stirred, and heated in a boiling water for 3 minutes. After said heating, and then 0.1 ml of 0.0625 M Tris-HCl (pH 6.8) containing 0.05% BPB and 70% glycerol was added to it, and subjected to SDS-polyacrylamide gel electrophoresis (SDS-PAGE). SDS-PAGE was carried out at an acrylamide concentration of 10%. The protein detection was attained through staining with CBB (Coomassie brilliant blue). As a result, anytime in 24 hours, 48 hours and 72 hours after the start of the cultivation, no band to indicate BSA decomposition was found.

The results confirm that *Brevibacillus choshinensis* HPD31-SP3 do not have the ability to decompose BSA.

Further, the extracellular protease activity of *Brevibacillus choshinensis* HPD31-SP3 was evaluated according to a gelatin-PAGE method and a method using azocasein or azocoll. As a control in the test, used was *Brevibacillus choshinensis* HPD31 (FERM BP-1087).

Example 14

Evaluation of Extracellular Protease Activity of HPD31-SP3 in Gelatin-PAGE

Cells of *Brevibacillus choshinensis* HPD31 and those of *Brevibacillus choshinensis* HPD31-SP3 were separately cultivated in a TM liquid medium for 48 hours, and 10 µl of the culture supernatant fraction was subjected to gelatin-PAGE. The gelatin-PAGE was carried out according to the method in Analytical Biochemistry 102, 196-202 (1980). The gel after electrophoresis was put in 50 mM Tris-HCl buffer solution (pH 7.5) containing 10 mM CaCl$_2$, at a constant temperature of 37° C. for 16 hours, and gelatin in the gel was thereby decomposed. After said putting at the constant temperature, this was stained with a staining solution comprising 0.1% amide black, 30% methanol and 10% acetic acid for 30 minutes, and then discolored with the same solution but not containing amide black. The results are shown in FIG. 2.

Figure 2:
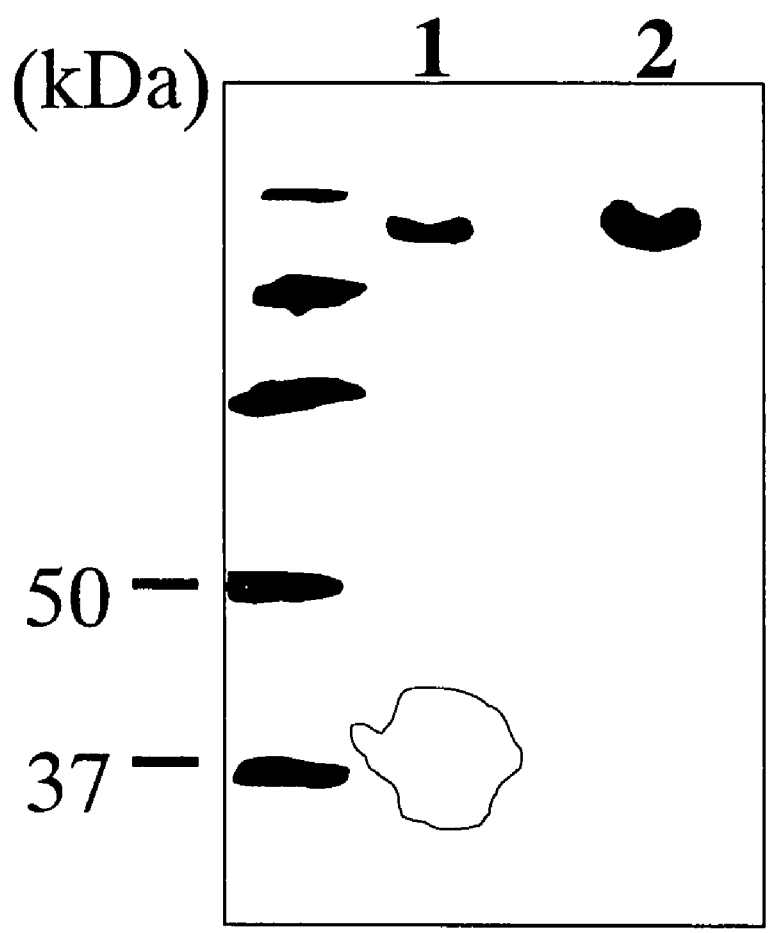
FIG. 2:
It is a drawing showing the results of measurement of the protease activity of each culture supernatant fraction of Brevibacillus choshinensis HPD31 (lane 1) and Brevibacillus choshinensis HPD31-SP3 (lane 2) through gelatin-PAGE (zymograph). Within the white frame, a clear band is shown resulting from the decomposition of gelatin by the protease activity.

As in FIG. 2, the culture supernatant fraction of *Brevibacillus choshinensis* HPD31 gave a clear band that shows gelatin decomposition owing to the proteolytic activity thereof at a mobility of about 40 kDa, but the culture supernatant fraction of *Brevibacillus choshinensis* HPD31-SP3 gave no clear band to indicate gelatin decomposition.

Example 15

Determination of Extracellular Protease Activity of HPD31-SP3 by the Use of Azocasein Cells of *Brevibacillus choshinensis* HPD31 and those of *Brevibacillus choshinensis* HPD31-SP3 were separately cultivated with shaking in a T2 medium (peptone 1%, meat extract 0.5%, yeast extract 0.2%, glucose 1%) at 30° C. for 6 days. The culture was centrifuged at 10,000 rpm for 10 minutes, and the resulting supernatant was used as a sample for activity determination. 5 g of azocasein was dissolved in 1 liter of 0.1 M Tris-HCl (pH 8.0) to prepare a substrate solution. Next, to 0.1 ml of the substrate solution, added was the same amount of the sample, and the two were reacted at 37° C. for 5 hours. Then, the reaction was stopped by adding 0.2 ml of 10% trichloroacetic acid solution added thereto. Next, this was statically kept at room temperature for 20 minutes, and then centrifuged at 15,000 rpm for 10 minutes to collect the supernatant fraction. 0.4 ml of 0.5 N NaOH was added to it, and its absorbance at 440 nm was measured. The test results are shown in Table 6. In Table 6, the enzyme activity to change the absorbance by 10 in the reaction for 5 hours is defined as 1 unit.

TABLE 6

| Strain | Enzyme Activity (units/ml of culture supernatant) |
|---|---|
| Brevibacilius choshinensis HPD31 | 0.12 |
| Brevibacillus choshinensis HPD31-SP3 | ND |

ND: not detected (at most 0.001).

As in Table 6 above, no protease activity was detected in the test of *Brevibacillus choshinensis* HPD31-SP3 with an azocasein reagent. The protease activity of the culture supernatant fraction of *Brevibacillus choshinensis* HPD31-SP3 is at most $1/120$ of that of the culture supernatant fraction of *Brevibacillus choshinensis* HPD31.

Example 16

Determination of Extracellular Protease Activity of HPD31-SP3 by the Use of Azocoll Cells of *Brevibacillus choshinensis* HPD31 and those of *Brevibacillus choshinensis* HPD31-SP3 were separately cultivated in a TM liquid medium for 48 hours. After the cultivation, the culture was centrifuged and fractionated, and each culture supernatant fraction was concentrated 10-fold with Centricon plus-20 (Biomax-5). Next, 300 μl of the concentrated supernatant was mixed with the same amount of 100 mM Tris-HCl buffer solution (pH 7.5) containing 10 mM CaCl$_2$ and 1% azocoll, and stirred at a constant temperature of 37° C. for 3 hours. After the reaction, the reaction solution was immediately centrifuged, and the absorbance at 520 nm of the culture supernatant was measured to thereby determine the enzyme activity. The results are shown in Table 7. The enzyme activity to increase the 520 nm absorbance by 0.01 in the reaction at 37° C. for 1 hour is defined as 1 unit.

TABLE 7

| Strain | Enzyme Activity (units/ml of culture supernatant) |
|---|---|
| Brevibacillus choshinensis HPD31 | 33.2 |
| Brevibacillus choshinensis HPD31-SP3 | ND |

ND: not detected (at most 0.1).

As in Table 7 above, no protease activity was detected in the test of *Brevibacillus choshinensis* HPD31-SP3 with an azocoll reagent. The protease activity of the culture supernatant fraction of *Brevibacillus choshinensis* HPD31-SP3 is at most $1/330$ of that of the culture supernatant fraction of *Brevibacillus choshinensis* HPD31.

Example 14 to Example 16 above show remarkable reduction in the extracellular protease activity of the *Brevibacillus choshinensis* HPD31-SP3 of the invention as compared with that of the known strain *Brevibacillus choshinensis* HPD31.

Evaluation of Intracellular Protease Activity of *Brevibacillus choshinensis* HPD31-SP3:

Next, the intracellular protease activity of the *Brevibacillus choshinensis* HPD31-SP3 of the invention was evaluated according to a gelatin-PAGE method and a method using azocasein. As a control in the test, used was *Brevibacillus choshinensis* HPD31.

Example 17

Evaluation of Intracellular Protease Activity of Brevibacillus choshinensis HPD31-SP3 in Gelatin-PAGE Under Non-Denatured Condition Cells of *Brevibacillus choshinensis* HPD31 and those of *Brevibacillus choshinensis* HPD31-SP3 were separately cultivated in a TM liquid medium at 30° C. for 48 hours. After the cultivation, the cells were collected from the culture through centrifugation, then disrupted by ultrasonication and further centrifuged to obtain an intracellular fraction. The intracellular fraction was subjected to electrophoresis under a non-denatured condition. The electrophoresis under non-denatured condition was carried out as follows: 50 mM (as final concentration) Tris-HCl (pH 6.8) and 10% glycerol were added to 10 μl of the intracellular fraction, then applied to 10% acrylamide gel containing 0.1% gelatin, and electrophoresis was carried out with an SDS-free Tris-glycine buffer solution at 4° C. and at a constant current of 10 mA for 10 hours.

After the electrophoresis, the acrylamide gel was put in 50 mM Tris-HCl buffer solution (pH 7.5) containing 10 mM CaCl$_2$ at a constant temperature of 37° C. for 24 hours, then stained with a staining solution comprising 0.1% amide black, 30% methanol and 10% acetic acid for 30 minutes, and discolored with the same solution but not containing amide black. The results are shown in FIG. 3.

Figure 3:
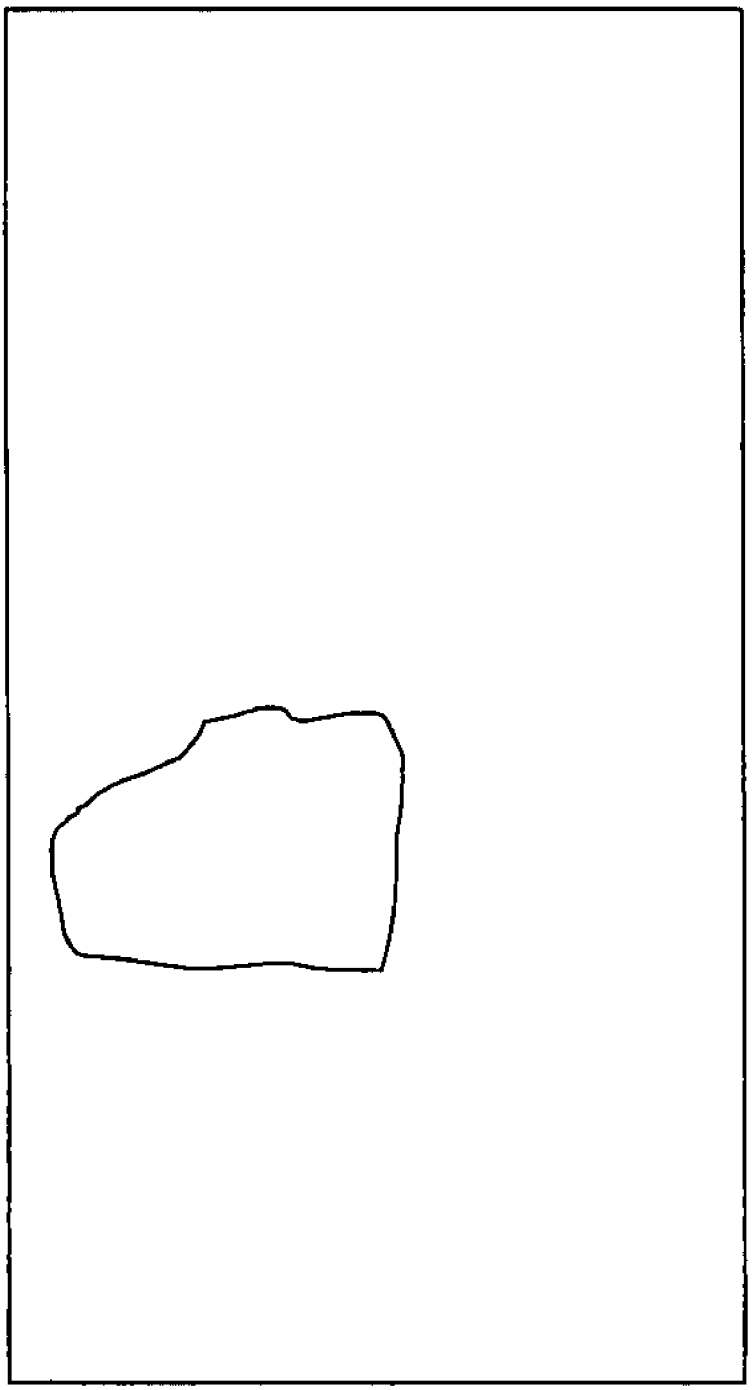
FIG. 3:
It is a drawing showing the results of measurement of the protease activity of each intracellular fraction of Brevibacillus choshinensis HPD31 (lane 1) and Brevibacillus choshinensis HPD31-SP3 (lane 2) through gelatin-PAGE (zymograph) under non-denatured condition. Within the white frame, a clear band is shown resulting from the decomposition of gelatin by the protease activity.

As in FIG. 3, the intracellular fraction of *Brevibacillus choshinensis* HPD31 gave a clear band that shows gelatin decomposition owing to the proteolytic activity thereof, but the intracellular fraction of *Brevibacillus choshinensis* HPD31-SP3 gave no clear band to indicate gelatin decomposition.

Example 18

Determination of Intracellular Protease Activity of *Brevibacillus choshinensis* HPD31-SP3 by the Use of Azocasein 200 µl of the intracellular fraction of *Brevibacillus choshinensis* HPD31 or *Brevibacillus choshinensis* HPD31-SP3 prepared in the same manner as in Example 17 was mixed with 400 µl of an enzyme reaction solution (100 mM Tris-HCl (pH 7.5), 0.2% azocasein, 10 mM $CaCl_2$), and put at a constant temperature of 37° C. for 1.5 hours, and then the reaction was stopped by adding 2.5% (as final concentration) of TCA thereto. Next, the reaction solution was centrifuged, and the absorbance at 440 nm of the supernatant was measured. The total amount of the protein in the crude enzyme solution used for the reaction was quantitatively determined according to the Bradford method using BSA as a standard. The results are shown in Table 8. The enzyme activity to increase the 440 nm absorbance by 0.01 in the reaction at 37° C. for 1 hour is defined as 1 unit.

TABLE 8

| Strain | Relative Activity (units/mg protein) |
|---|---|
| *Brevibacillus choshinensis* HPD31 | 41.5 (±1) |
| *Brevibacillus choshinensis* HPD31-SP3 | 5.2 (±1.4) |

As in Table 8 above, the intracellular protease activity of *Brevibacillus choshinensis* HPD31-SP3 was lowered to about ⅛ of that of *Brevibacillus choshinensis* HPD31.

Example 17 and Example 18 above show remarkable reduction in the intracellular protease activity of the *Brevibacillus choshinensis* HPD31-SP3 of the invention as compared with that of *Brevibacillus choshinensis* HPD31.

Secretion and Production of Recombinant Protein by *Brevibacillus choshinensis* HPD31-SP3:

Next, tests were carried out for evaluating the production and degradation of recombinant protein by the use of the *Brevibacillus choshinensis* HPD31-SP3 of the invention as a host. First, cases of secretion production of recombinant protein with the strain were tested.

Tests were carried out in relation to recombinant proteins which have been partly degraded, respectively, in the case of secretion production using *Brevibacillus choshinensis* HPD31 as a host.

Said partly degraded proteins in secretion production using *Brevibacillus choshinensis* HPD31 as a host are a porcine-derived IL-1β matured form (EMBL accession X74568); an *Escherichia coli* K12 strain-derived maltose binding protein matured form (EMBL accession AAB59056); a bovine-derived macrophage colony-stimulating factor matured form (GenBANK accession NM_174026.1); a part of porcine erysipelas antigen protein having porcine erysipelas antigenicity, EN2 (JP-A 2000-279179); and a polypeptide which is a part of *Escherichia coli* O157:H7 strain-derived intimin (SWISS-PROT accession P43261) having intimin antigenicity (Intimin (339-575)). As a control, used was *Brevibacillus choshinensis* HPD31.

Example 19

Secretion Production of Porcine IL-1β Protein Using *Brevibacillus choshinensis* HPD31-SP3

Using a sense primer (SEQ ID NO: 26, FIG. 26) in which an NcoI recognition sequence and a sequence encoding a part of a signal peptide has been added to the DNA sequence encoding the N-terminal amino acid residues of a porcine-derived IL-1β matured form (EMBL accession X74568) (hereinafter referred to as porcine IL-1β), and an antisense primer (SEQ ID NO: 27, FIG. 27) in which an HindIII recognition sequence has been added to the DNA sequence encoding the C-terminal amino acid residues thereof, and using a porcine-derived IL-1β cDNA as a template, PCR was carried out. Next, the DNA fragment amplified through PCR was processed with restriction endonucleases NcoI and HindIII, and inserted into the NcoI/HindIII restriction endonuclease cleavage site of a pNY301 vector to thereby construct a vector for porcine IL-1β secretion production. The porcine IL-1β secretion production vector is referred to as pNY301-pIL-1β.

Next, pNY301-pIL-1β was introduced into *Brevibacillus choshinensis* HPD31 and *Brevibacillus choshinensis* HPD31-SP3 according to an electroporation method to thereby construct their transformants. Next, the transformants were separately cultivated in a TM liquid medium at 30° C. for 90 hours. After the cultivation, the culture was centrifuged and fractionated, and the resulting culture supernatant fraction was subjected to acrylamide gel electrophoresis at a concentration gradient of from 10 to 25%. After the electrophoresis, the protein was transferred onto a nitrocellulose film by the use of a semi-dry protein transfer device. Next, according to an ordinary method, the transferred film was subjected to western blotting analysis using an anti-pig IL-1β antibody to thereby detect porcine IL-1β.

Figure 5:
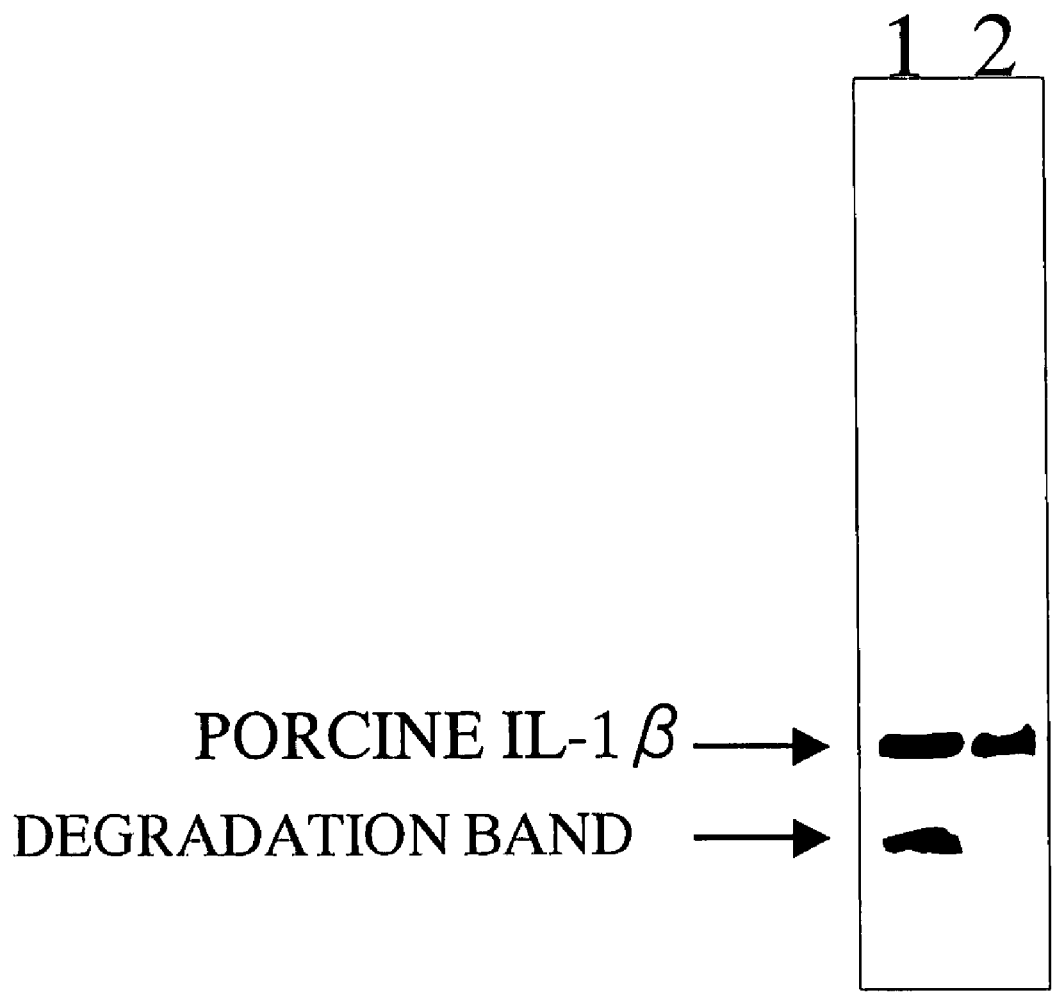
FIG. 5:
It is a drawing showing the results of western blotting with an anti-porcine IL-1β antibody to a porcine IL-1β secreted and produced through genetic recombination using *Brevibacillus choshinensis* HPD31 and *Brevibacillus choshinensis* HPD31-SP3 as a host, and it is a drawing showing the secretion production and degradation of the porcine IL-1β. The lane 1 indicates a genetic recombinant *Brevibacillus choshinensis* HPD31/pNY301-pIL-1β, and the lane 2 indicates a genetic recombinant *Brevibacillus choshinensis* HPD31-SP3/pNY301-pIL-1β.

As a result, the sample using *Brevibacillus choshinensis* HPD31 as a host gave a clear band indicating the degradation of porcine IL-1β, but the sample using the *Brevibacillus choshinensis* HPD31-SP3 of the invention as a host did not give a band indicating the degradation of porcine IL-1β, as in FIG. 5.

Figure 4:
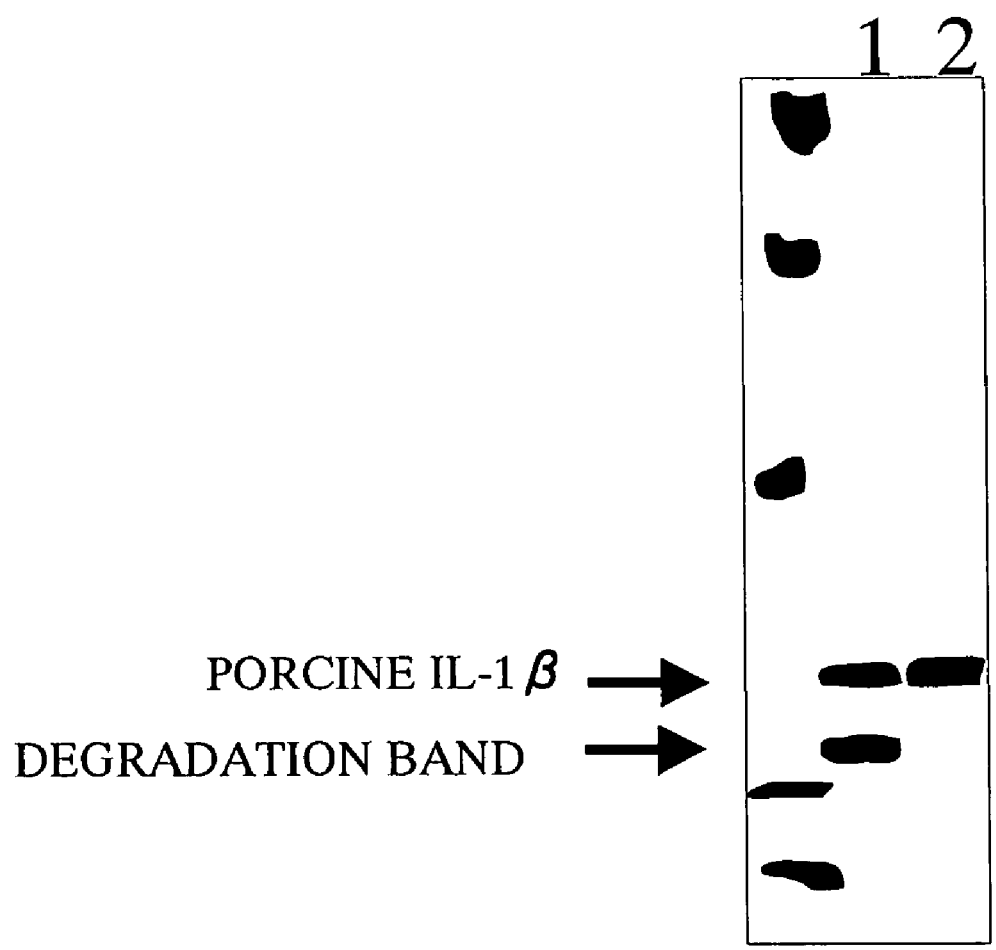
FIG. 4:
It is a drawing showing the results of CBB staining of a porcine IL-1β secreted and produced through genetic recombination using Brevibacillus choshinensis HPD31 and Brevibacillus choshinensis HPD31-SP3 as a host, and it is a drawing showing the secretion production and degradation of the porcine IL-1β. The lane 1 indicates a genetic recombinant *Brevibacillus choshinensis* HPD31/pNY301-pIL-1β, and the lane 2 indicates a genetic recombinant *Brevibacillus choshinensis* HPD31-SP3/pNY301-pIL-1β.

After the electrophoresis, the gel was stained with CBB for detection of a protein band, and through densitometry of the band corresponding to porcine IL-1β, the amount of the porcine IL-1β accumulated in the culture was determined. The results are shown in FIG. 4 and Table 9.

TABLE 9

| Host Strain | Amount of Porcine IL-1β Accumulated in Culture (mg/liter) |
|---|---|
| *Brevibacillus choshinensis* HPD31 | 30 |
| *Brevibacillus choshinensis* HPD31-SP3 | 80 |

As in Table 9, the amount of porcine IL-1β in the culture produced by the use of *Brevibacillus choshinensis* HPD31-SP3 as a host increased to at least about 2.5 times as compared with that in the culture produced by the use of Brevibacillus choshinensis HPD31 as a host.

Example 20

Secretion Production of *Escherichia coli* MBP Using *Brevibacillus choshinensis* HPD31-SP3

Using a sense primer (SEQ ID NO:28, FIG. 28) in which a PstI recognition sequence has been added to the DNA sequence encoding the N-terminal amino acid residues of an *Escherichia coli* K12 strain-derived maltose binding protein (MBP) matured form (EMBL accession AAB59056) (hereinafter referred to as *Escherichia coli* MBP), and an antisense primer (SEQ ID NO:29, FIG. 29) in which an HindIII recognition sequence has been added to the DNA sequence encoding the C-terminal amino acid residues thereof, and using an *Escherichia coli* K12 strain genome DNA as a template, PCR was carried out. Next, the DNA fragment amplified through PCR was processed with restriction endonucleases PstI and HindIII, and inserted into the PstI/HindIII restriction endonuclease cleavage site of a pNY301 vector to thereby construct a vector for *Escherichia coli* MBP secretion production. The *Escherichia coli* MBP secretion production vector is referred to as pNY301-MBP.

Next, pNY301-MBP was introduced into *Brevibacillus choshinensis* HPD31 and *Brevibacillus choshinensis* HPD31-SP3 according to an electroporation method to thereby construct their transformants. Next, the transformants were separately cultivated in a TM liquid medium at 30° C. for 72 hours. After the cultivation, the culture was centrifuged and fractionated, and the resulting culture supernatant fraction was subjected to SDS-PAGE and western blotting analysis in the same manner as in Example 19. As a result, the sample using *Brevibacillus choshinensis* HPD31 as a host gave a clear band indicating the degradation of *Escherichia coli* MBP, but the sample using the *Brevibacillus choshinensis* HPD31-SP3 of the invention as a host did not give a band indicating the degradation of *Escherichia coli* MBP.

After the electrophoresis, the gel was stained with CBB for detection of a protein band, and through densitometry of the band corresponding to *Escherichia coli* MBP, the amount of the *Escherichia coli* MBP accumulated in the culture was determined. The results are shown in Table 10.

TABLE 10

| Host Strain | Amount of *Escherichia coli* MBP Accumulated in Culture (mg/liter) |
|---|---|
| *Brevibacillus choshinensis* HPD31 | 500 |
| *Brevibacillus choshinensis* HPD31-SP3 | 900 |

As in Table 10, the amount of *Escherichia coli* MBP in the culture produced by the use of *Brevibacillus choshinensis* HPD31-SP3 as a host increased to about 2 times as compared with that in the culture produced by the use of *Brevibacillus choshinensis* HPD31 as a host.

Example 21

Secretion Production of Bovine M-CSF Using *Brevibacillus choshinensis* HPD31-SP3

Using a sense primer (SEQ ID NO:30, FIG. 30) in which a BamHI recognition sequence has been added to the DNA sequence encoding the N-terminal amino acid residues of a bovine-derived macrophage colony stimulating factor matured form (GenBANK accession NM_174026.1) (hereinafter referred to as bovine M-CSF), and an antisense primer (SEQ ID NO:31, FIG. 31) in which an HindIII recognition sequence has been added to the DNA sequence encoding the C-terminal amino acid residues thereof, and using a bovine M-CSF cDNA as a template, PCR was carried out. Next, the DNA fragment amplified through PCR was processed with restriction endonucleases BamHI and HindIII, and inserted into the BamHI/HindIII restriction endonuclease cleavage site of a pNY301 vector to thereby construct a vector for bovine M-CSF secretion production. The bovine M-CSF secretion production vector is referred to as pNY301-M-CSF.

Next, pNY301-M-CSF was introduced into *Brevibacillus choshinensis* HPD31 and *Brevibacillus choshinensis* HPD31-SP3 according to an electroporation method to thereby construct their transformants. Next, the transformants were separately cultivated in a TM liquid medium at 30° C. for 72 hours. After the cultivation, the culture was centrifuged and fractionated, and the resulting culture supernatant fraction was subjected to SDS-PAGE and western blotting analysis in the same manner as in Example 19. As a result, the sample using *Brevibacillus choshinensis* HPD31 as a host gave a band indicating the degradation of bovine M-CSF, but the sample using *Brevibacillus choshinensis* HPD31-SP3 as a host did not give a band indicating the degradation of bovine M-CSF.

After the electrophoresis, the gel was stained with CBB for detection of a protein band, and through densitometry of the band corresponding to bovine M-CSF, the amount of the protein accumulated in the culture was determined. The results are shown in Table 11.

TABLE 11

| Host Strain | Amount of Bovine M-CSF Accumulated in Culture (mg/liter) |
|---|---|
| *Brevibacillus choshinensis* HPD31 | 50 |
| *Brevibacillus choshinensis* HPD31-SP3 | 150 |

As in Table 11, the amount of bovine M-CSF accumulated in the culture produced by the use of *Brevibacillus choshinensis* HPD31-SP3 as a host increased to about 3 times as compared with that in the culture produced by the use of *Brevibacillus choshinensis* HPD31 as a host.

Example 22

Secretion Production of EN2 Using *Brevibacillus choshinensis* HPD31-SP3

A plasmid vector pNH300 en2 that expresses a part of porcine erysipelas antigen protein, EN2 (JP-A2000-279179) was introduced into *Brevibacillus choshinensis* HPD31 and *Brevibacillus choshinensis* HPD31-SP3 according to an electroporation method to thereby construct their transformants, and the transformants were separately cultivated in a TM liquid medium at 30° C. for 90 hours.

After the cultivation, the culture was centrifuged and fractionated, and the resulting culture supernatant fraction was subjected to SDS-PAGE and western blotting analysis in the same manner as in Example 19. As a result, the sample using *Brevibacillus choshinensis* HPD31 as a host gave a clear band indicating the degradation of EN2, but the sample using Brevibacillus choshinensis HPD31-SP3 as a host did not give a band indicating the degradation of EN2.

After the electrophoresis, the gel was stained with CBB for detection of a protein band, and through densitometry of the band corresponding to EN2, the amount of the protein accumulated in the culture was determined. The results are shown in Table 12.

TABLE 12

| Host Strain | Amount of EN2 Accumulated in Culture (mg/liter) |
|---|---|
| Brevibacillus choshinensis HPD31 | 400 |
| Brevibacillus choshinensis HPD31-SP3 | 750 |

As in Table 12, the amount of EN2 accumulated in the culture produced by the use of Brevibacillus choshinensis HPD31-SP3 as a host increased to about 2 times as compared with that in the culture produced by the use of Brevibacillus choshinensis HPD31 as a host.

Example 23

Production of Intimin (339-575) Using Brevibacillus choshinensis HPD31-SP3

Using a sense primer (SEQ ID NO:32, FIG. 32) in which a BamHI recognition sequence has been added to the DNA sequence corresponding to the 339th amino acid sequence of matured intimin, and an antisense primer (SEQ ID NO:33, FIG. 33) in which an HindIII recognition sequence has been added to the DNA sequence corresponding to the amino acid sequence near the 575th amino acid thereof, and using an intimin gene as a template, PCR was carried out. Next, the DNA fragment amplified through PCR was processed with restriction endonucleases HindIII and BamHI, and inserted into the BamHI/HindIII restriction endonuclease cleavage site of pNY301 to thereby construct a plasmid vector that expresses a polypeptide part corresponding to the amino acid sequence of from 339th to 575th amino acid residues of an Escherichia coli O157:H7 strain-derived intimin (SWISS-PROT accession P43261) (hereinafter referred to as Intimin (339-575)). The Intimin (339-575) secretion production vector is referred to as pNY301-Intimin.

Next, pNY301-Intimin was introduced into Brevibacillus choshinensis HPD31 and Brevibacillus choshinensis HPD31-SP3 according to an electroporation method to thereby construct their transformants. Next, the transformants were separately cultivated in a TM liquid medium at 30° C. for 90 hours. After the cultivation, the culture was centrifuged and fractionated, and the resulting culture supernatant fraction was subjected to SDS-PAGE and western blotting analysis in the same manner as in Example 19. As a result, the sample using Brevibacillus choshinensis HPD31 as a host gave clear bands indicating the degradation of Intimin (339-575), but the sample using Brevibacillus choshinensis HPD31-SP3 as a host did not give any clear band indicating the degradation of Intimin (339-575).

After the electrophoresis, the gel was stained with CBB for detection of a protein band, and through densitometry of the band corresponding to Intimin (339-575), the amount of Intimin (339-575) accumulated in the culture was determined. The results are shown in Table 13.

TABLE 13

| Host Strain | Amount of Intimin (339-575) Accumulated in Culture (mg/liter) |
|---|---|
| Brevibacillus choshinensis HPD31 | 100 |
| Brevibacillus choshinensis HPD31-SP3 | 200 |

As in Table 13, the amount of Intimin (339-575) accumulated in the culture produced by the use of Brevibacillus choshinensis HPD31-SP3 as a host increased to about 2 times as compared with that in the culture produced by the use of Brevibacillus choshinensis HPD31 as a host.

Example 19 to Example 23 show the following: When Brevibacillus choshinensis HPD31 was used as a host, a part of the recombinant protein secreted and produced was degraded. However, when Brevibacillus choshinensis HPD31-SP3 was used as a host, the accumulated amount of the protein increased as compared with that in the case where Brevibacillus choshinensis HPD31 was used as a host.

It is understood that these results were brought about when Brevibacillus choshinensis HPD31-SP3 was used as a host and the degradation of the secreted and produced protein was significantly suppressed.

Intracellular Accumulation and Production of Recombinant Protein by Brevibacillus choshinensis HPD31-SP3:

Next, tests were further carried out for evaluating the production and degradation of recombinant protein by the use of Brevibacillus choshinensis HPD31-SP3 as a host not in secretion production of recombinant protein but in intracellular accumulation of the produced recombinant protein. Porcine-derived interferon-γ (PIR accession S10513) and canine-derived interferon-β (GenBANK accession E11229) were used as said recombinant protein. When each of these proteins was used for intracellular accumulation production using Brevibacillus choshinensis HPD31, the protein produced was partly degradation in the cells.

As a control, used was Brevibacillus choshinensis HPD31.

Example 24

Intracellular Accumulation Production of Recombinant Porcine-Derived Interferon-γ Using Brevibacillus choshinensis HPD31-SP3

Using a sense primer (SEQ ID NO:34, FIG. 34) in which a ccatggct sequence that includes an NcoI recognition sequence and a sequence encoding MetAla has been added to the DNA sequence encoding the N-terminal amino acid residues of a porcine-derived interferon-γ matured form (PIR accession S10513) (hereinafter referred to as porcine IFN-γ), and an antisense primer (SEQ ID NO:35, FIG. 35) in which an HindIII recognition sequence has been added to the DNA sequence encoding the C-terminal amino acid residues thereof, and using a porcine-derived interferon-γ cDNA as a template, PCR was carried out. Next, the DNA fragment amplified through PCR was processed with restriction endonucleases NcoI and HindIII, and inserted into the BspHI/HindIII restriction endonuclease cleavage site existing on the translation initiation methionine of a pNY301 vector to thereby construct a vector for porcine IFN-γ expression. The porcine IFN-γ expression vector is referred to as pNY301-pIFN-γ. Since this pNY301-pIFN-γ does not have a DNA sequence that encodes a secretion signal peptide, the produced porcine IFN-γ is intracellularly accumulated.

Next, pNY301-pIFN-γ was introduced into *Brevibacillus choshinensis* HPD31 and *Brevibacillus choshinensis* HPD31-SP3 according to an electroporation method to thereby construct their transformants. As a control, *Brevibacillus choshinensis* HPD31/pNY301 was constructed, into which was introduced pNY301 with no porcine IFN-γ gene inserted.

Next, the transformants and *Brevibacillus choshinensis* HPD31/pNY301 were separately cultivated in a TM liquid medium at 30° C. for 72 hours. After the cultivation, the cells were recovered from the culture through centrifugation and disrupted by ultrasonication, and the intracellular fraction was collected through centrifugation. Next, the intracellular fraction was subjected to SDS-PAGE and western blotting analysis in the same manner as in Example 19.

Figure 6:
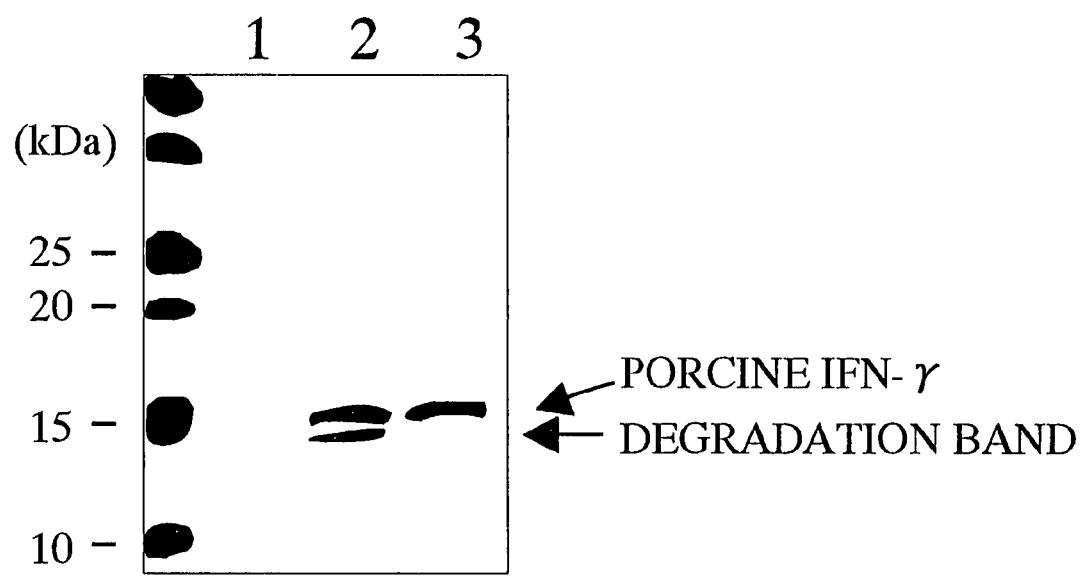
FIG. 6:
It is a drawing showing the results of western blotting with an anti-porcine IFN-γ antibody to a porcine IFN-γ intracellularly accumulated and produced through genetic recombination using *Brevibacillus choshinensis* HPD31 and *Brevibacillus choshinensis* HPD31-SP3 as a host, and it is a drawing showing the intracellular accumulation production and degradation of the porcine IFN-γ. The lane 1 indicates a genetic recombinant *Brevibacillus choshinensis* HPD31/pNY301; the lane 2 indicates a genetic recombinant *Brevibacillus choshinensis* HPD31/pNY301-pIFN-γ; and the lane 3 indicates a genetic recombinant *Brevibacillus choshinensis* HPD31-SP3/pNY301-pIFN-γ.

As a result, the sample using *Brevibacillus choshinensis* HPD31 as a host gave a clear band indicating the degradation of porcine IFN-γ, but the sample using *Brevibacillus choshinensis* HPD31-SP3 as a host did not give a band indicating the degradation of porcine IFN-γ, as in FIG. 6.

After the electrophoresis, the gel was stained with CBB for detection of a protein band, and through densitometry of the band corresponding to porcine IFN-γ, the amount of the protein accumulated in the cells was determined. The results are shown in Table 14.

TABLE 14

| Host Strain | Amount of Porcine IFN-γ Accumulated in Cells (mg/liter) |
|---|---|
| *Brevibacillus choshinensis* HPD31 | 30 |
| *Brevibacillus choshinensis* HPD31-SP3 | 60 |

As in Table 14, the intracellularly-accumulated amount of porcine IFN-γ produced by the use of *Brevibacillus choshinensis* HPD31-SP3 as a host increased to about 2 times as compared with that in the cells produced by the use of *Brevibacillus choshinensis* HPD31 as a host.

Example 25

Intracellular Accumulation Production of Canine-Derived Interferon-β Using *Brevibacillus choshinensis* HPD31-SP3

Using a sense primer (SEQ ID NO:36, FIG. 36) in which a BspHI recognition sequence has been added to the DNA sequence encoding the N-terminal amino acid residues of a canine-derived interferon-β matured form (GenBANK accession E11229) (hereinafter referred to as canine IFN-β), and an antisense primer (SEQ ID NO:37, FIG. 37) in which an HindIII recognition sequence has been added to the DNA sequence encoding the C-terminal amino acid residues thereof, and using a canine-derived interferon-β cDNA as a template, PCR was carried out. Next, the DNA fragment amplified through PCR was processed with restriction endonucleases BspHI and HindIII, and inserted into the BspHI/HindIII restriction endonuclease cleavage site existing on the translation initiation methionine of a pNY301 vector to thereby construct a vector for canine IFN-β expression. The canine IFN-β expression vector is referred to as pNY301-cIFN-β. Since this pNY301-cIFN-β does not have a DNA sequence that encodes a secretion signal peptide, the produced canine IFN-β is intracellularly accumulated.

Next, pNY301-cIFN-β was introduced into *Brevibacillus choshinensis* HPD31 and *Brevibacillus choshinensis* HPD31-SP3 according to an electroporation method to thereby construct their transformants. Next, the transformants were separately cultivated in a TM liquid medium at 30° C. for 72 hours. After the cultivation, the cells were recovered from the culture through centrifugation and disrupted by ultrasonication, and the intracellular fraction was collected through centrifugation. Next, the intracellular fraction was subjected to SDS-PAGE and western blotting analysis in the same manner as in Example 21. As a result, the sample using *Brevibacillus choshinensis* HPD31 as a host gave a clear band indicating the degradation of canine IFN-β, but the sample using *Brevibacillus choshinensis* HPD31-SP3 as a host did not give a band indicating the degradation of canine IFN-β.

After the electrophoresis, the gel was stained with CBB for detection of a protein band, and through densitometry of the band corresponding to canine IFN-β, the amount of the protein accumulated in the cells was determined. The results are shown in Table 15.

TABLE 15

| Host Strain | Amount of Canine IFN-β Accumulated in Cells (mg/liter) |
|---|---|
| *Brevibacillus choshinensis* HPD31 | 50 |
| *Brevibacillus choshinensis* HPD31-SP3 | 80 |

As in Table 15, the intracellularly-accumulated amount of canine IFN-β produced by the use of *Brevibacillus choshinensis* HPD31-SP3 as a host increased to about 1.6 times as compared with that in the cells produced by the use of *Brevibacillus choshinensis* HPD31 as a host.

Example 24 and Example 25 show the following: When the *Brevibacillus choshinensis* HPD31-SP3 of the invention was used as a host in recombinant protein production, then the accumulated amount of the protein increased as compared with the case where *Brevibacillus choshinensis* HPD3 was used as a host. It is understood that these results were brought about because the degradation of the intracellularly-accumulated recombinant protein was suppressed significantly owing to the inactivation of the intracellular protease gene imp.

Deposition Number: FERM BP-08497

Designation of Deposition:

*Brevibacillus choshinensis* HPD31-SP3

Name of Depositary Agency:

International Patent Organism Depositary, National Institute of Advanced Industrial Science and Technology Address of Depository Agency:

Central 6, 1-1, Higashi 1-chome, Tsukuba-shi, Ibaraki-ken, 305-8566, Japan

Date of Deposition: Sep. 11, 2003

Deposition Number: FERM BP-6863

Designation of Deposition:

*Brevibacillus choshinensis* HPD31 (FERM BP-1087)

Name of Depositary Agency:
  National Institute of Bioscience and Human-Technology, Agency of Industrial Science and Technology, Ministry of International Trade and Industry Address of Depository Agency:
  1-3, Higashi 1-chome, Tsukub-shi, Ibaraki-ken, 305-8566, Japan Date of Deposition: Aug. 31, 1999

Deposition Number: FERM BP-6623

Designation of Deposition:
  *Bacillus brevis* HPD31-S5

Name of Depositary Agency:
  National Institute of Bioscience and Human-Technology, Agency of Industrial Science and Technology, Ministry of International Trade and Industry Address of Depository Agency:
  1-3, Higashi 1-chome, Tsukub-shi, Ibaraki-ken, 305-8566, Japan Date of Deposition: Jan. 19, 1999

The invention claimed is:

1. A biologically pure culture of *Brevibacillus choshinensis* which does not form spores, and which has an inactivated hos gene which comprises SEQ ID NO: 1.

2. The biologically pure culture of *Brevibacillus choshinensis* of claim 1 having the following properties:
  (a) Morphology:
    size of cell:
      liquid medium: 0.4 to 0.6×1.5 to 4 μm,
    form of cell: *bacillus,*
    presence or absence of spore: absence,
  (b) Physiologica properties:
    reduction of nitrate: −,
    VP test: =,
    utilization of citric acid: +,
    urease: −,
    oxidase: +,
    catalase: +,
  (c) Other Properties:
    temperature resistance: die at 60° C.

* * * * *

UNITED STATES PATENT AND TRADEMARK OFFICE
CERTIFICATE OF CORRECTION

| | |
|---|---|
| PATENT NO. | : 7,655,452 B1 |
| APPLICATION NO. | : 10/578781 |
| DATED | : February 2, 2010 |
| INVENTOR(S) | : Hanagata et al. |

It is certified that error appears in the above-identified patent and that said Letters Patent is hereby corrected as shown below:

On the title page, Item (54) and column 1, the title is incorrect. Item (54) and column 1 should read:

Item -- (54) *BREVIBACILLUS CHOSHINENSIS* AND PROCESS FOR PRODUCING PROTEIN WITH USE OF THE MICROBE AS HOST --

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,452 B1 | Page 1 of 1 |
| APPLICATION NO. | : 10/578781 | |
| DATED | : February 2, 2010 | |
| INVENTOR(S) | : Hanagata et al. | |

It is certified that error appears in the above-identified patent and that said Letters Patent is hereby corrected as shown below:

On the title page, Item (54) and column 1, the title is incorrect. Item (54) and column 1 should read:

Item -- (54) *BREVIBACILLUS CHOSHINENSIS* AND PROCESS FOR PRODUCING PROTEIN WITH USE OF THE MICROBE AS HOST --.

Column 72, line 3, "VP test: =," should read -- VP test:- --.

Signed and Sealed this

Twentieth Day of April, 2010

David J. Kappos
*Director of the United States Patent and Trademark Office*

SEQUENCE LISTING

```
<160> NUMBER OF SEQ ID NOS: 41

<210> SEQ ID NO 1
<211> LENGTH: 756
<212> TYPE: DNA
<213> ORGANISM: Brevibacillus choshinensis
<220> FEATURE:
<221> NAME/KEY: CDS
<222> LOCATION: (1)..(753)

<400> SEQUENCE: 1 atg ggt gcc gat atc aaa aat gcg agt caa cca ttt ctg acc aat gac      48
Met Gly Ala Asp Ile Lys Asn Ala Ser Gln Pro Phe Leu Thr Asn Asp
 1               5                  10                  15 caa gtg aaa gat ttg ata gcc aag agc caa gct ggc gat acg gat gca      96
Gln Val Lys Asp Leu Ile Ala Lys Ser Gln Ala Gly Asp Thr Asp Ala
             20                  25                  30 cgt gag ctt ctc gtg aat agc aat atc aga ctg gtc tgg tcc gtc gtc     144
Arg Glu Leu Leu Val Asn Ser Asn Ile Arg Leu Val Trp Ser Val Val
         35                  40                  45 cag cgc ttt atc aac cgc ggg tat gaa gcg gat gat ttg ttt cag atc     192
Gln Arg Phe Ile Asn Arg Gly Tyr Glu Ala Asp Asp Leu Phe Gln Ile
     50                  55                  60 ggt tgc att ggc ttg ctc aag gcc gtt gac aag ttc gat ctt tcg tac     240
Gly Cys Ile Gly Leu Leu Lys Ala Val Asp Lys Phe Asp Leu Ser Tyr
 65                  70                  75                  80 gat gtg aga ttt tcg acc tat gcg gtg cca atg atc atc gga gaa att     288
Asp Val Arg Phe Ser Thr Tyr Ala Val Pro Met Ile Ile Gly Glu Ile
                 85                  90                  95 caa cgc ttt ttg cgc gat gac ggt acg gtt aag gtc agt cga tcg tta     336
Gln Arg Phe Leu Arg Asp Asp Gly Thr Val Lys Val Ser Arg Ser Leu
            100                 105                 110 aaa gaa aca gcg aat aag gtg cgg cga tca aag gat gaa ttg tac aag     384
Lys Glu Thr Ala Asn Lys Val Arg Arg Ser Lys Asp Glu Leu Tyr Lys
        115                 120                 125 caa ttc ggc cgt gcc ccc acg atc gca gaa gtg gca gaa gca gtg gga     432
Gln Phe Gly Arg Ala Pro Thr Ile Ala Glu Val Ala Glu Ala Val Gly
    130                 135                 140 atc acg ccg gag gaa gta gtc ttt gcg caa gag gca agc aga gcg cct     480
Ile Thr Pro Glu Glu Val Val Phe Ala Gln Glu Ala Ser Arg Ala Pro
145                 150                 155                 160 tcc tcc atc cat gag acc gtt ttt gaa aat gac ggc gat ccc atc aca     528
Ser Ser Ile His Glu Thr Val Phe Glu Asn Asp Gly Asp Pro Ile Thr
                165                 170                 175 ctg atc gat cag ata gcg gat gaa ggt gtg aac aag tgg ttt gag aaa     576
Leu Ile Asp Gln Ile Ala Asp Glu Gly Val Asn Lys Trp Phe Glu Lys
            180                 185                 190 att gcc ttg aag gac gcc atc agc agg ctg agc gag cgt gag cag ctc     624
```

```
Ile Ala Leu Lys Asp Ala Ile Ser Arg Leu Ser Glu Arg Glu Gln Leu
            195                 200                 205 atc gtc tac ctg cgc tat tac aag gat cag aca cag tct gag gta gca      672
Ile Val Tyr Leu Arg Tyr Tyr Lys Asp Gln Thr Gln Ser Glu Val Ala
        210                 215                 220 gag cgt cta ggg att tcg cag gtc cag gtc tcg cgt ctg gaa aag cgt      720
Glu Arg Leu Gly Ile Ser Gln Val Gln Val Ser Arg Leu Glu Lys Arg
225                 230                 235                 240 atc ctg cta acg atc aag gag caa att gaa cat tag                      756
Ile Leu Leu Thr Ile Lys Glu Gln Ile Glu His
                245                 250

<210> SEQ ID NO 2
<211> LENGTH: 251
<212> TYPE: PRT
<213> ORGANISM: Brevibacillus choshinensis

<400> SEQUENCE: 2

Met Gly Ala Asp Ile Lys Asn Ala Ser Gln Pro Phe Leu Thr Asn Asp
  1               5                  10                  15

Gln Val Lys Asp Leu Ile Ala Lys Ser Gln Ala Gly Asp Thr Asp Ala
                 20                  25                  30

Arg Glu Leu Leu Val Asn Ser Asn Ile Arg Leu Val Trp Ser Val Val
             35                  40                  45

Gln Arg Phe Ile Asn Arg Gly Tyr Glu Ala Asp Leu Phe Gln Ile
         50                  55                  60

Gly Cys Ile Gly Leu Leu Lys Ala Val Asp Lys Phe Asp Leu Ser Tyr
 65                  70                  75                  80

Asp Val Arg Phe Ser Thr Tyr Ala Val Pro Met Ile Ile Gly Glu Ile
                 85                  90                  95

Gln Arg Phe Leu Arg Asp Asp Gly Thr Val Lys Val Ser Arg Ser Leu
            100                 105                 110

Lys Glu Thr Ala Asn Lys Val Arg Ser Lys Asp Glu Leu Tyr Lys
        115                 120                 125

Gln Phe Gly Arg Ala Pro Thr Ile Ala Glu Val Ala Glu Ala Val Gly
    130                 135                 140

Ile Thr Pro Glu Glu Val Val Phe Ala Gln Glu Ala Ser Arg Ala Pro
145                 150                 155                 160

Ser Ser Ile His Glu Thr Val Phe Glu Asn Asp Gly Asp Pro Ile Thr
                165                 170                 175

Leu Ile Asp Gln Ile Ala Asp Glu Gly Val Asn Lys Trp Phe Glu Lys
            180                 185                 190

Ile Ala Leu Lys Asp Ala Ile Ser Arg Leu Ser Glu Arg Glu Gln Leu
        195                 200                 205

Ile Val Tyr Leu Arg Tyr Tyr Lys Asp Gln Thr Gln Ser Glu Val Ala
    210                 215                 220

Glu Arg Leu Gly Ile Ser Gln Val Gln Val Ser Arg Leu Glu Lys Arg
225                 230                 235                 240

Ile Leu Leu Thr Ile Lys Glu Gln Ile Glu His
                245                 250

<210> SEQ ID NO 3
<211> LENGTH: 2265
<212> TYPE: DNA
<213> ORGANISM: Brevibacillus choshinensis
<220> FEATURE:
<221> NAME/KEY: CDS
<222> LOCATION: (1)..(2262)
```

<400> SEQUENCE: 3

| | | | | | | | | | | | | | | | | |
|---|---|---|---|---|---|---|---|---|---|---|---|---|---|---|---|---|
| gtg | aac | gca | gtg | aag | aaa | ggc | aag | aag | cta | tta | tcc | atc | cta | ttt | tct | 48 |
| Val | Asn | Ala | Val | Lys | Lys | Gly | Lys | Lys | Leu | Leu | Ser | Ile | Leu | Phe | Ser | |
| 1 | | | | 5 | | | | | 10 | | | | | 15 | | |

| tcc | tca | ctg | gtc | ctg | agc | ggc | att | gcg | gcg | gtt | cca | gcg | aca | ggg | atg | 96 |
|---|---|---|---|---|---|---|---|---|---|---|---|---|---|---|---|---|
| Ser | Ser | Leu | Val | Leu | Ser | Gly | Ile | Ala | Ala | Val | Pro | Ala | Thr | Gly | Met | |
| | | | 20 | | | | | 25 | | | | | 30 | | | |

| gcc | aag | tca | aag | gac | aag | ccg | ccg | ctt | gaa | gtg | gat | ttg | tcc | aca | gtg | 144 |
|---|---|---|---|---|---|---|---|---|---|---|---|---|---|---|---|---|
| Ala | Lys | Ser | Lys | Asp | Lys | Pro | Pro | Leu | Glu | Val | Asp | Leu | Ser | Thr | Val | |
| | | 35 | | | | | 40 | | | | | 45 | | | | |

| aac | atg | gat | cgt | ttg | gtt | aaa | gcc | ttg | atc | gac | caa | ggt | gaa | atc | gac | 192 |
|---|---|---|---|---|---|---|---|---|---|---|---|---|---|---|---|---|
| Asn | Met | Asp | Arg | Leu | Val | Lys | Ala | Leu | Ile | Asp | Gln | Gly | Glu | Ile | Asp | |
| 50 | | | | | 55 | | | | | 60 | | | | | | |

| gag | gac | gcc | gac | cag | gaa | gag | atc | aac | aaa | gct | gtg | gag | aag | ttt | ttg | 240 |
|---|---|---|---|---|---|---|---|---|---|---|---|---|---|---|---|---|
| Glu | Asp | Ala | Asp | Gln | Glu | Glu | Ile | Asn | Lys | Ala | Val | Glu | Lys | Phe | Leu | |
| 65 | | | | 70 | | | | | 75 | | | | | 80 | | |

| aga | gac | aag | aaa | gtt | ccc | cac | ggc | att | gat | gac | tcc | agc | tcc | ttc | ggg | 288 |
|---|---|---|---|---|---|---|---|---|---|---|---|---|---|---|---|---|
| Arg | Asp | Lys | Lys | Val | Pro | His | Gly | Ile | Asp | Asp | Ser | Ser | Ser | Phe | Gly | |
| | | | 85 | | | | | 90 | | | | | 95 | | | |

| aaa | aaa | gca | agc | aaa | acc | cag | ctt | tcg | gca | gta | tca | aag | gca | gca | agc | 336 |
|---|---|---|---|---|---|---|---|---|---|---|---|---|---|---|---|---|
| Lys | Lys | Ala | Ser | Lys | Thr | Gln | Leu | Ser | Ala | Val | Ser | Lys | Ala | Ala | Ser | |
| | | 100 | | | | | 105 | | | | | 110 | | | | |

| aaa | gta | tcc | aag | ctc | aaa | gat | gac | aag | caa | gtg | cgc | gct | tcc | aag | cgg | 384 |
|---|---|---|---|---|---|---|---|---|---|---|---|---|---|---|---|---|
| Lys | Val | Ser | Lys | Leu | Lys | Asp | Asp | Lys | Gln | Val | Arg | Ala | Ser | Lys | Arg | |
| | | 115 | | | | | 120 | | | | | 125 | | | | |

| gta | cat | acg | gat | aat | ctg | gtg | att | gcc | ctg | gtc | gag | ttc | aat | gat | ctg | 432 |
|---|---|---|---|---|---|---|---|---|---|---|---|---|---|---|---|---|
| Val | His | Thr | Asp | Asn | Leu | Val | Ile | Ala | Leu | Val | Glu | Phe | Asn | Asp | Leu | |
| 130 | | | | | 135 | | | | | 140 | | | | | | |

| gag | cac | aac | cag | gtg | cca | aaa | caa | agc | gat | tcc | ttg | tgg | acg | gca | gac | 480 |
|---|---|---|---|---|---|---|---|---|---|---|---|---|---|---|---|---|
| Glu | His | Asn | Gln | Val | Pro | Lys | Gln | Ser | Asp | Ser | Leu | Trp | Thr | Ala | Asp | |
| 145 | | | | | 150 | | | | | 155 | | | | | 160 | |

| ttc | gac | caa | aag | cac | tac | gag | gaa | atg | ctg | ttc | gat | cgt | aaa | ggc | tat | 528 |
|---|---|---|---|---|---|---|---|---|---|---|---|---|---|---|---|---|
| Phe | Asp | Gln | Lys | His | Tyr | Glu | Glu | Met | Leu | Phe | Asp | Arg | Lys | Gly | Tyr | |
| | | | | 165 | | | | | 170 | | | | | 175 | | |

| acg | act | cct | gaa | ggg | ata | agc | atg | acc | acg | atg | gcc | aag | tac | tac | tac | 576 |
|---|---|---|---|---|---|---|---|---|---|---|---|---|---|---|---|---|
| Thr | Thr | Pro | Glu | Gly | Ile | Ser | Met | Thr | Thr | Met | Ala | Lys | Tyr | Tyr | Tyr | |
| | | | 180 | | | | | 185 | | | | | 190 | | | |

| gag | caa | tcg | ggt | gag | aca | tgg | acc | gtg | gat | ggg | gtt | gtc | act | ccg | tgg | 624 |
|---|---|---|---|---|---|---|---|---|---|---|---|---|---|---|---|---|
| Glu | Gln | Ser | Gly | Glu | Thr | Trp | Thr | Val | Asp | Gly | Val | Val | Thr | Pro | Trp | |
| | | 195 | | | | | 200 | | | | | 205 | | | | |

| ttg | act | gcc | gaa | aaa | gat | aag | aaa | ttc | tac | ggt | gga | aac | gat | gaa | aac | 672 |
|---|---|---|---|---|---|---|---|---|---|---|---|---|---|---|---|---|
| Leu | Thr | Ala | Glu | Lys | Asp | Lys | Lys | Phe | Tyr | Gly | Gly | Asn | Asp | Glu | Asn | |
| | | 210 | | | | | 215 | | | | | 220 | | | | |

| ggc | aac | gat | gcc | aac | cca | cgc | gat | ctg | gtc | gtc | gag | aca | ctg | gaa | tct | 720 |
|---|---|---|---|---|---|---|---|---|---|---|---|---|---|---|---|---|
| Gly | Asn | Asp | Ala | Asn | Pro | Arg | Asp | Leu | Val | Val | Glu | Thr | Leu | Glu | Ser | |
| 225 | | | | | 230 | | | | | 235 | | | | | 240 | |

| gta | ggg | gat | gcc | atc | aag | ggt | cat | gaa | gaa | gaa | tac | gac | caa | cgc | gac | 768 |
|---|---|---|---|---|---|---|---|---|---|---|---|---|---|---|---|---|
| Val | Gly | Asp | Ala | Ile | Lys | Gly | His | Glu | Glu | Glu | Tyr | Asp | Gln | Arg | Asp | |
| | | | | 245 | | | | | 250 | | | | | 255 | | |

| ccg | tat | gac | ttg | gat | gga | gac | agc | gat | ctg | atg | gag | ccg | gat | ggc | atg | 816 |
|---|---|---|---|---|---|---|---|---|---|---|---|---|---|---|---|---|
| Pro | Tyr | Asp | Leu | Asp | Gly | Asp | Ser | Asp | Leu | Met | Glu | Pro | Asp | Gly | Met | |
| | | | 260 | | | | | 265 | | | | | 270 | | | |

| ctg | gac | aac | ctg | atg | ctg | gtt | cac | tcc | ggt | att | ggt | gaa | gag | act | ggg | 864 |
|---|---|---|---|---|---|---|---|---|---|---|---|---|---|---|---|---|
| Leu | Asp | Asn | Leu | Met | Leu | Val | His | Ser | Gly | Ile | Gly | Glu | Glu | Thr | Gly | |
| | | 275 | | | | | 280 | | | | | 285 | | | | |

| gaa | gat | gcg | gat | gcg | atc | tgg | tct | cac | cgc | tgg | act | ctg | aaa | aag | ccg | 912 |
|---|---|---|---|---|---|---|---|---|---|---|---|---|---|---|---|---|
| Glu | Asp | Ala | Asp | Ala | Ile | Trp | Ser | His | Arg | Trp | Thr | Leu | Lys | Lys | Pro | |
| 290 | | | | | 295 | | | | | 300 | | | | | | |

```
aca gaa att cca ggc acc agc ctg aaa gct tac gac tac atg att cag        960
Thr Glu Ile Pro Gly Thr Ser Leu Lys Ala Tyr Asp Tyr Met Ile Gln
305                 310                 315                 320 cct gaa gat ggc gca ccc ggc gta ttc gca cat gaa tac gga cac aac       1008
Pro Glu Asp Gly Ala Pro Gly Val Phe Ala His Glu Tyr Gly His Asn
                325                 330                 335 ctg gga ctg cca gat ctg tat gac acg aca aga ctg gga cat gat tcg       1056
Leu Gly Leu Pro Asp Leu Tyr Asp Thr Thr Arg Leu Gly His Asp Ser
            340                 345                 350 ccg gtt ggc gca tgg tcg ctg atg tct tcc gga agc cat aca ggt aag       1104
Pro Val Gly Ala Trp Ser Leu Met Ser Ser Gly Ser His Thr Gly Lys
        355                 360                 365 atc ttc caa acc caa cca acc gga ttt gat cct tgg tcc aaa atg atg       1152
Ile Phe Gln Thr Gln Pro Thr Gly Phe Asp Pro Trp Ser Lys Met Met
    370                 375                 380 ctg cag gaa atg tat ggg ggc aag tgg att gag ccg caa gtc atc aat       1200
Leu Gln Glu Met Tyr Gly Gly Lys Trp Ile Glu Pro Gln Val Ile Asn
385                 390                 395                 400 tac gaa gac ctg aaa aaa cgg aaa aag cag gct tcg ctc tac gat ggc       1248
Tyr Glu Asp Leu Lys Lys Arg Lys Lys Gln Ala Ser Leu Tyr Asp Gly
                405                 410                 415 agc agc ctc gat gaa gat ggc aaa gtc atc aag ctg aat atg ccg caa       1296
Ser Ser Leu Asp Glu Asp Gly Lys Val Ile Lys Leu Asn Met Pro Gln
            420                 425                 430 gta gag aag aca ccg ccg gtt caa ccg aaa gac ggc gat tat tct tac       1344
Val Glu Lys Thr Pro Pro Val Gln Pro Lys Asp Gly Asp Tyr Ser Tyr
        435                 440                 445 ttc tcc gat gag ggc gac aat ctg aac acg aag atg act tcg gaa gtg       1392
Phe Ser Asp Glu Gly Asp Asn Leu Asn Thr Lys Met Thr Ser Glu Val
    450                 455                 460 atc gac ctg aca ggc gcc agc tcc gca tcg atg agc ttc gac tcc tgg       1440
Ile Asp Leu Thr Gly Ala Ser Ser Ala Ser Met Ser Phe Asp Ser Trp
465                 470                 475                 480 aga gcg atc gag acc ggg tac gac tac ctg tac gtg aac gtg att gat       1488
Arg Ala Ile Glu Thr Gly Tyr Asp Tyr Leu Tyr Val Asn Val Ile Asp
                485                 490                 495 gtc gac tca ggt gag agc aca aca gta aaa gag tac gat gac gaa acc       1536
Val Asp Ser Gly Glu Ser Thr Thr Val Lys Glu Tyr Asp Asp Glu Thr
            500                 505                 510 aaa ggc tgg gat aag gaa gaa atc agc ctg aac gat ttc gct ggc aaa       1584
Lys Gly Trp Asp Lys Glu Glu Ile Ser Leu Asn Asp Phe Ala Gly Lys
        515                 520                 525 aag att caa gtc gag ttc aac tac gtg acg gat ggc ggc ttg gcg atg       1632
Lys Ile Gln Val Glu Phe Asn Tyr Val Thr Asp Gly Gly Leu Ala Met
    530                 535                 540 tcc ggc ttc tat ctg gat aat ttt gca gtc aca gca gac ggc gaa gta       1680
Ser Gly Phe Tyr Leu Asp Asn Phe Ala Val Thr Ala Asp Gly Glu Val
545                 550                 555                 560 gtc ttc tcg gat gat gca gaa ggc gac cag aag ttt gat ctg gat gga       1728
Val Phe Ser Asp Asp Ala Glu Gly Asp Gln Lys Phe Asp Leu Asp Gly
                565                 570                 575 ttc atc cat ttc gac ggc gaa ggc aaa atg tac gac gcg tac tac ctg       1776
Phe Ile His Phe Asp Gly Glu Gly Lys Met Tyr Asp Ala Tyr Tyr Leu
            580                 585                 590 gta gag ctg cgc tcc cat gaa ggc gtg gac gag ggt ctg aaa tac ttc       1824
Val Glu Leu Arg Ser His Glu Gly Val Asp Glu Gly Leu Lys Tyr Phe
        595                 600                 605 cgc cgc aat gac aca ttc ttc acg tat gat cca ggt ctg gtg atc tgg       1872
Arg Arg Asn Asp Thr Phe Phe Thr Tyr Asp Pro Gly Leu Val Ile Trp
    610                 615                 620
```

-continued

```
tac tac gat gga cgc ttt ggc aaa acg caa gac aac aac acc agc aac    1920
Tyr Tyr Asp Gly Arg Phe Gly Lys Thr Gln Asp Asn Asn Thr Ser Asn
625                 630                 635                 640 cat cca ggc tac ggc atg ctg ggc gta gtc gat gcg cat cag gaa gtt    1968
His Pro Gly Tyr Gly Met Leu Gly Val Val Asp Ala His Gln Glu Val
                645                 650                 655 cgt tac tgg aat aac gat gag ggc aac gag gag gcc att gcc gac tcc    2016
Arg Tyr Trp Asn Asn Asp Glu Gly Asn Glu Glu Ala Ile Ala Asp Ser
            660                 665                 670 cgt tac caa gtg aac gat gcg gca ttc agc ccg aac aaa acc tcc ggc    2064
Arg Tyr Gln Val Asn Asp Ala Ala Phe Ser Pro Asn Lys Thr Ser Gly
        675                 680                 685 atg gat ctc gac tac att ctc ggc acg atg gat tac gag ccg ctg aaa    2112
Met Asp Leu Asp Tyr Ile Leu Gly Thr Met Asp Tyr Glu Pro Leu Lys
    690                 695                 700 ggc att acc gta ttc aaa gac agt gat gat tac acg atg ccg gaa gtt    2160
Gly Ile Thr Val Phe Lys Asp Ser Asp Asp Tyr Thr Met Pro Glu Val
705                 710                 715                 720 ccg gaa atc gga aaa atc ctg ccg aag atc ggt ctg caa atc aaa tta    2208
Pro Glu Ile Gly Lys Ile Leu Pro Lys Ile Gly Leu Gln Ile Lys Leu
                725                 730                 735 att cgt gtg tcc aag aaa ttc acg aac gca cag gtc gag ttc tcc atc    2256
Ile Arg Val Ser Lys Lys Phe Thr Asn Ala Gln Val Glu Phe Ser Ile
            740                 745                 750 aaa aaa taa                                                        2265
Lys Lys

<210> SEQ ID NO 4
<211> LENGTH: 754
<212> TYPE: PRT
<213> ORGANISM: Brevibacillus choshinensis

<400> SEQUENCE: 4

Val Asn Ala Val Lys Lys Gly Lys Lys Leu Leu Ser Ile Leu Phe Ser
  1               5                  10                  15

Ser Ser Leu Val Leu Ser Gly Ile Ala Ala Val Pro Ala Thr Gly Met
                 20                  25                  30

Ala Lys Ser Lys Asp Lys Pro Pro Leu Glu Val Asp Leu Ser Thr Val
             35                  40                  45

Asn Met Asp Arg Leu Val Lys Ala Leu Ile Asp Gln Gly Glu Ile Asp
         50                  55                  60

Glu Asp Ala Asp Gln Glu Glu Ile Asn Lys Ala Val Glu Lys Phe Leu
 65                  70                  75                  80

Arg Asp Lys Lys Val Pro His Gly Ile Asp Asp Ser Ser Ser Phe Gly
                 85                  90                  95

Lys Lys Ala Ser Lys Thr Gln Leu Ser Ala Val Ser Lys Ala Ala Ser
            100                 105                 110

Lys Val Ser Lys Leu Lys Asp Asp Lys Gln Val Arg Ala Ser Lys Arg
        115                 120                 125

Val His Thr Asp Asn Leu Val Ile Ala Leu Val Glu Phe Asn Asp Leu
    130                 135                 140

Glu His Asn Gln Val Pro Lys Gln Ser Asp Ser Leu Trp Thr Ala Asp
145                 150                 155                 160

Phe Asp Gln Lys His Tyr Glu Glu Met Leu Phe Asp Arg Lys Gly Tyr
                165                 170                 175

Thr Thr Pro Glu Gly Ile Ser Met Thr Thr Met Ala Lys Tyr Tyr Tyr
            180                 185                 190
```

-continued

```
Glu Gln Ser Gly Glu Thr Trp Thr Val Asp Gly Val Val Thr Pro Trp
            195                 200                 205
Leu Thr Ala Glu Lys Asp Lys Lys Phe Tyr Gly Gly Asn Asp Glu Asn
    210                 215                 220
Gly Asn Asp Ala Asn Pro Arg Asp Leu Val Val Glu Thr Leu Glu Ser
225                 230                 235                 240
Val Gly Asp Ala Ile Lys Gly His Glu Glu Tyr Asp Gln Arg Asp
                245                 250                 255
Pro Tyr Asp Leu Asp Gly Asp Ser Asp Leu Met Glu Pro Asp Gly Met
            260                 265                 270
Leu Asp Asn Leu Met Leu Val His Ser Gly Ile Gly Glu Glu Thr Gly
    275                 280                 285
Glu Asp Ala Asp Ala Ile Trp Ser His Arg Trp Thr Leu Lys Lys Pro
290                 295                 300
Thr Glu Ile Pro Gly Thr Ser Leu Lys Ala Tyr Asp Tyr Met Ile Gln
305                 310                 315                 320
Pro Glu Asp Gly Ala Pro Gly Val Phe Ala His Glu Tyr Gly His Asn
                325                 330                 335
Leu Gly Leu Pro Asp Leu Tyr Asp Thr Thr Arg Leu Gly His Asp Ser
            340                 345                 350
Pro Val Gly Ala Trp Ser Leu Met Ser Ser Gly Ser His Thr Gly Lys
    355                 360                 365
Ile Phe Gln Thr Gln Pro Thr Gly Phe Asp Pro Trp Ser Lys Met Met
    370                 375                 380
Leu Gln Glu Met Tyr Gly Gly Lys Trp Ile Glu Pro Gln Val Ile Asn
385                 390                 395                 400
Tyr Glu Asp Leu Lys Lys Arg Lys Lys Gln Ala Ser Leu Tyr Asp Gly
                405                 410                 415
Ser Ser Leu Asp Glu Asp Gly Lys Val Ile Lys Leu Asn Met Pro Gln
            420                 425                 430
Val Glu Lys Thr Pro Pro Val Gln Pro Lys Asp Gly Asp Tyr Ser Tyr
    435                 440                 445
Phe Ser Asp Glu Gly Asp Asn Leu Asn Thr Lys Met Thr Ser Glu Val
    450                 455                 460
Ile Asp Leu Thr Gly Ala Ser Ser Ala Ser Met Ser Phe Asp Ser Trp
465                 470                 475                 480
Arg Ala Ile Glu Thr Gly Tyr Asp Tyr Leu Tyr Val Asn Val Ile Asp
                485                 490                 495
Val Asp Ser Gly Glu Ser Thr Thr Val Lys Glu Tyr Asp Asp Glu Thr
            500                 505                 510
Lys Gly Trp Asp Lys Glu Glu Ile Ser Leu Asn Asp Phe Ala Gly Lys
    515                 520                 525
Lys Ile Gln Val Glu Phe Asn Tyr Val Thr Asp Gly Gly Leu Ala Met
    530                 535                 540
Ser Gly Phe Tyr Leu Asp Asn Phe Ala Val Thr Ala Asp Gly Glu Val
545                 550                 555                 560
Val Phe Ser Asp Asp Ala Glu Gly Asp Gln Lys Phe Asp Leu Asp Gly
                565                 570                 575
Phe Ile His Phe Asp Gly Glu Gly Lys Met Tyr Asp Ala Tyr Tyr Leu
            580                 585                 590
Val Glu Leu Arg Ser His Glu Gly Val Asp Glu Gly Leu Lys Tyr Phe
    595                 600                 605
```

```
Arg Arg Asn Asp Thr Phe Phe Thr Tyr Asp Pro Gly Leu Val Ile Trp
    610                 615                 620

Tyr Tyr Asp Gly Arg Phe Gly Lys Thr Gln Asp Asn Asn Thr Ser Asn
625                 630                 635                 640

His Pro Gly Tyr Gly Met Leu Gly Val Val Asp Ala His Gln Glu Val
                645                 650                 655

Arg Tyr Trp Asn Asn Asp Glu Gly Asn Glu Glu Ala Ile Ala Asp Ser
                660                 665                 670

Arg Tyr Gln Val Asn Asp Ala Ala Phe Ser Pro Asn Lys Thr Ser Gly
            675                 680                 685

Met Asp Leu Asp Tyr Ile Leu Gly Thr Met Asp Tyr Glu Pro Leu Lys
690                 695                 700

Gly Ile Thr Val Phe Lys Asp Ser Asp Tyr Thr Met Pro Glu Val
705                 710                 715                 720

Pro Glu Ile Gly Lys Ile Leu Pro Lys Ile Gly Leu Gln Ile Lys Leu
                725                 730                 735

Ile Arg Val Ser Lys Lys Phe Thr Asn Ala Gln Val Glu Phe Ser Ile
                740                 745                 750

Lys Lys
```

<210> SEQ ID NO 5
<211> LENGTH: 1362
<212> TYPE: DNA
<213> ORGANISM: Brevibacillus choshinensis
<220> FEATURE:
<221> NAME/KEY: CDS
<222> LOCATION: (1)..(1359)

<400> SEQUENCE: 5

```
atg aac cat cct gat ttt cgc gat cta ccc gcc tgc atg gaa gac gta    48
Met Asn His Pro Asp Phe Arg Asp Leu Pro Ala Cys Met Glu Asp Val
 1               5                  10                  15 acc ctc gct gcc ctg gac gag tac act ggt cca cca gat ccg acc gaa    96
Thr Leu Ala Ala Leu Asp Glu Tyr Thr Gly Pro Pro Asp Pro Thr Glu
             20                  25                  30 tac caa tca ttg tat gga cgc ttg caa gag gtt gcc gaa act ctc cct   144
Tyr Gln Ser Leu Tyr Gly Arg Leu Gln Glu Val Ala Glu Thr Leu Pro
         35                  40                  45 ccg ctc tat cgg gag cat gtg tat cac cct ttt ctt caa gcg atg gac   192
Pro Leu Tyr Arg Glu His Val Tyr His Pro Phe Leu Gln Ala Met Asp
     50                  55                  60 aag ttg tct gag tca gga ttt gcg cag atg ctc cgt cga gat cct caa   240
Lys Leu Ser Glu Ser Gly Phe Ala Gln Met Leu Arg Arg Asp Pro Gln
 65                  70                  75                  80 aaa gag cga gaa gcc ggt ctg ttt tgc gat atc gca cag gcc att ctg   288
Lys Glu Arg Glu Ala Gly Leu Phe Cys Asp Ile Ala Gln Ala Ile Leu
                 85                  90                  95 caa aac ggc gaa gcg tat gaa cgc gat gcc acg gat gcc ttt cag gaa   336
Gln Asn Gly Glu Ala Tyr Glu Arg Asp Ala Thr Asp Ala Phe Gln Glu
            100                 105                 110 gta gtc agc gat ttg tac gac ggt ttt tta agc gag gaa gac agg agt   384
Val Val Ser Asp Leu Tyr Asp Gly Phe Leu Ser Glu Glu Asp Arg Ser
        115                 120                 125 ggc atc aaa ccg cct gat gaa agc ttg att gct cct ctg gtc aaa tgg   432
Gly Ile Lys Pro Pro Asp Glu Ser Leu Ile Ala Pro Leu Val Lys Trp
    130                 135                 140 gga cgc ccg caa ttc gga cct tat acg tgg aca gct gaa gcc gct gcc   480
Gly Arg Pro Gln Phe Gly Pro Tyr Thr Trp Thr Ala Glu Ala Ala Ala
145                 150                 155                 160
```

```
cat ttt ggc atc aag acg ggc att gtc aat ttg ccc ccg gca aac gcc      528
His Phe Gly Ile Lys Thr Gly Ile Val Asn Leu Pro Pro Ala Asn Ala
            165                 170                 175 cgc ctg ggt ctg ctc gcg tgg tct gca tta ggt cac gaa acg gct gga      576
Arg Leu Gly Leu Leu Ala Trp Ser Ala Leu Gly His Glu Thr Ala Gly
            180                 185                 190 cac gac att ctc cac gcc gac acc ggt ttg ctt gga gaa ctg cag caa      624
His Asp Ile Leu His Ala Asp Thr Gly Leu Leu Gly Glu Leu Gln Gln
            195                 200                 205 acc gtc tat gac gct ttg ttt gat gag ctt cac aat cgg acg ctg gcg      672
Thr Val Tyr Asp Ala Leu Phe Asp Glu Leu His Asn Arg Thr Leu Ala
210                 215                 220 gac tac tgg tcg ctc cga atc gac gag act gcc tcc gac gtt ttg gga      720
Asp Tyr Trp Ser Leu Arg Ile Asp Glu Thr Ala Ser Asp Val Leu Gly
225                 230                 235                 240 atc ctg aac acc ggc ccc gct gca ggg att gga ctg att gga tat ttc      768
Ile Leu Asn Thr Gly Pro Ala Ala Gly Ile Gly Leu Ile Gly Tyr Phe
            245                 250                 255 cgc ggc ctt aat aag gcg tac acc gga caa gca aca ctg cgg aat aca      816
Arg Gly Leu Asn Lys Ala Tyr Thr Gly Gln Ala Thr Leu Arg Asn Thr
            260                 265                 270 ggg cca cag aat gac cca cat cca gca gac atc ttg cgc ggt tat ctt      864
Gly Pro Gln Asn Asp Pro His Pro Ala Asp Ile Leu Arg Gly Tyr Leu
            275                 280                 285 gct gct gag act gct cgt ctg ctg cat ttt gac aac gca tcc gac tgg      912
Ala Ala Glu Thr Ala Arg Leu Leu His Phe Asp Asn Ala Ser Asp Trp
            290                 295                 300 gca cag gca ctt ctc gag gaa acc agg cgt gat ctt aaa ggc atc aca      960
Ala Gln Ala Leu Leu Glu Glu Thr Arg Arg Asp Leu Lys Gly Ile Thr
305                 310                 315                 320 ata ggc aga gcc tct ttg gat gca gaa acc gct caa aaa tct gct gcc     1008
Ile Gly Arg Ala Ser Leu Asp Ala Glu Thr Ala Gln Lys Ser Ala Ala
            325                 330                 335 att gtc gct cgc aca att atg gaa gca cgc ctg ctc agt ctg gaa ggt     1056
Ile Val Ala Arg Thr Ile Met Glu Ala Arg Leu Leu Ser Leu Glu Gly
            340                 345                 350 cat gcc ctc ggg caa att caa aac tgg cac aac gag gat gaa cga atc     1104
His Ala Leu Gly Gln Ile Gln Asn Trp His Asn Glu Asp Glu Arg Ile
            355                 360                 365 gtt cag gaa att cgc tcc cat ttt aca ggt tcc ctg acc gtg caa gac     1152
Val Gln Glu Ile Arg Ser His Phe Thr Gly Ser Leu Thr Val Gln Asp
            370                 375                 380 ggc att gtt tcg ggt atg tat gct gcg cat gtc gtg gca gca gcc gtc     1200
Gly Ile Val Ser Gly Met Tyr Ala Ala His Val Val Ala Ala Ala Val
385                 390                 395                 400 caa gca gcc gtt tca gga gag atg gat acc tcc gct gcc ttc aca ggg     1248
Gln Ala Ala Val Ser Gly Glu Met Asp Thr Ser Ala Ala Phe Thr Gly
            405                 410                 415 atg aaa acc ttg ctg aag agc atg cac gac gcc aat cct tcc tgg gga     1296
Met Lys Thr Leu Leu Lys Ser Met His Asp Ala Asn Pro Ser Trp Gly
            420                 425                 430 cct ctc tat gta cga tat cgc ggt gat ctc act ccg cat cgc att tac     1344
Pro Leu Tyr Val Arg Tyr Arg Gly Asp Leu Thr Pro His Arg Ile Tyr
            435                 440                 445 tcc cgt tct gcg agc tag                                             1362
Ser Arg Ser Ala Ser
            450
```

<210> SEQ ID NO 6

```
<211> LENGTH: 453
<212> TYPE: PRT
<213> ORGANISM: Brevibacillus choshinensis

<400> SEQUENCE: 6

Met Asn His Pro Asp Phe Arg Asp Leu Pro Ala Cys Met Glu Asp Val
 1               5                  10                  15

Thr Leu Ala Ala Leu Asp Glu Tyr Thr Gly Pro Pro Asp Pro Thr Glu
            20                  25                  30

Tyr Gln Ser Leu Tyr Gly Arg Leu Gln Glu Val Ala Glu Thr Leu Pro
        35                  40                  45

Pro Leu Tyr Arg Glu His Val Tyr His Pro Phe Leu Gln Ala Met Asp
    50                  55                  60

Lys Leu Ser Glu Ser Gly Phe Ala Gln Met Leu Arg Arg Asp Pro Gln
65                  70                  75                  80

Lys Glu Arg Glu Ala Gly Leu Phe Cys Asp Ile Ala Gln Ala Ile Leu
                85                  90                  95

Gln Asn Gly Glu Ala Tyr Glu Arg Asp Ala Thr Asp Ala Phe Gln Glu
            100                 105                 110

Val Val Ser Asp Leu Tyr Asp Gly Phe Leu Ser Glu Glu Asp Arg Ser
        115                 120                 125

Gly Ile Lys Pro Pro Asp Glu Ser Leu Ile Ala Pro Leu Val Lys Trp
    130                 135                 140

Gly Arg Pro Gln Phe Gly Pro Tyr Thr Trp Thr Ala Glu Ala Ala Ala
145                 150                 155                 160

His Phe Gly Ile Lys Thr Gly Ile Val Asn Leu Pro Pro Ala Asn Ala
                165                 170                 175

Arg Leu Gly Leu Leu Ala Trp Ser Ala Leu Gly His Glu Thr Ala Gly
            180                 185                 190

His Asp Ile Leu His Ala Asp Thr Gly Leu Leu Gly Glu Leu Gln Gln
        195                 200                 205

Thr Val Tyr Asp Ala Leu Phe Asp Glu Leu His Asn Arg Thr Leu Ala
    210                 215                 220

Asp Tyr Trp Ser Leu Arg Ile Asp Glu Thr Ala Ser Asp Val Leu Gly
225                 230                 235                 240

Ile Leu Asn Thr Gly Pro Ala Ala Gly Ile Gly Leu Ile Gly Tyr Phe
                245                 250                 255

Arg Gly Leu Asn Lys Ala Tyr Thr Gly Gln Ala Thr Leu Arg Asn Thr
            260                 265                 270

Gly Pro Gln Asn Asp Pro His Pro Ala Asp Ile Leu Arg Gly Tyr Leu
        275                 280                 285

Ala Ala Glu Thr Ala Arg Leu Leu His Phe Asp Asn Ala Ser Asp Trp
    290                 295                 300

Ala Gln Ala Leu Leu Glu Glu Thr Arg Arg Asp Leu Lys Gly Ile Thr
305                 310                 315                 320

Ile Gly Arg Ala Ser Leu Asp Ala Glu Thr Ala Gln Lys Ser Ala Ala
                325                 330                 335

Ile Val Ala Arg Thr Ile Met Glu Ala Arg Leu Leu Ser Leu Glu Gly
            340                 345                 350

His Ala Leu Gly Gln Ile Gln Asn Trp His Asn Glu Asp Glu Arg Ile
        355                 360                 365

Val Gln Glu Ile Arg Ser His Phe Thr Gly Ser Leu Thr Val Gln Asp
    370                 375                 380

Gly Ile Val Ser Gly Met Tyr Ala Ala His Val Val Ala Ala Ala Val
```

```
                385                 390                 395                 400
        Gln Ala Ala Val Ser Gly Glu Met Asp Thr Ser Ala Ala Phe Thr Gly
                        405                 410                 415
        Met Lys Thr Leu Leu Lys Ser Met His Asp Ala Asn Pro Ser Trp Gly
                    420                 425                 430
        Pro Leu Tyr Val Arg Tyr Arg Gly Asp Leu Thr Pro His Arg Ile Tyr
                435                 440                 445
        Ser Arg Ser Ala Ser
            450

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggggtacct cactctgtca gcatgctg                                      28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggggatccc ggcgtgattc ccactgc                                       27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggctgcaga tagcggatga aggtgtg                                       27

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggtctagac ctgcttatac atctgtttcg                                    30

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagagaccat ggaccatcct gattttcgcg atctacccg                          39
```

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agaattcagt ggtggtggtg gtggtggtgg tggctcgcag aacgggagta aatgcgatgc      60

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaaagaattc tttctgcaga acaggatgcg ggggagccgc cgct      44

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaaaggatc cttatagcat ctaatcttca acaaact      37

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaaaagat cttgaacgat gacctctaat aattgttaa      39

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaaagaattc aaatctagaa agtgtgtgct ctgcgaggct gtc      43

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccatggcac aatttggtat attatgtaaa      30

```
<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actcgagtta tatgcgtcta tttatgtagg at                                    32

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 tttttctag actttatgaa tataaagtat agtgtgt                                37

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20 ggggctgca gttatatgcg tctatttatg taggatg                                37

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (15)
<223> OTHER INFORMATION: a, c, g or t

<400> SEQUENCE: 21
aarcgngtnc ayacngayaa yct                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, g or t
<220> FEATURE:
<221> NAME/KEY: modified_base
<222> LOCATION: (6)
<223> OTHER INFORMATION: inosine
```

```
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (15)
<223> OTHER INFORMATION: a, c, g or t

<400> SEQUENCE: 22
aanccngtng gytgngtytg gaa                                         23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctcgtagtg cttttggtcg aag                                         23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accaataccg gagtgaacca gca                                         23

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actatagggc acgcgtggt                                              19

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcccatggc tttcgctacc cccgtgcagt ccgtggactg c                     41

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atataagctt ttagggagag aggacttcca tggt                             34
```

```
<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttctgcagg taaaatcgaa gaaggtaaac tggta                              35

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaaaagcttt tacttggtga tacgagtctg cgcg                               34

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttttggatcc gaggaggtgt cggagaactg tagccac                            37

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaaaagcttc tacactggca gctcctcctg tctg                               34

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaggatcccc gtcatatccg gca                                           23

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaaagcttta ggcgttatcc gctttagc                                      28

<210> SEQ ID NO 34
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tatatccatg gcttcttact gccaggcgcc cttttttaa                         39

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atataagctt ttattttgat gctctctggc cttggaa                           37

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atattcatga gcaacgactt gcttcgatcc ca                                32

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atataagctt tcagttctgg agataatctg taagta                            36

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Arg Val His Thr Asp Asn Leu
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Gln Thr Gln Pro Thr Gly Phe
  1               5
```

```
<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ser Lys Arg Val His Thr Asp Asn Leu Val Ile Ala Leu Val Glu
 1               5                  10                  15

Phe Asn Asp Leu Glu Gly Asn Gln
            20

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Phe Gln Thr Gln Pro Thr Gly Phe Asp
 1               5                  10
```